(12) United States Patent
Cuadrado Tejedor et al.

(10) Patent No.: US 9,969,744 B2
(45) Date of Patent: May 15, 2018

(54) COMPOUNDS FOR USE IN COGNITION IMPROVEMENT

(71) Applicant: FUNDACIÓN PARA LA INVESTIGACIÓN MÉDICA APLICADA, Pamplona (ES)

(72) Inventors: María del Mar Cuadrado Tejedor, Pamplona (ES); Ana María García Osta, Pamplona (ES); Julen Oyarzabal Santamarina, Pamplona (ES); Maria Obdulia Rabal Gracia, Pamplona (ES); Juan Antonio Sánchez Arias, Pamplona (ES); Ana Ugarte Baztán, Pamplona (ES)

(73) Assignee: FUNDACIÓN LA INVESTIGACIÓN MÉDICA APLICADA, Pamplona (ES)

( * ) Notice: Subject to any disclaimer, the term of this patent is extended or adjusted under 35 U.S.C. 154(b) by 0 days. days.

(21) Appl. No.: 15/501,814

(22) PCT Filed: Aug. 3, 2015

(86) PCT No.: PCT/EP2015/067764
§ 371 (c)(1),
(2) Date: Feb. 3, 2017

(87) PCT Pub. No.: WO2016/020307
PCT Pub. Date: Feb. 11, 2016

(65) Prior Publication Data
US 2017/0217973 A1    Aug. 3, 2017

(30) Foreign Application Priority Data
Aug. 4, 2014  (EP) ..................................... 14382306

(51) Int. Cl.
*C07D 487/00* (2006.01)
*C07D 487/04* (2006.01)
(52) U.S. Cl.
CPC ................. *C07D 487/04* (2013.01)
(58) Field of Classification Search
None
See application file for complete search history.

(56) References Cited

U.S. PATENT DOCUMENTS

2005/0288282 A1    12/2005    Delorme et al.

FOREIGN PATENT DOCUMENTS

| EP | 2535049 A1 | 12/2012 |
| GB | 2388594 A | 11/2003 |
| WO | WO 2000/21926 A2 | 4/2000 |
| WO | WO 2014/131855 A1 | 9/2014 |

OTHER PUBLICATIONS

Cuadrado-Tejedor, M., et al: "A first-in-class small-molecule that acts as a dual inhibitor of HDAC and PDE5, and that rescues hippocampal synaptic impairment in Alzheimer's disease mice", Neuropsychopharmacology, Jan. 2017, 47 pages.
Cuadrado-Tejedor, M., et al: "Concomitant histone deacetylase and phosphodiesterase 5 inhibition synergistically prevents the disruption in synaptic plasticity and it reverses cognitive impairment in a mouse model of Alzheimer's disease", Clinical Epigenetics, Oct. 8, 2015, vol. 7, No. 108, 11 pages.
International Search Report and Written Opinion dated Sep. 18, 2015 for PCT/EP2015/067764, 11 pages.
Meng, et al: "Structure-based discovery of highly selective phosphodiesterase-9A inhibitors and implications for inhibitor design", J. Med Chem 2012, Sep. 17, 2012, vol. 55, No. 19, pp. 8549-8558, 10 pages.

*Primary Examiner* — Jeffrey H Murray
(74) *Attorney, Agent, or Firm* — Squire Patton Boggs (US) LLP

(57) ABSTRACT

Novel compounds for use in cognition improvement It relates to certain compounds having a polycyclic structure and a —(C=O)NR$^a$R$^b$ moiety, wherein the polycyclic structure comprises at least three ring systems, wherein one ring system is a polycyclic ring system comprising from 2 to 4 rings; at least one ring is an aromatic ring; and wherein the structure comprises at least 3 nitrogen atoms and 1 oxygen atom. It also relates to pharmaceutical compositions containing them, and to their use in medicine, in particular in the treatment and/or prevention of neurological disorders coursing with a cognition deficit or impairment, or neurodegenerative diseases.

19 Claims, No Drawings

COMPOUNDS FOR USE IN COGNITION IMPROVEMENT

CROSS-REFERENCE TO RELATED APPLICATIONS

This application is a U.S. national stage entry of International Patent Application No. PCT/EP2015/067764, filed Aug. 3, 2015, which claims the benefit of European Patent Application No. 14382306.0, filed Aug. 4, 2014. Each of the foregoing applications is incorporated herein by reference in its entirety.

The present invention relates to compounds, which are dual inhibitors of PDEs and HDACs; and to processes for their preparation. It also relates to pharmaceutical compositions containing them, and to their use in medicine, in particular in the treatment and/or prevention of neurological disorders coursing with a cognition deficit or impairment, or neurodegenerative diseases.

BACKGROUND ART

Mild cognitive impairment is characterized by deficits in memory, language and/or other essential cognitive functions that do not interfere with an individual's daily life. The condition often evolves towards dementia, which is characterized by a global deterioration of cognitive abilities to an extent that does interfere with daily life. Alzheimer's disease (AD) is the most common form of dementia among older people and refers to dementia that does not have an antecedent cause, such as stroke, brain trauma, or alcohol; it is characterized by the presence in the brain of extracellular amyloid plaques and intracellular neurofibrillary tangles that provoke neuronal dysfunction and cell death. The increasing number of AD patients associated with the aging of the population makes the development of new disease management/treatment strategies critical.

The search for effective AD management has been largely based on the amyloid (Aβ) hypothesis, mainly focusing on reducing the number of senile plaques, although with little success to date. Focus is placed now on other hallmarks of the disease such as hyperphosphorylation of the cytoskeletal protein tau, which is the main component of neurofibrillary tangles.

Gene transcription and protein synthesis plays an important role in the formation of new memories. An increase in histone (H3 and/or H4) acetylation using histone deacetylase (HDAC) inhibitors induces chromatin re-structuring, which is associated with gene transcription activation. HDAC proteins are classified in four families: class I (HDAC 1-3, HDAC8), class IIa (HDAC 4, 5, 7 and 9), class IIb (HDAC 6 and 10), and class IV (HDAC 11). The expression pattern of each HDACs in the central nervous system (CNS) and its contribution in memory function varies among each subtype.

4-phenylbutyrate (PBA), a HDAC inhibitor, is an effective cognitive-enhancer in the Tg2576 transgenic mouse model of AD, which overexpresses a mutant form of the amyloid precursor protein (APP). Additionally, PBA reversed the pathological hallmarks of the disease and restored dendritic spine loss in this animal model. Taking into account that PBA inhibits HDACs class I and IIb, all these data strongly suggest the potential for therapeutic benefits of HDAC inhibitors in AD. Class I HDAC inhibitors enhance memory function by increasing histone acetylation levels, which facilitates gene transcription in the brain.

Moreover, aging is associated with an increase in phosphodiesterase (PDE) expression and activity. Thus, phosphodiesterases (PDEs) are good candidates for non-amyloid targets in cognition deficits in general and in AD in particular. Rolipram, which is a specific PDE4 inhibitor, was the first that proved useful in restoring cognition deficits in animal models of AD.

Specific phosphodiesterase (PDE) inhibitors (e.g. PDE5 inhibitors: Sildenafil, or Tadalafil; and, PDE9 inhibitor: PF-4447943 (6-[(3S,4S)-4-methyl-1-(pyrimidin-2-ylmethyl)pyrrolidin-3-yl]-1-(tetrahydro-2H-pyran-4-yl)-1H-pyrazolo[3,4-d]pyrimidin-4(5H)-one)) have been shown to improve memory performance or/and enhance synaptic plasticity and cognitive function in different animal models of AD. PDE inhibitors regulate signalling pathways by elevating levels of cAMP and/or cGMP, which may ultimately promote gene transcription by directly and/or indirectly activating the cAMP response element-binding (CREB). CREB-dependent gene expression underlies long-term memory formation and persistent long-term potentiation (LTP), which are indicators of synaptic plasticity and strength. In the hippocampus, this probably occurs through the formation of new synaptic connections, which are needed to restore cognitive deficits. Thus, by activating the CREB signalling pathway, PDE inhibitors may ameliorate AD symptoms. Moreover, other CREB-independent mechanisms seem to act in synergy to restore cognitive impairment in AD via increase of cAMP and/or cGMP levels. Cognitive performance may be also improved indirectly by means of PDE-inhibitor-mediated increase of cerebral blood flow and/or of brain glucose consumption.

Besides amyloid burden, Tau phosphorylation is another histopathological marker of AD progression. Importantly, it has been shown that the PDE5 inhibitors Sildenafil and Tadalafil, reduce Tau phosphorylation (pTau levels) in different animal models of AD.

Therefore, there is still a need of developing compounds which show improved activity in the treatment and/or prevention of neurological disorders coursing with a cognition deficit or impairment, or neurodegenerative diseases.

SUMMARY OF THE INVENTION

Inventors have found new compounds having a polycyclic structure and a —(C=O)NR$^a$R$^b$ moiety which are capable to inhibit one or more phosphodiesterases (PDE) and simultaneously one or more histone deacetylases (HDACs). These compounds are therefore dual inhibitors of PDEs and HDACs and could be useful to improve cognition. The compounds of the invention have the advantage that are addressed to two different pathways of those that, in animal models, have proved useful to prevent the progression of neurodegenerative diseases and/or to increase cognition deficits associated to neurodegenerative diseases. Considering that the major drawback of the treatments for AD in clinical phases is their lack of efficacy when targeting a single pathophysiological event; the compounds of the present invention, which have an impact on two pathophysiological events, may lead to a more efficacious treatment.

Therefore, a first aspect of the invention relates to a compound of formula (I), or a pharmaceutically acceptable salt thereof, or any stereoisomer or mixtures thereof, either of the compound of formula (I) or of any of its pharmaceutically acceptable salts,

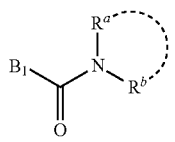
(I)

wherein the moiety —NR$^a$R$^b$, wherein the dashed line means that R$^a$ and R$^b$ optionally form a known ring system, is selected from the group consisting of formula (M$^1$), formula (M$^2$), formula (M$^3$), and formula (M$^4$):

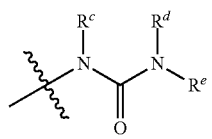
(M$^1$)

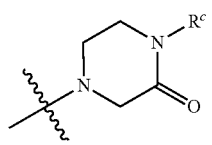
(M$^2$)

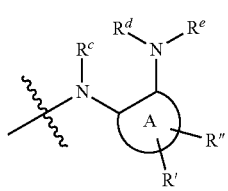
(M$^3$)

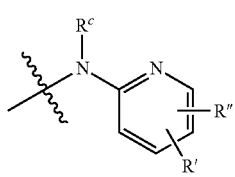
(M$^4$)

B$_1$ is a radical selected from the group consisting of formula (A"), formula (B"), formula (C"), and formula (D"):

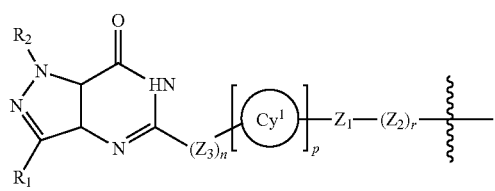
(A")

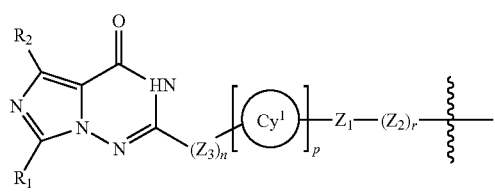
(B")

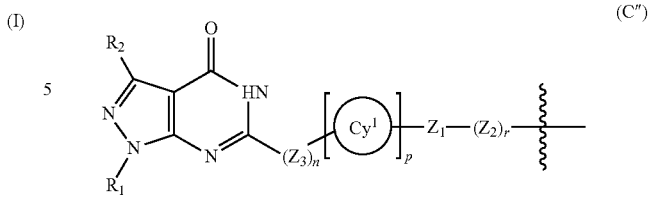
(C")

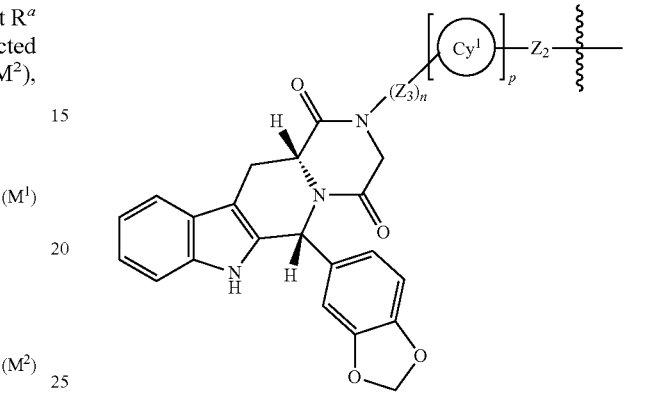
(D")

R$^c$ is hydrogen;

R$^d$ and R$^e$ are independently selected from H, —(C$_1$-C$_7$) alkyl optionally substituted with one or more halogen atoms, and a known 3- to 8-membered carbocyclic monocyclic ring, saturated or partially unsaturated, which is optionally substituted with one or more halogen atoms;

A is a known ring system selected from phenyl and 5- to 6-membered heteroaromatic ring, wherein the substituents —NR$^c$— and —NR$^d$R$^e$ are attached to adjacent carbon atoms;

R' and R" are independently selected from the group consisting of H, R$^f$, phenyl optionally substituted with one or more substituents R$^f$, 5- or 6-membered heteroaromatic ring optionally substituted with one or more substituents R$^f$, and —(C$_1$-C$_7$)alkyl optionally substituted with one or more halogen atoms;

each R$^f$ is independently selected from halogen, —NO$_2$, —CN, —OR$^g$, —OC(O)R$^g$, —OC(O)OR$^g$, —OC(O)NR$^g$R$^g$, —NR$^g$R$^g$, —NR$^g$C(O)R$^g$, —NR$^g$C(O)OR$^g$, —NR$^g$C(O)NR$^g$R$^g$, —NR$^g$S(O)$_2$R$^g$, —NR$^g$SO$_2$NRR$^g$, —SR$^g$, —S(O)R$^g$, —SO$_2$R$^g$, —SO$_2$(OR$^g$), —SO$_2$NR$^g$R$^g$, —C(O)R$^g$, —C(O)OR$^g$, —C(O)NR$^g$R$^g$, and —C(O)NR$^g$OR$^g$;

each R$^g$ is independently selected from H, —(C$_1$-C$_7$)alkyl optionally substituted with one or more halogen atoms, and a known 3- to 7-membered carbocyclic monocyclic ring, saturated or partially unsaturated, which is optionally substituted with one or more halogen atoms;

p, n and r are independently 0 or 1;

R$_1$ and R$_2$ are independently selected from the group consisting of H; saturated or unsaturated (C$_1$-C$_7$)alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from halogen and (C$_1$-C$_3$) alkyl;

Z$_1$ is a biradical selected from the group consisting of a formula (E), formula (F"), formula (G'), formula (H'), formula (J'), and formula (K):

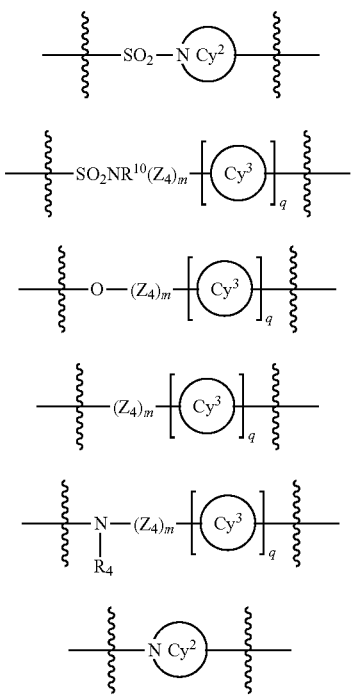

(E)
(F″)
(G′)
(H′)
(J′)
(K)

$Z_2$ is selected from the group consisting of —$Z_5$—; —$Z_5$-$Cy^4$—; —$Z_5$—$Cy^4$—$Z_5$—; and -$Cy^4$—;

$Z_3$ and each $Z_5$ are independently a biradical of a saturated or unsaturated ($C_1$-$C_6$)alkyl optionally substituted with one or more halogen atoms;

$Z_4$ is a biradical of a saturated or unsaturated ($C_1$-$C_6$)alkyl optionally substituted with one or more substituents selected from halogen, OH, and —O($C_1$-$C_3$)alkyl optionally substituted with one or more halogen atoms; or alternatively $Z_4$ is —$CR^{11}R^{12}$—, wherein $R^{11}$ and $R^{12}$ taken together with the carbon they are attached to form C=O or a 3- to 7-membered carbocyclic or heterocyclic monocyclic ring, which is saturated or partially unsaturated, and which is optionally substituted with one or more halogen atoms or ($C_1$-$C_3$)alkyl optionally substituted with one or more halogen atoms;

q and m are independently 0 or 1;

$Cy^1$ is a 3- to 7-membered saturated or partially unsaturated heterocyclic monocyclic ring, which is optionally fused, bridged-fused or spiro-fused to a 3- to 7-membered saturated or partially unsaturated carbocyclic or heterocyclic monocyclic ring, wherein $Cy^1$ is optionally substituted with one or more $R_3$ groups;

$Cy^2$ is a N-attached 3- to 7-membered saturated or partially unsaturated heterocyclic monocyclic ring, which is optionally fused, bridged-fused or spiro-fused to a 3- to 7-membered saturated or partially unsaturated carbocyclic or heterocyclic monocyclic ring, wherein $Cy^2$ is optionally substituted with one or more $R_3$ groups;

$Cy^3$ and $Cy^4$ are independently phenyl or a 3- to 7-membered carbocyclic or heterocyclic monocyclic ring, which is saturated or partially unsaturated or aromatic, and which is optionally substituted with one or more $R_3$ groups;

$R_3$ is selected from halogen; saturated or unsaturated ($C_1$-$C_7$)alkyl optionally substituted with one or more halogen atoms; saturated or unsaturated —O($C_1$-$C_7$)alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from the group consisting of halogen and ($C_1$-$C_6$)alkyl optionally substituted with one or more halogen atoms;

$R^4$ and $R^{10}$ are independently H or ($C_1$-$C_6$)alkyl optionally substituted with one or more halogen atoms; and wherein in any heterocyclic ring one or more of the ring members are selected from NH, N, O, and S;

wherein in all saturated or partially unsaturated rings one or two members of the rings are optionally C(=O) and/or C(=NH) and/or C[=N($C_1$-$C_4$)alkyl], wherein saturated alkyl refers to a linear or branched hydrocarbon chain which contains only single bonds; and unsaturated alkyl refers to a linear or branched hydrocarbon chain which contains one or two double bonds and/or one or two triple bonds;

wherein in any alkyl group one or two chain members selected from $CH_2$ or CH are optionally replaced by chain members independently selected from N, $NR_4$, O, C(=O), C(=O)$NR_4$, $NR_4$C(=O), and S; and with the condition that:

the moiety ($L_1$) in the formula (A″), formula (B″), and formula (C″), and the moiety ($L_2$) of the formula (D″)

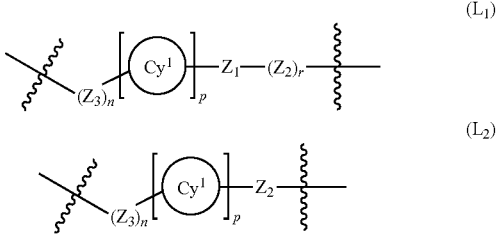

($L_1$)

($L_2$)

have a chain length comprised from 1 to 20 atoms; and when in a compound of formula (I) $B_1$ is a radical of formula (C″) and the moiety —$NR^aR^b$ has the formula ($M^1$), then the moiety ($L_1$) in the formula (C″) is other than —S—$CH_2$—, —S—($CH_2$)$_2$— or —S—CH($CH_3$)—, being the S atom attached to the pyrazolopyrimidinone moiety and the hydrocarbon part of —S—$CH_2$—, —S—($CH_2$)$_2$— or —S—CH($CH_3$)— attached to the —C(=O)$NR^aR^b$ moiety;

when in a compound of formula (I) $B_1$ is a radical of formula (C″) and the moiety —$NR^aR^b$ has the formula ($M^4$), then the pyridine group in ($M^4$) is other than 3-methylpyridin-2-ylamino-, 4-methylpyridin-2-ylamino-, 5-methylpyridin-2-ylamino-, 6-methylpyridin-2-ylamino-, 5-chloropyridin-2-ylamino-, or 5-bromopyridin-2-ylamino-; and when in a compound of formula (I) $B_1$ is a radical of formula (C″) and the moiety —$NR^aR^b$ has the formula ($M^4$), then $R_1$ is other than phenyl or substituted phenyl.

The compounds of the following list, which are encompassed in the definition of a compound of formula (I) wherein $B_1$ is a radical of formula (C″) and the moiety —$NR^aR^b$ has the formula ($M^1$), are cited in the Scifinder database but do not have any associated bibliographic reference:

2-[(4,5-dihydro-4-oxo-1Hpyrazolo[3,4-d]pyrimidin-6-yl)thio]-N-[(methylamino)carbonyl]-propanamide (CAS-RN: 1031193-67-5); N-(ethylcarbamoyl)-2-[(4-oxo-1-phenyl-5H-pyrazolo[3,4-d]pyrimidin-6-yl)sulfanyl]

acetamide (CAS-RN: 1324932-36-6); 2-[(4-oxo-1-phenyl-5H-pyrazolo[3,4-d]pyrimidin-6-yl)sulfanyl]-N-(propylcarbamoyl)acetamide (CAS-RN: 1327261-99-3); 2-[(4,5-dihydro-4-oxo-1-phenyl-1Hpyrazolo[3,4-d]pyrimidin-6-yl)thio]-N-[[(1-ethylethyl)amino]carbonyl]-acetamide (CAS-RN: 923917-56-0); 2-[(4,5-dihydro-4-oxo-1-phenyl-1H-pyrazolo[3,4-d]pyrimidin-6-yl)thio]-N-[(methylamino)carbonyl]-propanamide (CAS-RN: 924088-81-3); 2-[(4,5-dihydro-4-oxo-1-phenyl-1H-pyrazolo[3,4-d]pyrimidin-6-yl)thio]-N-[(ethylamino)carbonyl]-propanamide (CAS-RN: 924019-71-6); 2-[(4,5-dihydro-4-oxo-1-phenyl-1Hpyrazolo[3,4-d]pyrimidin-6-yl)thio]-N-[(2-propen-1-ylamino)carbonyl]-acetamide (CAS-RN: 924124-19-6); 2-[(4,5-dihydro-4-oxo-1-phenyl-1Hpyrazolo[3,4-d]pyrimidin-6-yl)thio]-N-[[(2-methylpropyl)amino]carbonyl]-acetamide (CAS-RN: 923913-11-5); N-(butylcarbamoyl)-2-[(4-oxo-1-phenyl-5H-pyrazolo[3,4-d]pyrimidin-6-yl)sulfanyl]acetamide (CAS-RN: 1297095-41-0); N-(tert-butylcarbamoyl)-2-[(4-oxo-1-phenyl-5H-pyrazolo[3,4-d]pyrimidin-6-yl)sulfanyl]acetamide (CAS-RN: 1323968-79-1); N-(isopentylcarbamoyl)-2-[(4-oxo-1-phenyl-5H-pyrazolo[3,4-d]pyrimidin-6-yl)sulfanyl]acetamide (CAS-RN: 1323753-25-8); 2-[(4,5-dihydro-4-oxo-1-phenyl-1H-pyrazolo[3,4-d]pyrimidin-6-yl)thio]-N-[[(1,1-dimethylethyl)amino]carbonyl]-propanamide; (CAS-RN: 1036673-46-7); 2-[[1-(3-chlorophenyl)-4,5-dihydro-4-oxo-1H-pyrazolo[3,4-d]pyrimidin-6-yl]thio]-N-[(ethylamino)carbonyl]-acetamide (CAS-RN: 1015980-86-5); 2-[[1-(3-chlorophenyl)-4,5-dihydro-4-oxo-1H-pyrazolo[3,4-d]pyrimidin-6-yl]thio]-N-[[(1-methylethyl)amino]carbonyl]-acetamide (CAS-RN: 1015637-99-6); 2-[[1-(3-chlorophenyl)-4,5-dihydro-4-oxo-1H-pyrazolo[3,4-d]pyrimidin-6-yl]thio]-N-[(methylamino)carbonyl]-propanamide; (CAS-RN: 1015638-71-7); 2-[[1-(3-chlorophenyl)-4,5-dihydro-4-oxo-1H-pyrazolo[3,4-d]pyrimidin-6-yl]thio]-N-[(propylamino)carbonyl]-acetamide; (CAS-RN: 1015980-98-9); 2-[[1-(3-chlorophenyl)-4,5-dihydro-4-oxo-1H-pyrazolo[3,4-d]pyrimidin-6-yl]thio]-N-[(ethylamino)carbonyl]-propanamide; (CAS-RN: 1016059-67-8); 2-[[1-(3-chlorophenyl)-4,5-dihydro-4-oxo-1H-pyrazolo[3,4-d]pyrimidin-6-yl]thio]-N-[[(2-methylpropyl)amino]carbonyl]-acetamide (CAS-RN: 1016059-70-3; 2-[[1-(3-chlorophenyl)-4,5-dihydro-4-oxo-1H-pyrazolo[3,4-d]pyrimidin-6-yl]thio]-N-[[(1-methylethyl)amino]carbonyl]-propanamide (CAS-RN: 1017177-19-3); 2-[[1-(3-chlorophenyl)-4,5-dihydro-4-oxo-1H-pyrazolo[3,4-d]pyrimidin-6-yl]thio]-N-[[(3-methylbutyl)amino]carbonyl]-acetamide (CAS-RN: 1015375-73-1); N-(methylcarbamoyl)-2-[(4-oxo-1-phenyl-5H-pyrazolo[3,4-d]pyrimidin-6-yl)sulfanyl]acetamide (CAS-RN: 1327380-12-0); N-(cyclohexylcarbamoyl)-2-[(4-oxo-1-phenyl-5H-pyrazolo[3,4-d]pyrimidin-6-yl)sulfanyl]propanamide (CAS-RN: 1090694-76-0); N-(cyclohexylcarbamoyl)-2-[(4-oxo-1-phenyl-5H-pyrazolo[3,4-d]pyrimidin-6-yl)sulfanyl]acetamide (CAS-RN: 1090673-85-0); N-(cyclopentylcarbamoyl)-2-[(4-oxo-1-phenyl-5H-pyrazolo[3,4-d]pyrimidin-6-yl)sulfanyl]propanamide (CAS-RN: 1089529-44-1); 2-[[1-(3-chlorophenyl)-4-oxo-5H-pyrazolo[3,4-d]pyrimidin-6-yl]sulfanyl]-N-(cyclohexylcarbamoyl)-acetamide (CAS-RN: 1016059-46-3); 2-[[1-(3-chlorophenyl)-4-oxo-5H-pyrazolo[3,4-d]pyrimidin-6-yl]sulfanyl]-N-(cyclopentylcarbamoyl)acetamide (CAS-RN: 1015638-39-7); 2-[[1-(3-chlorophenyl)-4-oxo-5H-pyrazolo[3,4-d]pyrimidin-6-yl]sulfanyl]-N-(2-methoxyethylcarbamoyl)acetamide (CAS-RN: 1015376-05-2); N-(2-methoxyethylcarbamoyl)-2-[(4-oxo-1-phenyl-5H-pyrazolo[3,4-d]pyrimidin-6-yl)sulfanyl]acetamide (CAS-RN: 930908-62-6); N-(cyclopentylcarbamoyl)-2-[(4-oxo-1-phenyl-5H-pyrazolo[3,4-d]pyrimidin-6-yl)sulfanyl]acetamide (CAS-RN: 878940-69-3).

The compounds of the following list, which are encompassed in the definition of a compound of formula (I) wherein $B_1$ is a radical of formula (C''') and the moiety —$NR^aR^b$ has the formula ($M^4$), are cited in the Scifinder database but do not have any associated bibliographic reference:
3-[(4,5-dihydro-1-methyl-4-oxo-1H-pyrazolo[3,4-d]pyrimidin-6-yl)amino]-N-(5-methyl-2-pyridinyl)-propanamide (CAS-RN: 1376242-38-4); 1-(1-methyl-4-oxo-5H-pyrazolo[3,4-d]pyrimidin-6-yl)-N-(6-methyl-2-pyridyl)piperidine-4-carboxamide (CAS-RN: 1301341-34-3); N-(5-chloro-2-pyridinyl)-1-(4,5-dihydro-1-methyl-4-oxo-1Hpyrazolo[3,4-d]pyrimidin-6-yl)-4-piperidinecarboxamide (CAS-RN: 1296538-47-0); N-(5-bromo-2-pyridinyl)-1-(4,5-dihydro-1-methyl-4-oxo-1Hpyrazolo[3,4-d]pyrimidin-6-yl)-3-piperidinecarboxamide (CAS-RN: 1293797-49-5); N-(5-bromo-2-pyridinyl)-1-[1-(1,1-dimethylethyl)-4,5-dihydro-4-oxo-1H-pyrazolo[3,4-d]pyrimidin-6-yl]-4-piperidinecarboxamide (CAS-RN: 1289341-51-0); 1-(1-methyl-4-oxo-5H-pyrazolo[3,4-d]pyrimidin-6-yl)-N-(3-methyl-2-pyridyl)piperidine-3-carboxamide (CAS-RN: 1288667-45-7); 1-[1-(1,1-dimethylethyl)-4,5-dihydro-4-oxo-1Hpyrazolo[3,4-d]pyrimidin-6-yl]-N-(4-methyl-2-pyridinyl)-4-piperidinecarboxamide (CAS-RN: 1287617-32-6); N-[3-chloro-5-(trifluoromethyl)-2-pyridyl]-2-[(4-oxo-1-phenyl-5H-pyrazolo[3,4-d]pyrimidin-6-yl)sulfanyl]acetamide (CAS-RN: 1287091-89-7); N-(3,5-dichloro-4-methyl-2-pyridyl)-2-[(4-oxo-1-phenyl-5H-pyrazolo[3,4-d]pyrimidin-6-yl)sulfanyl]acetamide (CAS-RN: 1276295-92-1); N-(5-chloro-2-pyridinyl)-2-[(4,5-dihydro-4-oxo-1-phenyl-1H-pyrazolo[3,4-d]pyrimidin-6-yl)thio]-propanamide (CAS-RN: 1038095-75-8); and 4,5-dihydro-N-(4-methyl-2-pyridinyl)-4-oxo-1-phenyl-1H-pyrazolo[3,4-d]pyrimidine-6-propanamide (CAS-RN: 1016098-55-7).

The compounds of the following list, which are encompassed in the definition of a compound of formula (I) wherein $B_1$ is a radical of formula (C''') and the moiety —$NR^aR^b$ has the formula ($M^4$), are cited in WO2000/021926 as inhibitors of cyclin dependent kinases useful in the treatment of cancer or other proliferative diseases:
N-[4-[[4,5-dihydro-3-(1-methylcyclopropyl)-4-oxo-1-(2,4,6-trichlorophenyl)-1H-pyrazolo[3,4-d]pyrimidin-6-yl]methyl]-2-hydroxyphenyl]-N'-2-pyridinyl-urea (CAS-RN: 1100540-39-3); N-[4-[[4,5-dihydro-3-(1-methylcyclopropyl)-4-oxo-1-(2,4,6-trichlorophenyl)-1H-pyrazolo[3,4-d]pyrimidin-6-yl]methyl]phenyl]-N'-2-pyridinyl-urea (CAS-RN: 1100540-25-7); N-[4-[[4,5-dihydro-3-(1-methylcyclopropyl)-4-oxo-1-(2,4,6-trichlorophenyl)-1H-pyrazolo[3,4-d]pyrimidin-6-yl]methyl]-2-methoxyphenyl]-N'-2-pyridinyl-urea (CAS-RN: 1100539-29-4); N-[4-[[4,5-dihydro-3-(2-methylpropyl)-4-oxo-1-(2,4,6-trichlorophenyl)-1H-pyrazolo[3,4-d]pyrimidin-6-yl]methyl]phenyl]-N'-2-pyridinyl-urea (CAS-RN: 1100535-70-3); N-[4-[[4,5-dihydro-3-(2-methylpropyl)-4-oxo-1-(2,4,6-trichlorophenyl)-1H-pyrazolo[3,4-d]pyrimidin-6-yl]methyl]-2-hydroxyphenyl]-N'-2-pyridinyl-urea (CAS-RN: 1100535-37-2); N-[4-[[3-cyclobutyl-4,5-dihydro-4-oxo-1-(2,4,6-trichlorophenyl)-1H-pyrazolo[3,4-d]

pyrimidin-6-yl]methyl]phenyl]-N'-2-pyridinyl-urea (CAS-RN: 1100535-24-7); N-[4-[[4,5-dihydro-3-(2-methylpropyl)-4-oxo-1-(2,4,6-trichlorophenyl)-1H-pyrazolo[3,4-d]pyrimidin-6-yl]methyl]-2-methoxyphenyl]-N'-2-pyridinyl-urea (CAS-RN: 1100534-67-5); N-[4-[[3-cyclobutyl-4,5-dihydro-4-oxo-1-(2,4,6-trichlorophenyl)-1H-pyrazolo[3,4-d]pyrimidin-6-yl]methyl]-2-hydroxyphenyl]-N'-2-pyridinyl-urea (CAS-RN: 1100534-24-4); N-[4-[[3-cyclobutyl-4,5-dihydro-4-oxo-1-(2,4,6-trichlorophenyl)-1H-pyrazolo[3,4-d]pyrimidin-6-yl]methyl]-2-methoxyphenyl]-N'-2-pyridinyl-urea (CAS-RN: 1100533-35-4); N-[4-[[4,5-dihydro-3-(1-methylethyl)-4-oxo-1-(2,4,6-trichlorophenyl)-1H-pyrazolo[3,4-d]pyrimidin-6-yl]methyl]-2-methylphenyl]-N'-2-pyridinyl-urea (CAS-RN: 1100531-94-9); N-[4-[[1-(2-chloro-6-methylphenyl)-3-ethyl-4,5-dihydro-4-oxo-1H-pyrazolo[3,4-d]pyrimidin-6-yl]methyl]phenyl]-N'-2-pyridinyl-urea (CAS-RN: 1100530-61-7); N-[3-[[4,5-dihydro-3-(1-methylethyl)-4-oxo-1-(2,4,6-trichlorophenyl)-1H-pyrazolo[3,4-d]pyrimidin-6-yl]methyl]-2-methylphenyl]-N'-2-pyridinyl-urea (CAS-RN: 1100529-91-6); N-[4-[[1-(2-chloro-6-methylphenyl)-3-ethyl-4,5-dihydro-4-oxo-1H-pyrazolo[3,4-d]pyrimidin-6-yl]methyl]-2-methoxyphenyl]-N'-2-pyridinyl-urea (CAS-RN: 1100529-64-3); N-[4-[[1-(2-chloro-6-methylphenyl)-3-ethyl-4,5-dihydro-4-oxo-1H-pyrazolo[3,4-d]pyrimidin-6-yl]methyl]-2-hydroxyphenyl]-N'-2-pyridinyl-urea (CAS-RN: 1100529-43-8); N-[4-[[4,5-dihydro-3-(1-methylethyl)-4-oxo-1-(2,4,6-trichlorophenyl)-1H-pyrazolo[3,4-d]pyrimidin-6-yl]methyl]-3-methylphenyl]-N'-2-pyridinyl-urea (CAS-RN: 1100528-57-1); N-[4-[[1-(2-chloro-6-methylphenyl)-3-cyclopropyl-4,5-dihydro-4-oxo-1H-pyrazolo[3,4-d]pyrimidin-6-yl]methyl]-2-hydroxyphenyl]-N'-2-pyridinyl-urea (CAS-RN: 1100526-20-2); N-[4-[[1-(2-chloro-6-methylphenyl)-3-cyclopropyl-4,5-dihydro-4-oxo-1H-pyrazolo[3,4-d]pyrimidin-6-yl]methyl]phenyl]-N'-2-pyridinyl-urea (CAS-RN: 1100526-04-2); N-[4-[[3-ethyl-4,5-dihydro-4-oxo-1-(2,4,6-trichlorophenyl)-1H-pyrazolo[3,4-d]pyrimidin-6-yl]methyl]-2-hydroxyphenyl]-N'-2-pyridinyl-urea (CAS-RN: 1100525-23-2); N-[4-[[1-(2-chloro-6-methylphenyl)-3-cyclopropyl-4,5-dihydro-4-oxo-1H-pyrazolo[3,4-d]pyrimidin-6-yl]methyl]-2-methoxyphenyl]-N'-2-pyridinyl-urea (CAS-RN: 1100524-59-1); N-[4-[[3-ethyl-4,5-dihydro-4-oxo-1-(2,4,6-trichlorophenyl)-1H-pyrazolo[3,4-d]pyrimidin-6-yl]methyl]-2-methoxyphenyl]-N'-2-pyridinyl-urea (CAS-RN: 1100523-76-9); N-[4-[[1-(2-chloro-6-methylphenyl)-4,5-dihydro-3-(1-methylethyl)-4-oxo-1H-pyrazolo[3,4-d]pyrimidin-6-yl]methyl]phenyl]-N'-2-pyridinyl-urea (CAS-RN: 1100521-60-5); N-[4-[[3-cyclopropyl-4,5-dihydro-4-oxo-1-(2,4,6-trichlorophenyl)-1H-pyrazolo[3,4-d]pyrimidin-6-yl]methyl]-2-hydroxyphenyl]-N'-2-pyridinyl-urea (CAS-RN: 1100520-80-6); N-[4-[[3-cyclopropyl-4,5-dihydro-4-oxo-1-(2,4,6-trichlorophenyl)-1H-pyrazolo[3,4-d]pyrimidin-6-yl]methyl]phenyl]-N'-2-pyridinyl-urea (CAS-RN: 1100520-48-6); N-[4-[[3-cyclopropyl-4,5-dihydro-4-oxo-1-(2,4,6-trichlorophenyl)-1H-pyrazolo[3,4-d]pyrimidin-6-yl]methyl]-2-methoxyphenyl]-N'-2-pyridinyl-urea (CAS-RN: 1100520-25-9); N-[4-[[1-(2-chloro-6-methylphenyl)-4,5-dihydro-3-(1-methylethyl)-4-oxo-1H-pyrazolo[3,4-d]pyrimidin-6-yl]methyl]-2-methoxyphenyl]-N'-2-pyridinyl-urea (CAS-RN: 1100520-10-2); N-[4-[[1-(2-chloro-6-methylphenyl)-4,5-dihydro-3-(1-methylethyl)-4-oxo-1H-pyrazolo[3,4-d]pyrimidin-6-yl]methyl]-2-hydroxyphenyl]-N'-2-pyridinyl-urea (CAS-RN: 1100519-85-4); N-[4-[[3-ethyl-4,5-dihydro-4-oxo-1-(2,4,6-trichlorophenyl)-1H-pyrazolo[3,4-d]pyrimidin-6-yl]methyl]phenyl]-N'-2-pyridinyl-urea (CAS-RN: 264140-35-4); N-[4-[[4,5-dihydro-3-(1-methylethyl)-4-oxo-1-(2,4,6-trichlorophenyl)-1H-pyrazolo[3,4-d]pyrimidin-6-yl]methyl]phenyl]-N'-2-pyridinyl-urea (CAS-RN: 264140-08-1).

Another aspect of the invention relates to a pharmaceutical composition which comprises a therapeutically effective amount of a compound of formula (I) as defined above, together with one or more pharmaceutically acceptable excipients or carriers.

As previously described, the compounds of the invention are dual inhibitors of PDEs and HDACs and can be useful to improve cognition. Therefore, another aspect of the invention relates to a compound of formula (I) or a pharmaceutical composition comprising the compound of formula (I) as defined above, for use as a medicament.

Another aspect of the present invention relates to a compound of formula (I) or a pharmaceutical composition comprising the compound of formula (I) as defined above, for use in the treatment and/or prevention of diseases mediated by the dual inhibition of PDE and HDAC. Thus, this aspect relates to the use of a compound of formula (I) as defined above, for the preparation of a medicament for the treatment and/or prevention of diseases mediated by the dual inhibition of PDE and HDAC; and may also be formulated as a method for the treatment and/or prevention of diseases mediated by the dual inhibition of PDE and HDAC, which comprises administering a therapeutically effective amount of the previously defined compound of formula (I), and one or more pharmaceutical acceptable excipients or carriers, in a subject in need thereof, including a human.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The term "carbocyclic" ring system refers to a known ring system wherein all the ring members contain carbon atoms. The term "heterocyclic" ring system refers to a known ring system wherein one or more of the ring members, preferably 1, 2, 3, or 4 ring members, are selected from NH, N, O, and S, where chemically possible. The remaining ring members of the heterocyclic ring are independently selected from C, CH, CH$_2$, O, N, NH, and S. Unless otherwise specified, the "heterocyclic" ring system may be attached to the rest of the molecule through a C or a N atom of the ring system. Both the carbocyclic and heterocyclic rings can be saturated or partially unsaturated, and may be unsubstituted or substituted as described herein, being the substituents placed on any available position.

According to the present invention, the term "polycyclic" ring refers to a ring system which is formed by two, three or four rings which can be fused, bridged-fused, spiro-fused or can contain different types of fusion. For the purposes of the present invention, in "fused" rings the fusion occurs through one bond which is common to two adjoining rings; in "bridged-fused" rings the fusion occurs through a sequence of atoms (bridgehead) which is common to two rings; and in "spiro-fused" rings, the fusion occurs through only one atom (spiro atom), preferably a carbon atom, which is common to two adjoining rings (including bridged rings).

The term "heteroaromatic" ring refers to a known aromatic ring system, wherein one or more of the ring members, preferably 1, 2, 3, or 4 ring members, are selected from NH, N, O, and S, where chemically possible. The remaining ring members of the heteroaromatic ring are independently selected from C, CH, O, N, NH, and S. The heteroaromatic ring may be unsubstituted or substituted as described herein, being the substituents placed on any available position.

The term "known ring system" as used herein refers to a ring system which is chemically feasible and is known in the art and so intends to exclude those ring systems that are not chemically possible.

For the purposes of the present invention, in all saturated or partially unsaturated rings, one or two members of the rings are optionally C(=O) and/or C(=NH) and/or C[=N($C_1$-$C_4$)alkyl].

The term linear or branched, saturated or unsaturated ($C_1$-$C_n$)alkyl refers to a linear or branched hydrocarbon chain which contains from 1 to n carbon atoms. When the ($C_1$-$C_n$)alkyl is saturated it contains only single bonds. When the ($C_1$-$C_n$)alkyl is unsaturated it contains one or two double bonds and/or one or two triple bonds. The saturated or unsaturated ($C_1$-$C_n$)alkyl may be substituted or unsubstituted as described herein. Moreover, in any alkyl group one or two chain members selected from $CH_2$ or CH are optionally replaced by chain members independently selected from N, NR, O, C(=O), C(=O)NR, NRC(=O) and S; wherein R is as described herein. When in the present invention it is not specified whether the term ($C_1$-$C_n$)alkyl is saturated or unsaturated, the term ($C_1$-$C_n$)alkyl has to be understood as a saturated linear or branched hydrocarbon chain which contains from 1 to n carbon atoms. The above definitions apply also for O($C_1$-$C_n$)alkyl.

A halogen substituent means fluoro, chloro, bromo or iodo.

In the embodiments of the invention referring to the compounds of formula (I), where the substitution or unsubstitution of a certain group is not specified, e.g. either by indicating a certain substitution for that group or by indicating that the group is unsubstituted, it has to be understood that the possible substitution of this group is the one as in the definition of the formula (I).

"Protective group" (PG) refers to a grouping of atoms that when attached to a reactive group in a molecule masks, reduces or prevents that reactivity.

The expression "substituted with one or more" means that a group can be substituted with one or more, preferably with 1, 2, 3 or 4 substituents, provided that this group has enough positions susceptible of being substituted.

For the purposes of the invention, room temperature is 20-25° C.

As mentioned above, a first aspect of the invention relates to compounds of formula (I) or a pharmaceutically acceptable salts thereof. There is no limitation on the type of salt that can be used, provided that these are pharmaceutically acceptable when they are used for therapeutic purposes. The term "pharmaceutically acceptable salts", embraces salts commonly used to form alkali metal salts and to form addition salts of free acids or free bases.

The preparation of pharmaceutically acceptable salts of the compounds of formula (I) can be carried out by methods known in the art. For instance, they can be prepared from the parent compound, which contains a basic or acidic moiety, by conventional chemical methods. Generally, such salts are, for example, prepared by reacting the free acid or base forms of these compounds with a stoichiometric amount of the appropriate pharmaceutically acceptable base or acid in water or in an organic solvent or in a mixture of them. The compounds of formula (I) and their salts may differ in some physical properties but they are equivalent for the purposes of the present invention.

The compounds of the invention may be in crystalline form either as free solvation compounds or as solvates (e.g. hydrates) and it is intended that both forms are within the scope of the present invention. Methods of solvation are generally known within the art. In general, the solvated forms with pharmaceutically acceptable solvents such as water, ethanol and the like are equivalent to the unsolvated form for the purposes of the invention.

Some compounds of formula of the invention can have chiral centres that can give rise to various stereoisomers. As used herein, the term "stereoisomer" refers to all isomers of individual compounds that differ only in the orientation of their atoms in space. The term stereoisomer includes mirror image isomers (enantiomers), mixtures of mirror image isomers (racemates, racemic mixtures), geometric (cis/trans or syn/anti or E/Z) isomers, and isomers of compounds with more than one chiral center that are not mirror images of one another (diastereoisomers). The present invention relates to each of these stereoisomers and also mixtures thereof.

Diastereoisomers and enantiomers can be separated by conventional techniques such as chromatography or fractional crystallization. Optical isomers can be resolved by conventional techniques of optical resolution to give optically pure isomers. This resolution can be carried out on any chiral synthetic intermediates or on compounds of the invention. Optically pure isomers can also be individually obtained using enantiospecific synthesis.

The bicycle in the B1 moiety (A"), (B"), and (C") can exist as different tautomers, as shown below, which are to be considered equivalent for the purposes of the invention:

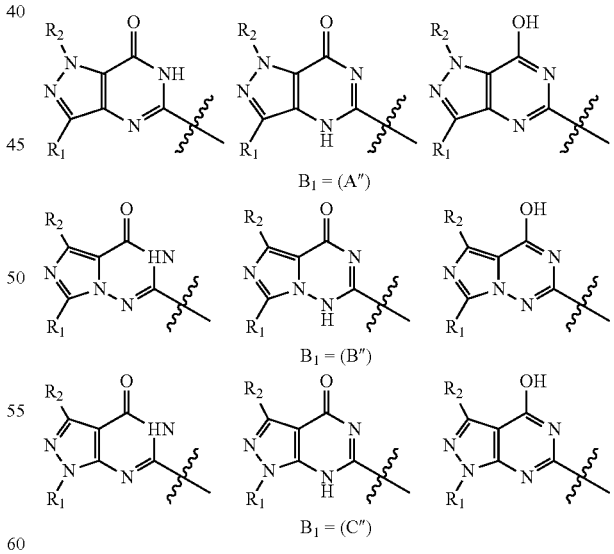

In all embodiments of the invention referring to the compounds of formula (I), the pharmaceutically acceptable salts thereof and the stereoisomers either of any of the compounds of formula (I) or of any of their pharmaceutically acceptable salts are always contemplated even if they are not specifically mentioned.

The compounds of formula (I) of the invention are characterized in that they have a polycyclic ring system selected from the group consisting of formula (A'), formula (B'), formula (C'), and formula (D'):

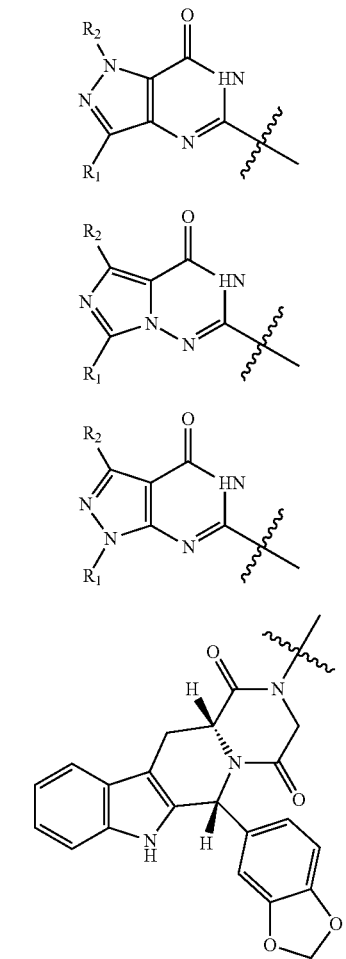

and a —(C=O)NR$^a$R$^b$ moiety. This polycyclic ring system comprises from 2 to 4 rings; being at least one ring an aromatic ring; and comprises at least 3 nitrogen atoms and 1 oxygen atom. The linker between the polycyclic ring system defined above and the —(C=O)NR$^a$R$^b$ moiety, i.e. a structure of formula (L$_1$) or (L$_2$),

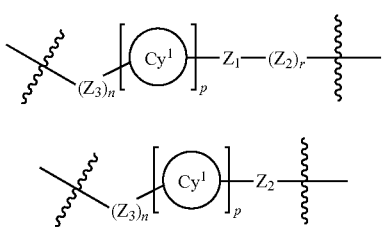

has a chain length comprised from 1 to 20 atoms and comprises a hydrocarbon chain, wherein one or more carbon atoms are optionally replaced by nitrogen, sulphur and/or oxygen atoms, which optionally contains one or more aromatic, heteroaromatic, carbocyclic and/or heterocyclic rings.

In a particular embodiment, the linker between the polycyclic ring system and the —(C=O)NR$^a$R$^b$ moiety is a structure of formula (L$_1$') or (L$_2$')

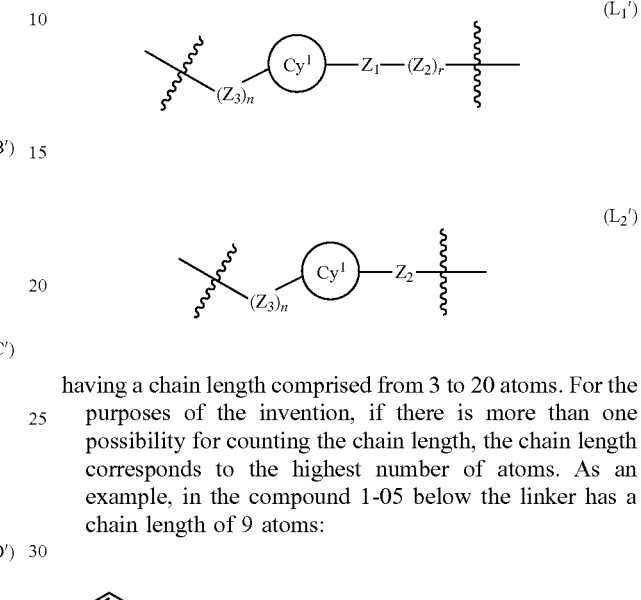

having a chain length comprised from 3 to 20 atoms. For the purposes of the invention, if there is more than one possibility for counting the chain length, the chain length corresponds to the highest number of atoms. As an example, in the compound 1-05 below the linker has a chain length of 9 atoms:

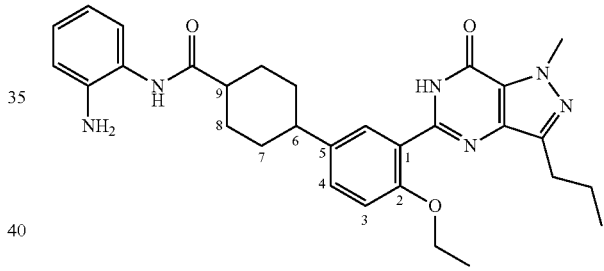

In one particular embodiment, optionally in combination with one or more features of the various embodiments described above or below, the invention relates to a compound of formula (I), wherein the moiety —NR$^a$R$^b$ has the formula (M$^3$)

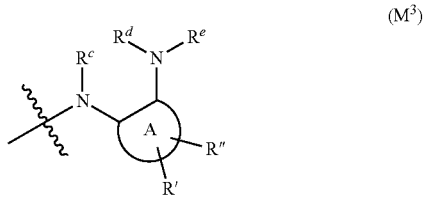

wherein R$^c$, R$^d$, R$^e$, A, R' and R" are as previously defined.

In another particular embodiment, optionally in combination with one or more features of the various embodiments described above or below, the invention relates to a compound of formula (I), wherein the moiety —NR$^a$R$^b$ is selected from the formula (M$^{3'}$) and formula (M$^{3''}$), more particularly the moiety —NR$^a$R$^b$ has the formula (M$^{3'}$):

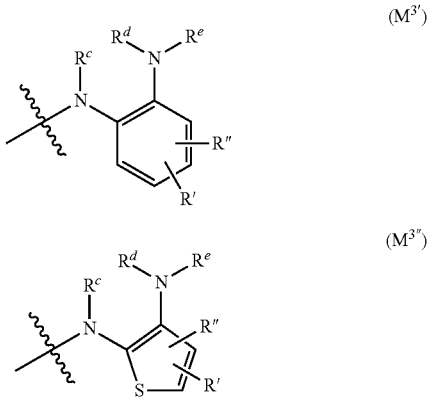

wherein $R^c$, $R^d$, $R^e$, R' and R" are as previously defined.

In another particular embodiment, optionally in combination with one or more features of the various embodiments described above or below, in a moiety of formula ($M^3$), formula ($M^{3'}$) or formula ($M^{3''}$), $R^c$, $R^d$, $R^e$ and R' are H, and R" is selected from the group consisting of H, halogen, and 5- or 6-membered heteroaromatic ring.

In another particular embodiment, optionally in combination with one or more features of the various embodiments described above or below, in a moiety of formula ($M^3$), formula ($M^{3'}$) or formula ($M^{3''}$), $R^d$ and $R^e$ are H.

In another particular embodiment, optionally in combination with one or more features of the various embodiments described above or below, the invention relates to a compound of formula (I), wherein the moiety —$NR^aR^b$ has the formula ($M^4$)

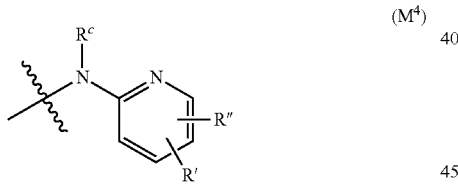

wherein $R^c$, R' and R" are as previously defined, with the condition that: when $B_1$ is a radical of formula (C"), then: the pyridine group in ($M^4$) is other than 3-methylpyridin-2-ylamino-, 4-methylpyridin-2-ylamino-, 5-methylpyridin-2-ylamino-, 6-methylpyridin-2-ylamino-, 5-chloropyridin-2-ylamino-, 5-bromopyridin-2-ylamino-; and $R_1$ is other than phenyl or substituted phenyl.

In another particular embodiment, optionally in combination with one or more features of the various embodiments described above or below, in a moiety of formula ($M^4$), R' and R" are H; with the condition that: when $B_1$ is a radical of formula (C"), then: $R_1$ is other than phenyl or substituted phenyl.

In one particular embodiment, optionally in combination with one or more features of the various embodiments described above or below, the invention relates to a compound of formula (I), wherein the moiety —$NR^aR^b$ has the formula ($M^1$)

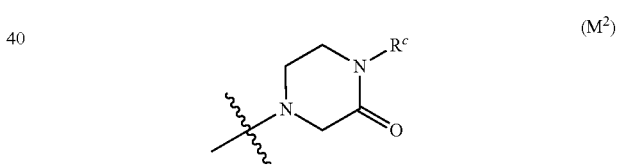

wherein $R^c$, $R^d$, and $R^e$ are as previously defined; with the condition than when in a compound of formula (I) $B_1$ is a radical of formula (C"), then the moiety ($L_1$) in the formula (C") is other than —S—$CH_2$—, —S—$(CH_2)_2$— or —S—$CH(CH_3)$—, being the S atom attached to the pyrazolopyrimidinone moiety and the hydrocarbon part of —S—$CH_2$—, —S—$(CH_2)_2$— or —S—$CH(CH_3)$— attached to the —C(=O)$NR^aR^b$ moiety.

In another particular embodiment, optionally in combination with one or more features of the various embodiments described above or below, in a moiety of formula ($M^1$), $R^c$ is hydrogen; and $R^d$ and $R^e$ are independently selected from H, —($C_1$-$C_7$)alkyl optionally substituted with one or more halogen atoms; more particularly, $R^c$ and $R^d$ are hydrogen; and $R^e$ is independently selected from H, —($C_1$-$C_7$)alkyl optionally substituted with one or more halogen atoms; with the condition than when in a compound of formula (I) $B_1$ is a radical of formula (C"), then the moiety ($L_1$) in the formula (C") is other than —S—$CH_2$—, —S—$(CH_2)_2$— or —S—$CH(CH_3)$—, being the S atom attached to the pyrazolopyrimidinone moiety and the hydrocarbon part of —S—$CH_2$—, —S—$(CH_2)_2$— or —S—$CH(CH_3)$— attached to the —C(=O)$NR^aR^b$ moiety.

In one particular embodiment, optionally in combination with one or more features of the various embodiments described above or below, the invention relates to a compound of formula (I), wherein the moiety —$NR^aR^b$ has the formula ($M^2$)

wherein $R^c$ is as previously defined.

In another particular embodiment, optionally in combination with one or more features of the various embodiments described above or below, the invention relates to a compound of formula (I), wherein $B_1$ is a radical of formula (A").

In another particular embodiment, optionally in combination with one or more features of the various embodiments described above or below, the invention relates to a compound of formula (I), wherein $B_1$ is a radical of formula (B").

In another particular embodiment, optionally in combination with one or more features of the various embodiments described above or below, the invention relates to a compound of formula (I), wherein $B_1$ is a radical of formula (C").

In another particular embodiment, optionally in combination with one or more features of the various embodiments described above or below, the invention relates to a compound of formula (I), wherein $R_1$ is selected from the group consisting of saturated or unsaturated ($C_1$-$C_4$)alkyl optionally substituted with one or more halogen atoms, 5- to 6-membered saturated carbocyclic ring optionally substituted with one or more substituents selected from halogen and $(C_1-C_3)$alkyl, and 5- to 6-membered saturated heterocyclic ring optionally substituted with one or more substituents selected from halogen and $(C_1-C_3)$alkyl.

In another particular embodiment, optionally in combination with one or more features of the various embodiments described above or below, the invention relates to a compound of formula (I), wherein $R_2$ is H or saturated or unsaturated $(C_1-C_4)$alkyl optionally substituted with one or more halogen atoms.

In another particular embodiment, optionally in combination with one or more features of the various embodiments described above or below, the invention relates to a compound of formula (I), wherein $Z_1$ is a biradical selected from the group consisting of a formula (E), formula (F''), and formula (H'):

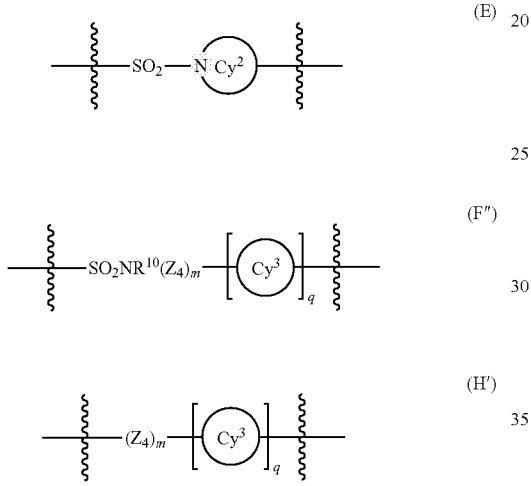

wherein $Cy^2$, $R^{10}$, $Z_4$, m, $Cy^3$, and q are as previously defined, more particularly, wherein q is 1.

In another particular embodiment, optionally in combination with one or more features of the various embodiments described above or below, the invention relates to a compound of formula (I), wherein r is 0, or alternatively r is 1 and $Z_2$ is -$Cy^4$-; more particularly, wherein r is 0.

In another particular embodiment, optionally in combination with one or more features of the various embodiments described above or below, the invention relates to a compound of formula (I), wherein $B_1$ is a radical of formula (D'').

In another particular embodiment, optionally in combination with one or more features of the various embodiments described above or below, the invention relates to a compound of formula (I), wherein p is 1; more particularly, wherein $Cy^1$ is phenyl or a 3- to 7-membered carbocyclic or heterocyclic monocyclic ring, which is saturated or partially unsaturated or aromatic, and wherein $Cy^1$ is optionally substituted with one or more $R_3$ groups.

In another particular embodiment, optionally in combination with one or more features of the various embodiments described above or below, the invention relates to a compound of formula (I), wherein p is 1; more particularly, wherein $Cy^1$ is selected from the group consisting of: phenyl, 5- to 6-membered heteroaromatic ring, and 4- to 6-membered saturated heterocyclic ring, wherein $Cy^1$ is optionally substituted with one or more $R_3$ groups.

In another particular embodiment, optionally in combination with one or more features of the various embodiments described above or below, the invention relates to a compound of formula (I), which is a compound of formula (IA):

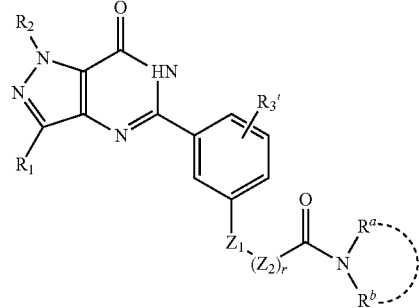

wherein $R_3'$ is H or $R_3$, and $R_1$, $R_2$, $R_3$, $Z_1$, $Z_2$, r, the dashed line, and the moiety $NR^aR^b$ are as previously defined.
More particularly, in the compound of formula (IA), the moiety —$NR^aR^b$ is selected from the formula ($M^{3'}$) and formula ($M^{3''}$) as previously defined, more particularly, it has the formula ($M^{3'}$).

In another particular embodiment, optionally in combination with one or more features of the various embodiments described above or below, the invention relates to a compound of formula (I), which is a compound of formula (IB):

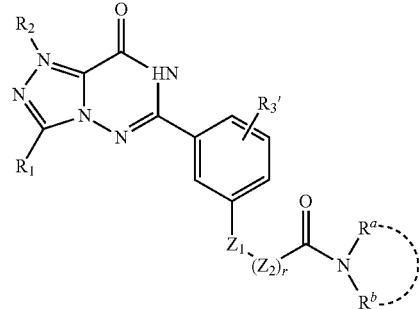

wherein $R_3'$ is H or $R_3$, and $R_1$, $R_2$, $R_3$, $Z_1$, $Z_2$, r, the dashed line, and the moiety $NR^aR^b$ are as previously defined.
More particularly, in the compound of formula (IB), the moiety —$NR^aR^b$ is selected from the formula ($M^{3'}$) and formula ($M^{3''}$) as previously defined, more particularly, it has the formula ($M^{3'}$).

In another particular embodiment, optionally in combination with one or more features of the various embodiments described above or below, the invention relates to a compound of formula (I), in particular a compound of formula (IA) or a compound of formula (IB), wherein $R_3'$ is selected from H, halogen, saturated or unsaturated $(C_1-C_4)$alkyl optionally substituted with one or more halogen atoms; and saturated or unsaturated —$O(C_1-C_4)$alkyl optionally substituted with one or more halogen atoms.

In another particular embodiment, optionally in combination with one or more features of the various embodiments described above or below, the invention relates to a compound of formula (I), which is a compound of formula (IC):

(IC)

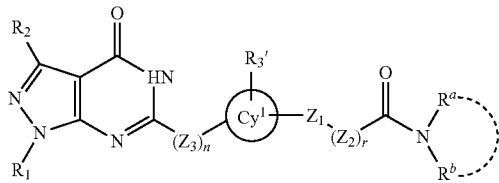

wherein $R_3'$ is H or $R_3$, and $R_1$, $R_2$, $R_3$, $Z_1$, $Z_2$, $Z_3$, n, r, the dashed line, and the moiety $NR^aR^b$ are as previously defined. More particularly, in the compound of formula (IC), the moiety —$NR^aR^b$ is selected from the formula (M$^{3'}$) and formula (M$^{3''}$) as previously defined, more particularly, it has the formula (M$^{3'}$).

In another particular embodiment, optionally in combination with one or more features of the various embodiments described above or below, the invention relates to a compound of formula (I), which is a compound of formula (IC$^{III}$) or (IC$^{III}$)

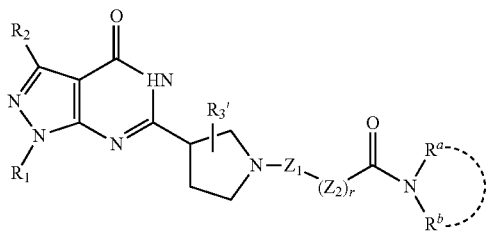

(IC$^{IV}$)

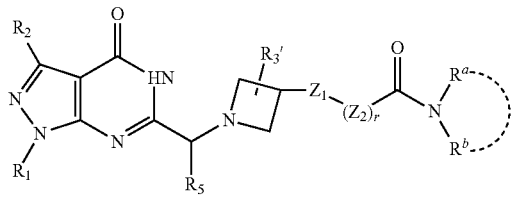

a compound of formula (IC$^{IV}$):
wherein $R_5$ is selected from the group consisting of: H, halogen, and (C$_1$-C$_4$)alkyl optionally substituted with one or more halogen atoms; and $R_1$, $R_2$, $R_3'$, $Z_1$, $Z_2$, $Z_3$, r, the dashed line, and the moiety $NR^aR^b$ are as previously defined. More particularly, in the compound of formula (IC$^{III}$) or formula (IC$^{IV}$), the moiety —$NR^aR^b$ is selected from the formula (M$^{3'}$) and formula (M$^{3''}$) as previously defined, more particularly, it has the formula (M$^{3'}$).

In another particular embodiment, optionally in combination with one or more features of the various embodiments described above or below, the invention relates to a compound of formula (I), in particular a compound of formula (IC), a compound of formula (IC$^{III}$) or a compound of formula (IC$^{IV}$), wherein $R_3'$ is selected from H and saturated or unsaturated (C$_1$-C$_4$)alkyl optionally substituted with one or more halogen atoms.

In another particular embodiment, optionally in combination with one or more features of the various embodiments described above or below, the invention relates to a compound of formula (I), which is a compound of formula (ID):

(ID)

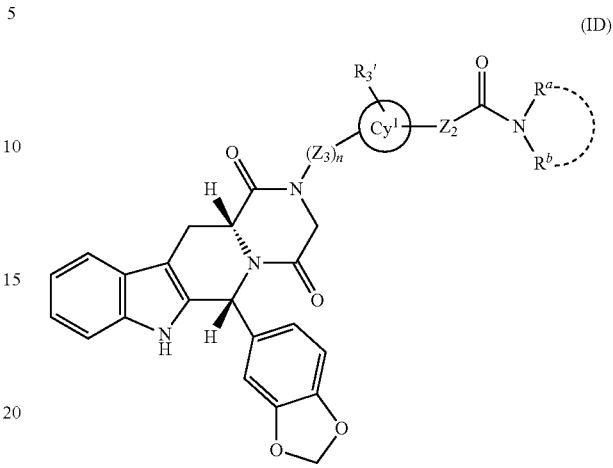

wherein $R_3'$ is H or $R_3$, and $Z_2$, $Z_3$, n, Cy$^1$, the dashed line, and the moiety $NR^aR^b$ are as previously defined. More particularly, in the compound of formula (ID), the moiety —$NR^aR^b$ is selected from the formula (M$^{3'}$) and formula (M$^{3''}$) as previously defined, more particularly, it has the formula (M$^{3'}$).

In another particular embodiment, optionally in combination with one or more features of the various embodiments described above or below, the invention relates to a compound of formula (I), in particular a compound of formula (ID), wherein $R_3'$ is selected from H, halogen, and saturated or unsaturated (C$_1$-C$_4$)alkyl optionally substituted with one or more halogen atoms.

The inventors have found that compounds of formula (II) also comprising several ring systems and a —(C=O)NR$^a$R$^b$ moiety are also dual inhibitors of PDEs and HDACs. Thus, the present invention also relates to compounds of formula (II), including any stereoisomer or mixtures thereof, or pharmaceutically acceptable salts thereof, (II)

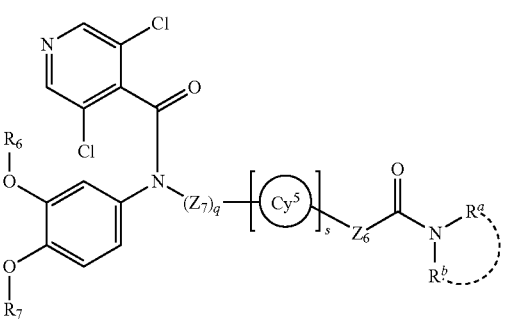

wherein
the moiety —NR$^a$R$^b$, wherein the dashed line means that R$^a$ and R$^b$ optionally form a known ring system, is selected from the group consisting of formula (M$^1$), formula (M$^2$), formula (M$^3$), and formula (M$^4$):

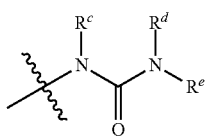

(M¹)

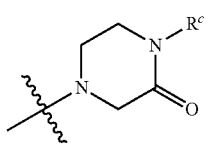

(M²)

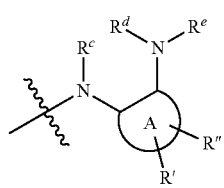

(M³)

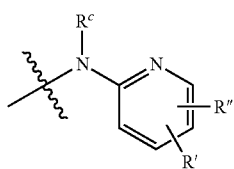

(M⁴)

R$^c$ is hydrogen;

R$^d$ and R$^e$ are independently selected from H, —(C$_1$-C$_7$) alkyl optionally substituted with one or more halogen atoms, and a known 3- to 8-membered carbocyclic monocyclic ring, saturated or partially unsaturated, which is optionally substituted with one or more halogen atoms;

A is a known ring system selected from phenyl and 5- to 6-membered heteroaromatic ring, wherein the substituents —NR$^c$— and —NR$^d$R$^e$ are attached to adjacent carbon atoms;

R' and R" are independently selected from the group consisting of H, R$^f$, phenyl optionally substituted with one or more substituents R$^f$, 5- or 6-membered heteroaromatic ring optionally substituted with one or more substituents R$^f$, and —(C$_1$-C$_7$)alkyl optionally substituted with one or more halogen atoms;

each R$^f$ is independently selected from halogen, —NO$_2$, —CN, —OR$^g$, —OC(O)R$^g$, —OC(O)OR$^g$, —OC(O) NR$^g$R$^g$, —NR$^g$R$^g$, —NR$^g$C(O)R$^g$, —NR$^g$C(O)OR$^g$, —NR$^g$C(O)NR$^g$R$^g$, —NR$^g$S(O)$_2$R$^g$, —NR$^g$SO$_2$NR$^g$R$^g$, —SR$^g$, —S(O)R$^g$, —SO$_2$R$^g$, —SO$_2$(OR$^g$), —SO$_2$NR$^g$R$^g$, —C(O)R$^g$, —C(O)OR$^g$, —C(O)NR$^g$R$^g$, and —C(O) NR$^g$OR$^g$;

each R$^g$ is independently selected from H, —(C$_1$-C$_4$)alkyl optionally substituted with one or more halogen atoms, and a known 3- to 7-membered carbocyclic monocyclic ring, saturated or partially unsaturated, which is optionally substituted with one or more halogen atoms;

q and s are independently 0 or 1;

R$_6$ and R$_7$ are independently selected from the group consisting of H; saturated or unsaturated (C$_1$-C$_6$)alkyl optionally substituted with one or more halogen atoms; and 3- to 6-membered carbocyclic or heterocyclic monocyclic ring containing from 1 to 3 ring members selected from NH, N, O, and S, which is saturated or partially unsaturated or aromatic, and which is optionally substituted with one or more R$_8$ groups;

Z$_6$ is selected from the group consisting of —Z$_8$—; —Z$_8$-Cy$^6$-; —Z$_8$—Cy$^6$-Z$_8$—; and -Cy$^7$-;

Z$_7$ and Z$_8$ are independently a biradical of a saturated or unsaturated (C$_1$-C$_6$)alkyl optionally substituted with one or more halogen atoms;

Cy$^5$ and Cy$^6$ are independently phenyl or a 4- to 6-membered carbocyclic or heterocyclic monocyclic ring; which is saturated or partially unsaturated or aromatic; and which is optionally substituted with one or more R$_8$ groups;

R$_8$ is selected from halogen, saturated or unsaturated (C$_1$-C$_4$)alkyl optionally substituted with one or more halogen atoms; and saturated or unsaturated —O(C$_1$-C$_4$)alkyl optionally substituted with one or more halogen atoms;

wherein in any heterocyclic ring one or more of the ring members are selected from NH, N, O, and S;

wherein in all saturated or partially unsaturated rings one or two members of the rings are optionally C(=O) and/or C(=NH) and/or C[=N(C$_1$-C$_4$)alkyl]; and wherein in any alkyl group one or two chain members selected from CH$_2$ or CH are optionally replaced by chain members independently selected from N, NR$_9$, O, C(=O), C(=O)NR$_9$, NR$_9$C(=O) and S; and R$_9$ is H or (C$_1$-C$_6$)alkyl optionally substituted with one or more halogen atoms;

wherein saturated alkyl refers to a linear or branched hydrocarbon chain which contains only single bonds; and unsaturated alkyl refers to a linear or branched hydrocarbon chain which contains one or two double bonds and/or one or two triple bonds;

with the condition that the moiety (L$_3$) of the formula (II)

(L$_3$)

has a chain length comprised from 1 to 20 atoms.

In a particular embodiment, in a compound of formula (II), the moiety —NR$^a$R$^b$ is selected from the formula (M$^{3'}$) and formula (M$^{3''}$) as previously defined, more particularly, it has the formula (M$^{3'}$).

In a particular embodiment, in a compound of formula (II), q is 0, s is 1, and Cy$^5$ is 3- to 6-membered carbocyclic ring or 3- to 6-membered heterocyclic ring, wherein Cy$^5$ is optionally substituted with one or more R$_8$ groups. In another embodiment, in a compound of formula (II), q is 0 and s is 0.

In another embodiment of the invention, the compound of formula (I) is selected from the group consisting of:

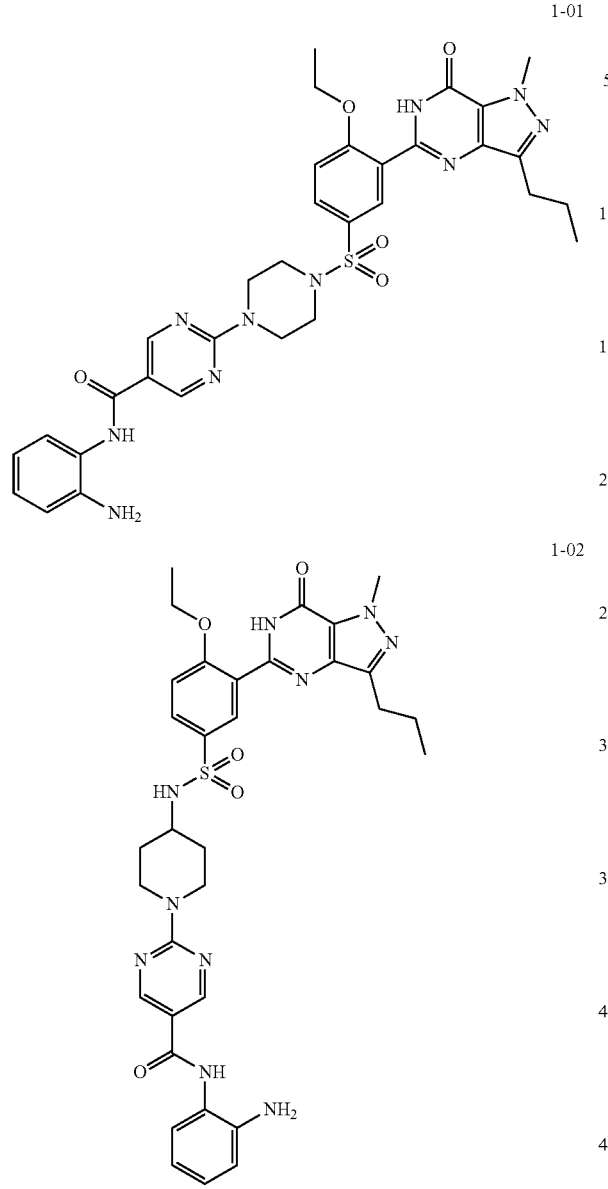
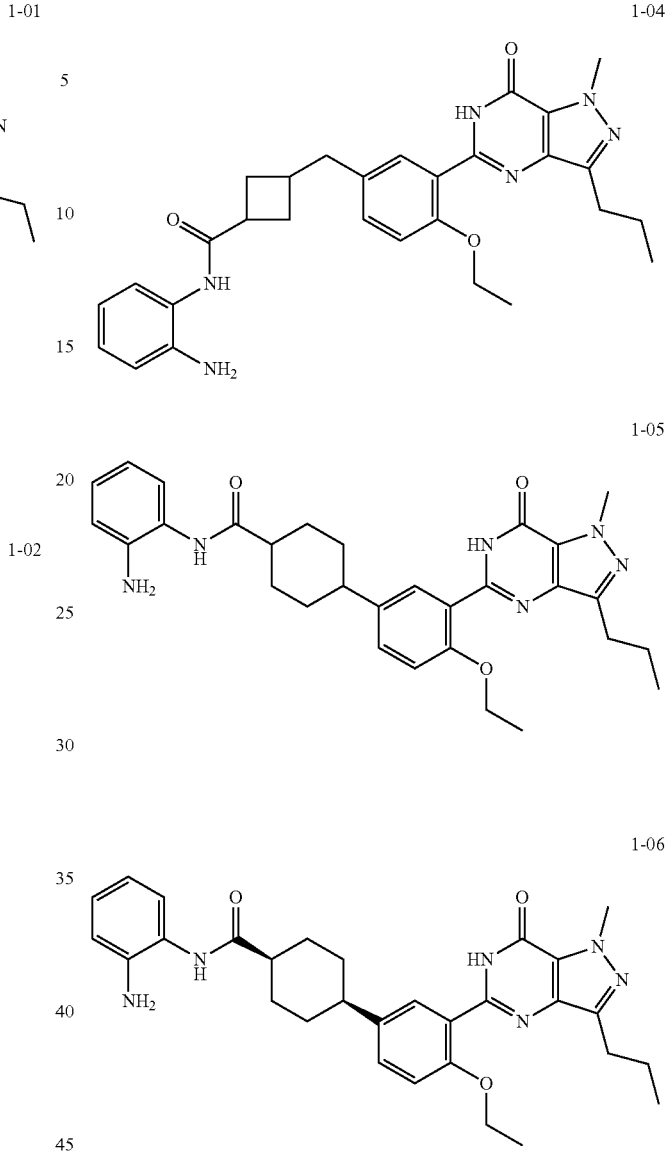
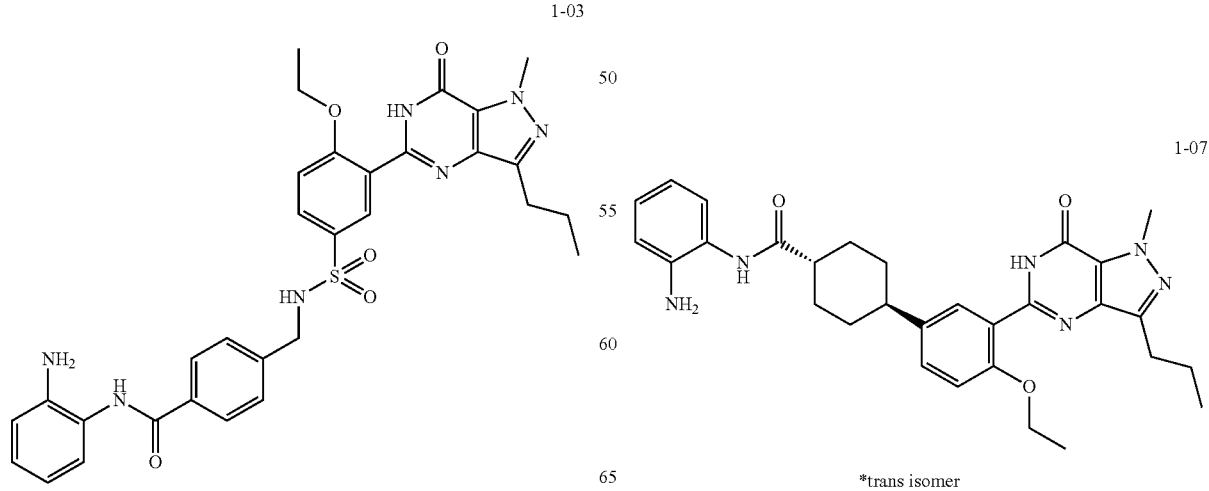
*cis isomer
*trans isomer

-continued
1-08
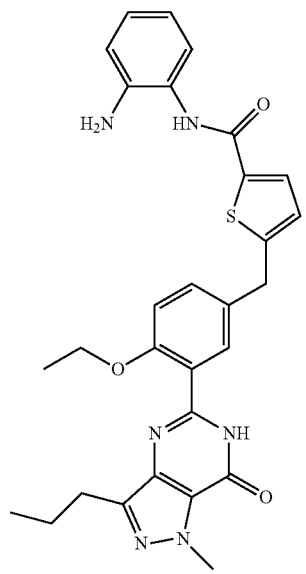
1-09
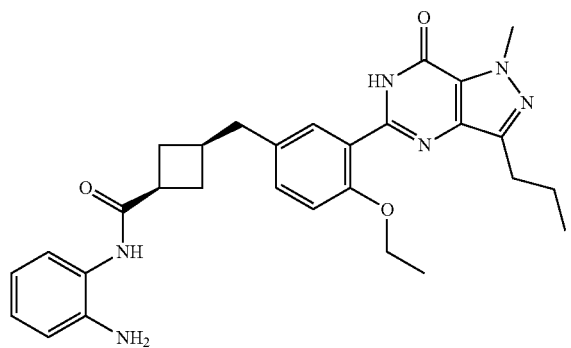
*cis isomer
1-10
*trans isomer
-continued
1-11
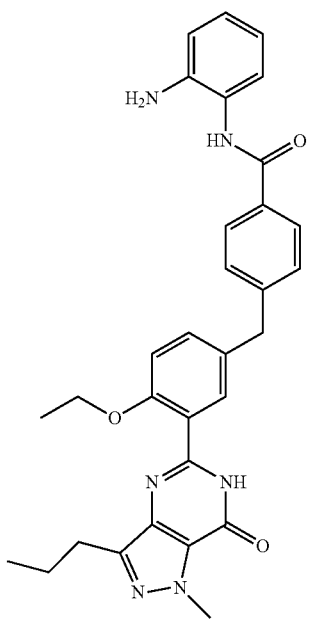
1-12
1-13
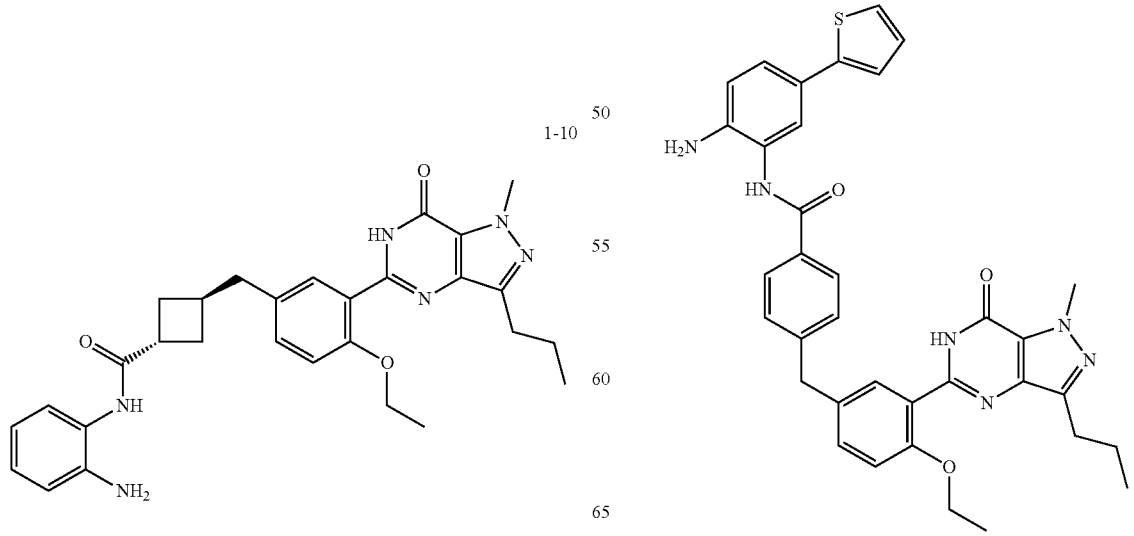

1-14
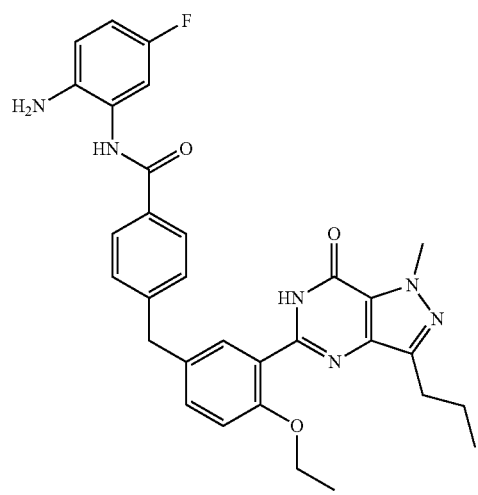

1-15
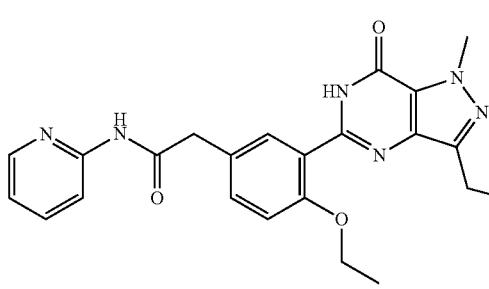

1-16
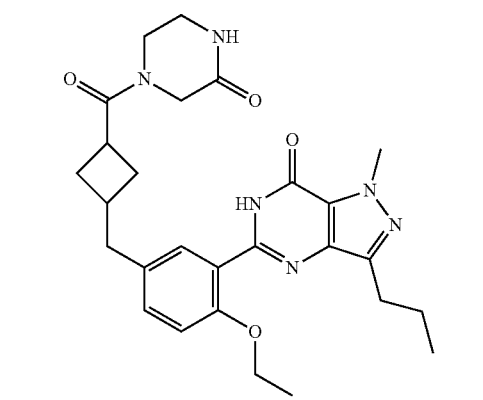

1-17
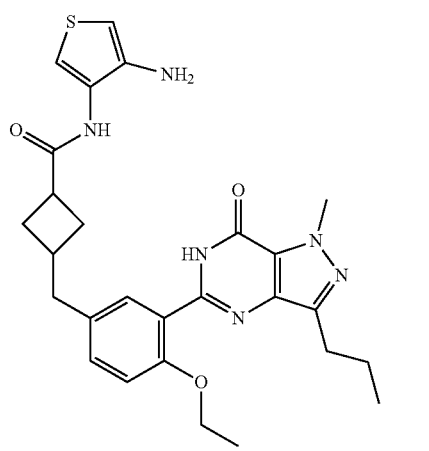

1-18
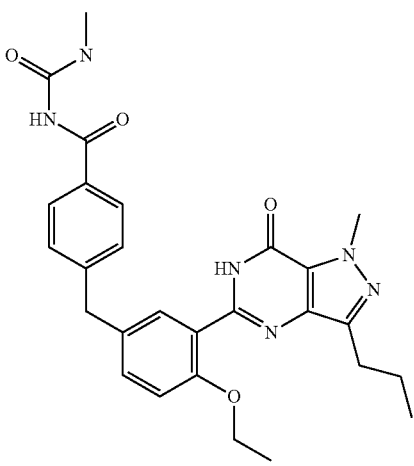

1-19
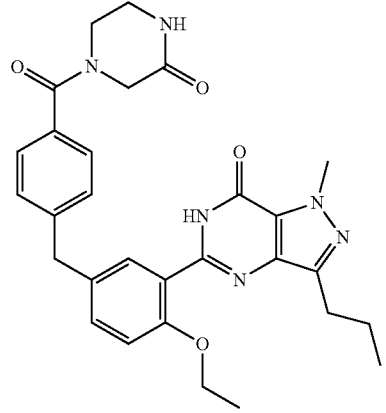

1-20
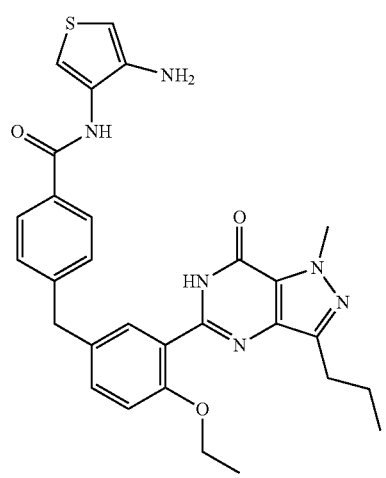

*Regarding these compounds, an aleatory absolute configuration of the cis and trans isomers is shown. In the examples it is clearly indicated which of the isomers is concerned in relative terms by differentiating unambiguously between cis and trans isomers by their physical and/or spectroscopic properties.

In another embodiment of the invention, the compound of formula (I) is selected from the group consisting of:

2-01
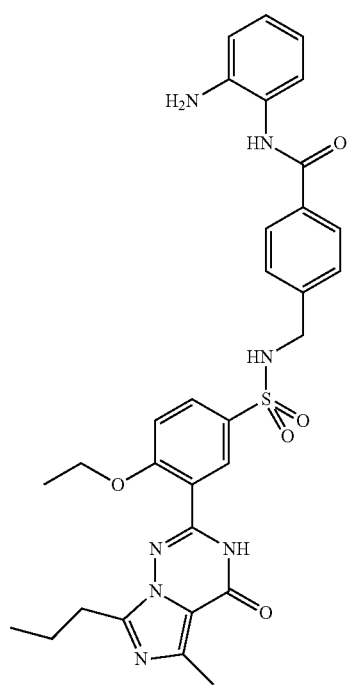
-continued
2-04
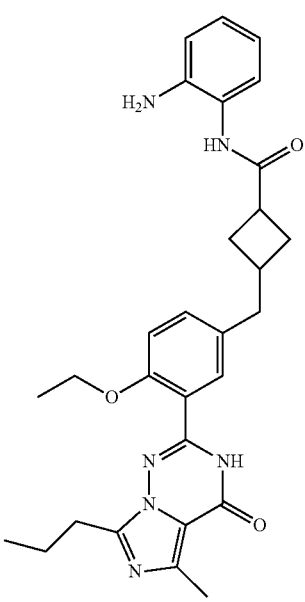
2-02
2-05
2-03
2-06
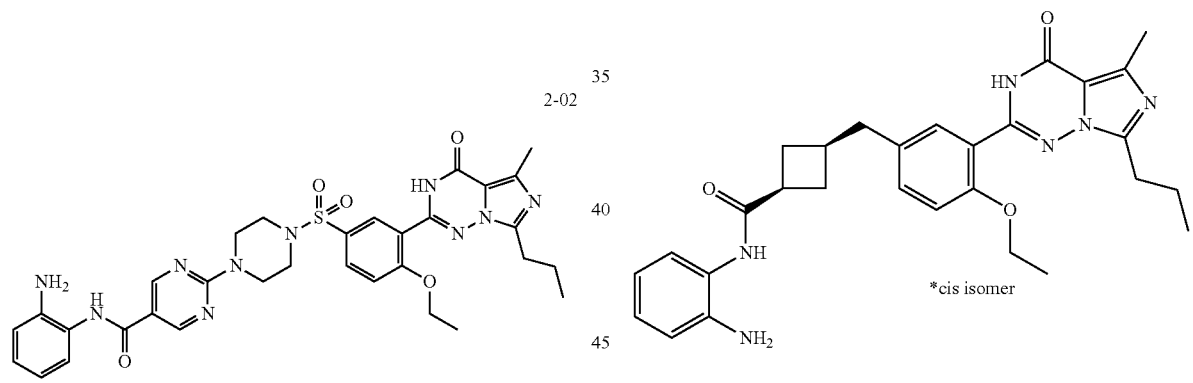
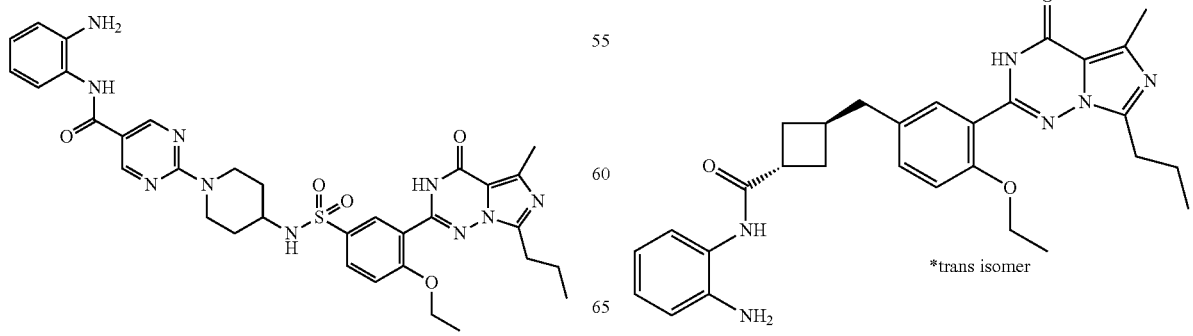
*cis isomer
*trans isomer 2-07

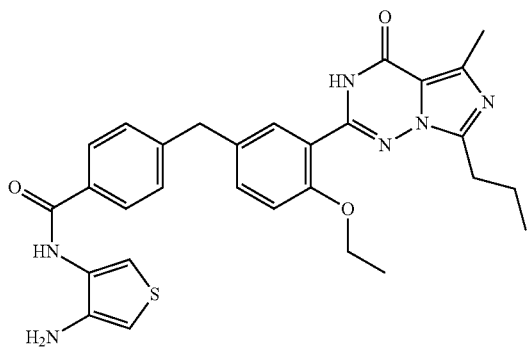

*Regarding these compounds, an aleatory absolute configuration of the cis and trans isomers is shown. In the examples it is clearly indicated which of the isomers is concerned in relative terms by differentiating unambiguously between cis and trans isomers by their physical and/or spectroscopic properties.

In another embodiment of the invention, the compound of formula (I) is selected from the group consisting of:

3-01

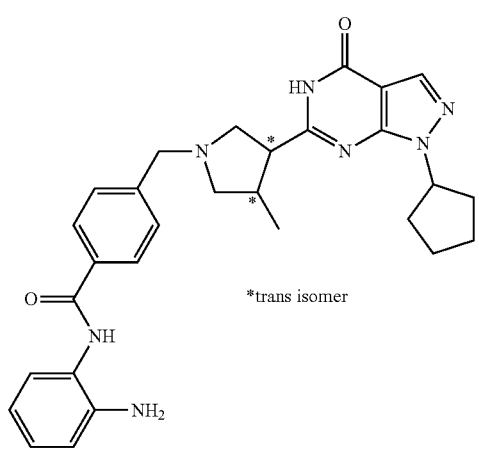

*trans isomer 3-02

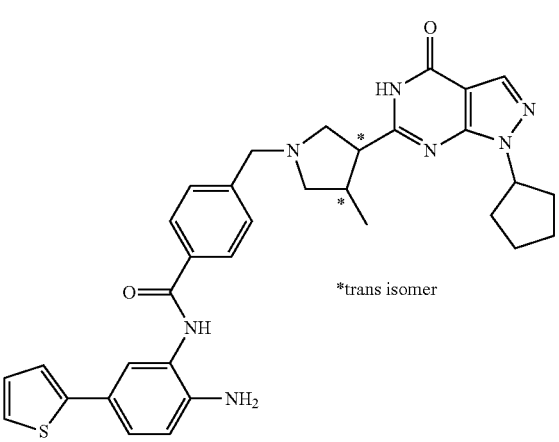

*trans isomer 3-03

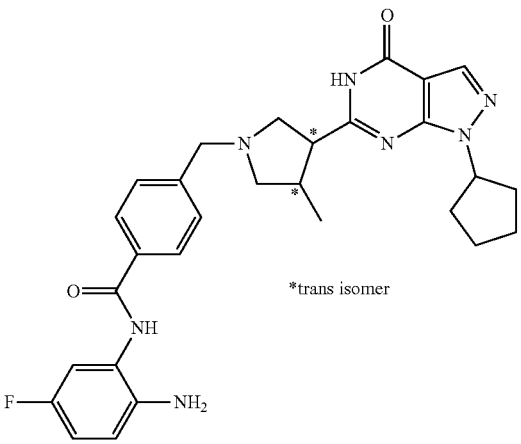

*trans isomer 3-04

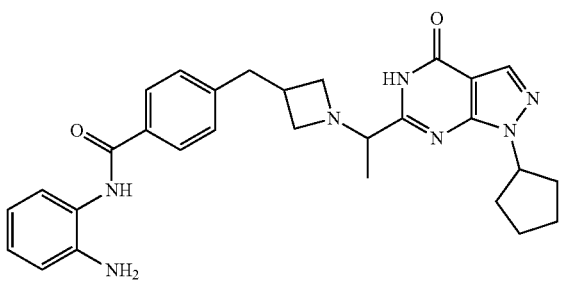

3-05

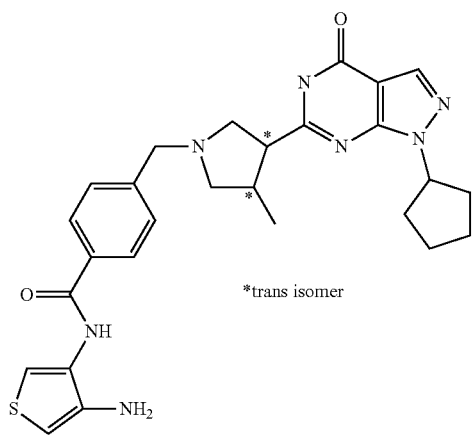

*trans isomer

In another embodiment of the invention, the compound of formula (I) is selected from the group consisting of:

4-01

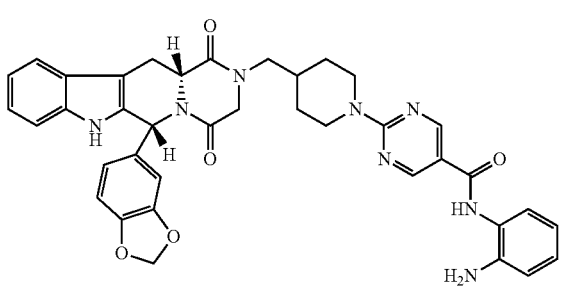

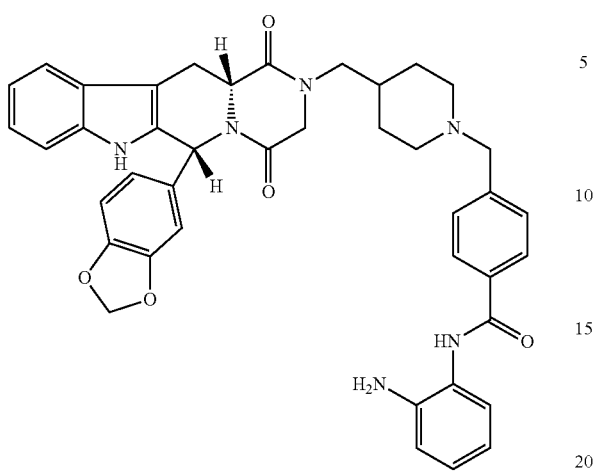

4-02

Generally, compounds of formula (I) as defined above wherein the moiety —NR$^a$R$^b$ is selected from the group consisting of (M$^1$), (M$^2$), (M$^3$) and (M$^4$) having the following formulas:

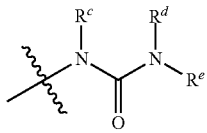

(M$^1$)

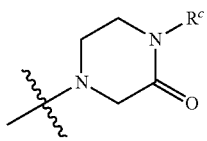

(M$^2$)

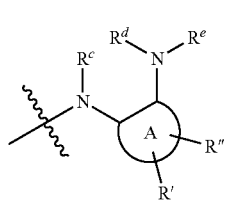

(M$^3$)

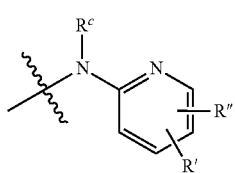

(M$^4$)

i.e. compounds of formula (IM$^1$), (IM$^2$), (IM$^3$), and (IM$^4$), respectively,

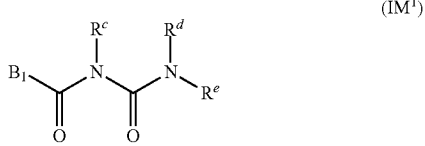

(IM$^1$)

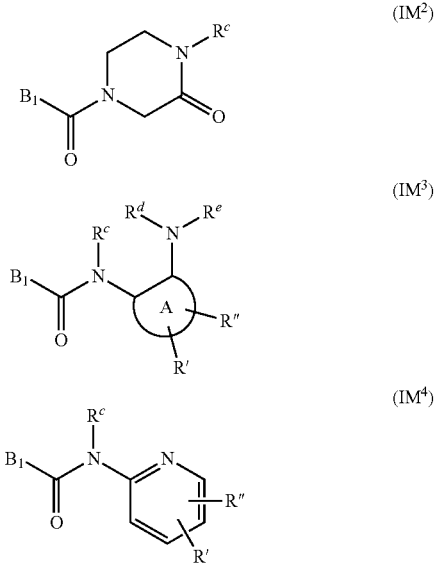

(IM$^2$)

(IM$^3$)

(IM$^4$)

may be obtained by reacting a compound of formula B$_1$—COOR' (IV), wherein B$_1$ is as previously defined and R' is H, with a suitable reagent of formula (XXII), (XXIII), (XXIV), and (XXV), respectively,

(XXII)

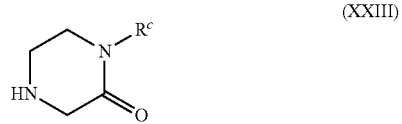

(XXIII)

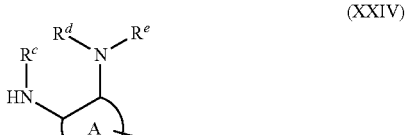

(XXIV)

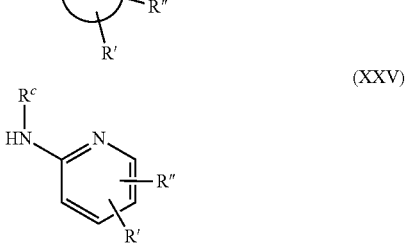

(XXV)

wherein R$^c$, R$^d$, R$^e$, A, R' and R" are as previously defined. These conversions may be carried out in the presence of an activating agent, such as 1-ethyl-3-(3-dimethylaminopropyl)carbodiimide hydrochloride (EDC.HCl) and hydroxybenzotriazole (HOBt), or pentafluorophenol (PFP) and N,N'-diisopropylcarbodiimide (DIC) in the presence of dimethylaminopyridine (DMAP), or (benzotriazol-1-yloxy)tris(dimethylamino)phosphonium hexafluorophosphate (BOP), preferably in the presence of a base, such as N-methylmorpholine (NMM) or N,N'- diisopropylethylamine (DIEA), in a suitable solvent, such as dichloromethane, chloroform or dimethylformamide, at a temperature comprised from room temperature to the temperature of the boiling point of the solvent.

Alternatively, a compound of formula (IM$^1$), (IM$^2$), (IM$^3$) and (IM$^4$) may be obtained by reacting a compound of formula $B_1$—COOR' (IV), wherein $B_1$ is as previously defined and R' is H, with (COCl)$_2$ in the presence of a suitable solvent, such as dichloromethane and dimethylformamide; and then reacting the acyl chloride intermediate with a suitable reagent of formula (XXII), (XXIII), (XXIV), or (XXV), respectively, in the presence of a base, such as triethylamine, and in a suitable solvent such as dichloromethane.

If necessary, amino groups present in the compounds of formula (XXII), (XXIII), (XXIV) or (XXV) other than the reacting amino groups, may be conveniently protected by a suitable protective group, and after reaction with the compound of formula $B_1$—COOR' (IV), they can be deprotected, to obtain the free amino groups.

Compounds of formula (IV) having the formula (IVa) or the formula (IVb):

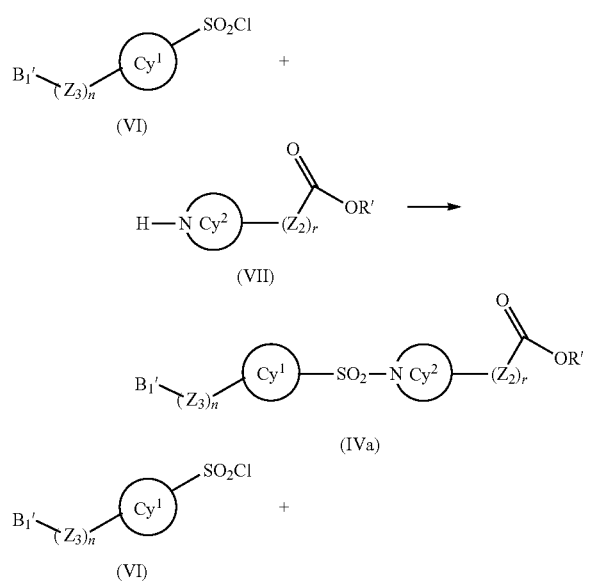

wherein $B_1'$, $Z_2$-$Z_4$, m, n, r, $Cy^1$-$Cy^3$ are as defined in the compounds of formula (I) and R' is a carboxy protective group, can be prepared by coupling a compound of formula (VI) with a compound of formula (VII) or a compound

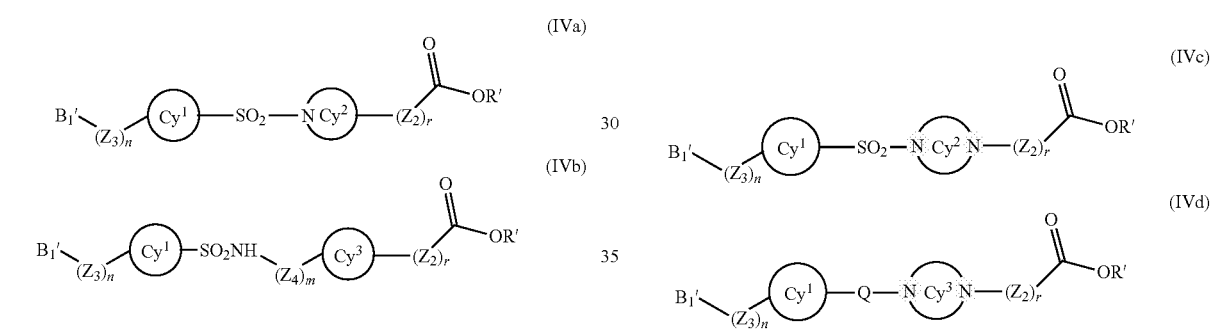

of formula (VIII) respectively, as shown in scheme 1:

Scheme 1

This conversion can be carried out in the presence of a base such as triethylamine, in a suitable solvent such as ethanol, and at a suitable temperature, preferably heating.

Compounds of formula (IV) having the formula (IVc) or the formula (IVd):

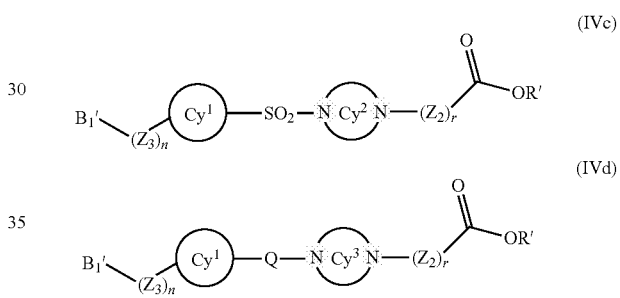

wherein Q is selected from the group consisting of —SO$_2$NH—(Z$_4$)$_m$—; —O—(Z$_4$)$_m$—; and —(Z$_4$)$_m$—; $B_1'$, $Z_2$-$Z_4$, m, n, r, $Cy^1$-$Cy^3$ are as defined in the compounds of formula (I); and R' is a carboxy protective group, can be prepared by coupling a compound of formula (IX) or formula (X) respectively with a compound of formula (XI), wherein X is a leaving group, such as halogen or methanesulfonate, as shown in scheme 2:

Scheme 2

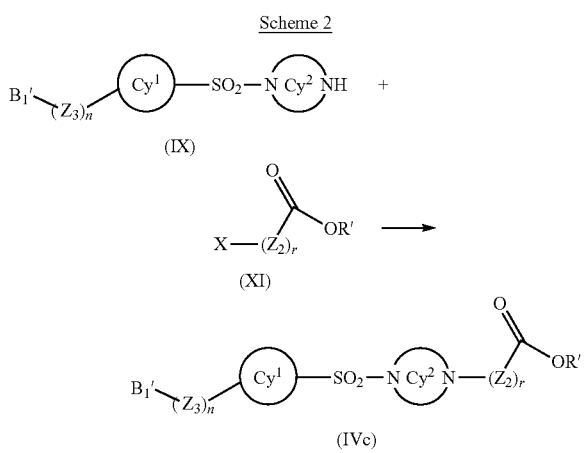

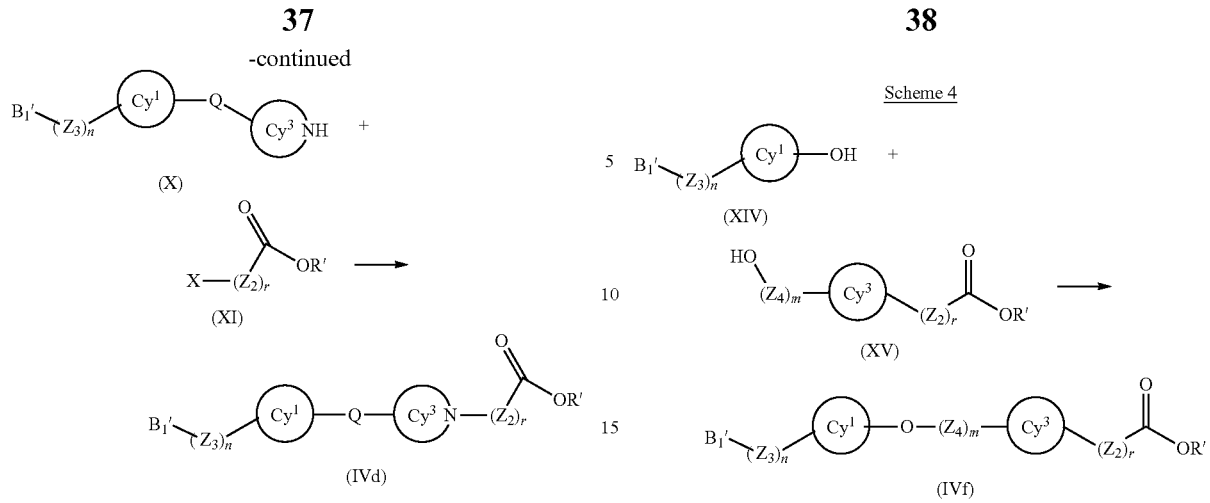

(X)

(XI)

(IVd)

This conversion can be carried out in the presence of a base such as potassium carbonate, in a suitable solvent, such as acetonitrile, and at a suitable temperature, preferably heating.

Compounds of formula (IV) having the formula (IVe):

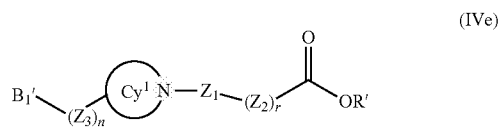

(IVe)

wherein $B_1'$, $Z_1$-$Z_2$, n, $Cy^1$-$Cy^3$ are as defined in the compounds of formula (I) and R' is a carboxy protective group, can be prepared by coupling a compound of formula (XII) with a compound of formula (XIII), wherein X is a leaving group, such as halogen or methanesulfonate, as shown in scheme 3:

Scheme 3

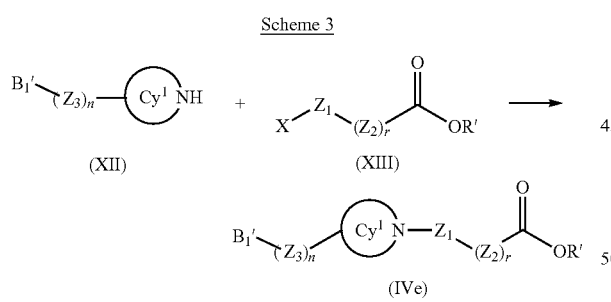

(XII)   (XIII)

(IVe)

Compounds of formula (IV) having the formula (IVf):

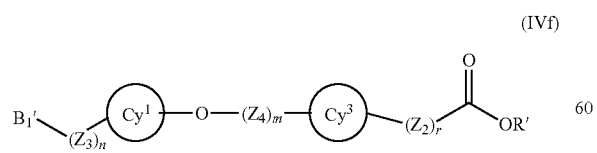

(IVf)

wherein $B_1'$, $Z_1$-$Z_2$, n, $Cy^1$-$Cy^3$ are as defined in the compounds of formula (I) and R' is as defined above, can be prepared by coupling a compound of formula (XIV) with a compound of formula (XV), as shown in scheme 4:

Scheme 4

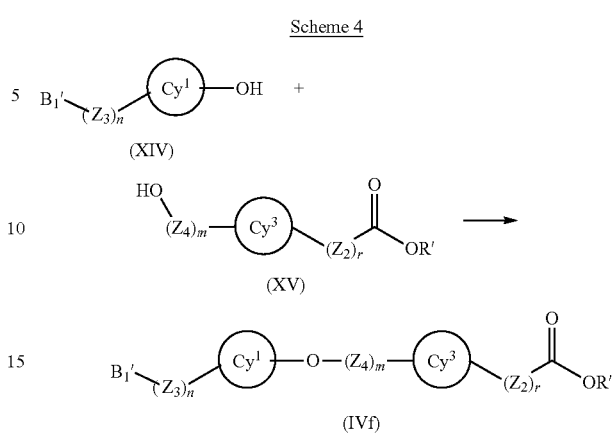

(XIV)

(XV)

(IVf)

This conversion can be carried out in the presence of $Ph_3P$ and diisopropyl azodicarboxylate (DIAD) in a suitable solvent, such as toluene, and at a suitable temperature, preferably heating.

Compounds of formula (IV) having the formula (IVg):

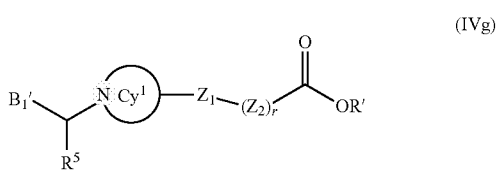

(IVg)

wherein $B_1'$, $Z_1$—$Z_2$, n, $Cy^1$-$Cy^3$ are as defined in the compounds of formula (I) and R' is as defined above, can be prepared by coupling a compound of formula (XVI) with a compound of formula (XVII), wherein X is a leaving group, such as halogen or methanesulfonate, and $R_5$ is H or optionally substituted $(C_1$-$C_4)$alkyl as shown in scheme 5:

Scheme 5

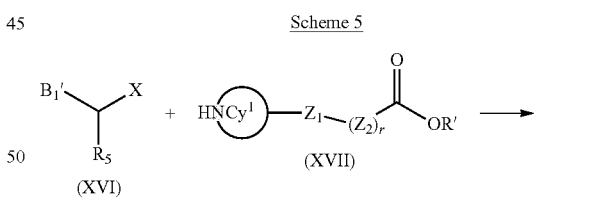

(XVI)   (XVII)

(IVg)

The compounds (IVe) and (IVg) can be prepared as defined above using analogous reaction conditions to those described for the preparation of compounds of formula (IVc) or (IVd).

Compounds of formula (IV) having the formula (IVh):

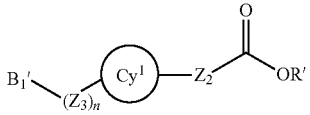

wherein $Z_2$-$Z_3$, n, and $Cy^1$ are as defined in the compounds of formula (I), R' is as defined above, and $B_1''$ is a radical of formula (D')

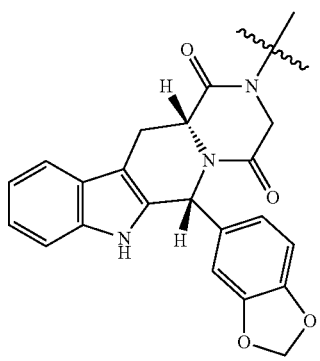

can be prepared by coupling a compound of formula (XVIII) with a compound of formula (XIX), wherein X is a leaving group, such as halogen or methanesulfonate, as shown in scheme 6:

Scheme 6

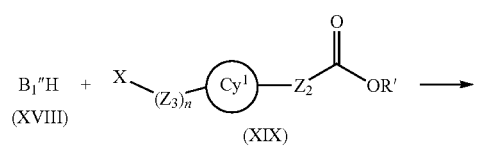

This conversion can be carried out in the presence of CuI, $K_3PO_4$ and (±)-1,2-transdiaminocyclohexane, in a suitable solvent, such as dioxane, and at a suitable temperature, preferably room temperature.

Alternatively, compounds of formula (IVh) can be prepared by coupling a compound of formula (XX) with a compound of formula (XXI), as shown in scheme 7:

Scheme 7

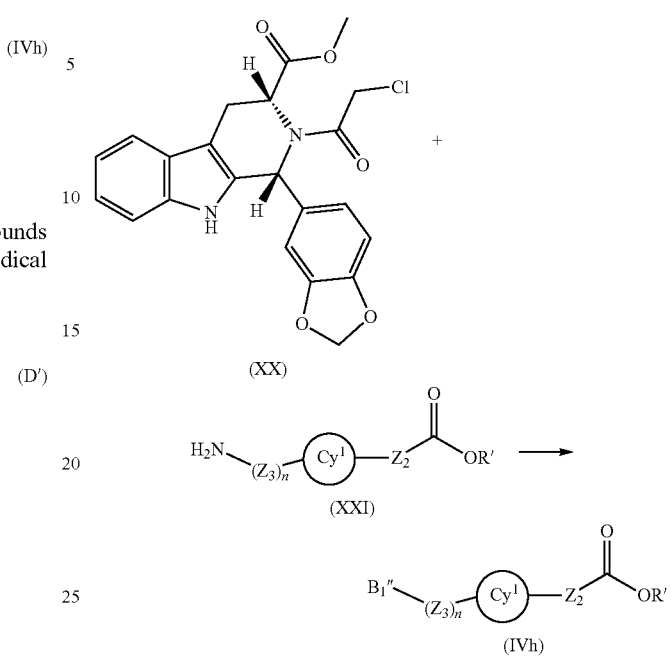

This conversion can be carried out in a suitable solvent, such as methanol, and at a suitable temperature, preferably heating.

Compounds of formula (II) can be prepared by an analogous manner to compounds of formula (I) as described above. The compounds of formulas (V) to (XXI) are commercially available or can be obtained by conventional synthetic processes as shown in the examples below.

The present invention also relates to a pharmaceutical composition comprising a therapeutically effective amount of a compound of formula (I) or a compound of formula (II) as defined above together with pharmaceutically acceptable excipients or carriers.

The expression "therapeutically effective amount" as used herein, refers to the amount of a compound that, when administered, is sufficient to prevent development of, or alleviate to some extent, one or more of the symptoms of the disease which is addressed. The specific dose of the compound of the invention to obtain a therapeutic benefit may vary depending on the particular circumstances of the individual patient including, among others, the size, weight, age and sex of the patient, the nature and stage of the disease, the aggressiveness of the disease, and the route of administration. For example, a dose of from about 0.01 to about 300 mg/kg may be used.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

The election of the pharmaceutical formulation will depend upon the nature of the active compound and its route of administration. Any route of administration may be used, for example oral, parenteral and topical administration.

For example, the pharmaceutical composition may be formulated for oral administration and may contain one or more physiologically compatible carriers or excipients, in solid or liquid form. These preparations may contain conventional ingredients such as binding agents, fillers, lubricants, and acceptable wetting agents.

The pharmaceutical composition may be formulated for parenteral administration in combination with conventional injectable liquid carriers, such as water or suitable alcohols. Conventional pharmaceutical excipients for injection, such as stabilizing agents, solubilizing agents, and buffers, may be included in such compositions. These pharmaceutical compositions may be injected intramuscularly, intraperitoneally, or intravenously.

The pharmaceutical composition may be formulated for topical administration. Formulations include creams, lotions, gels, powders, solutions and patches wherein the compound is dispersed or dissolved in suitable excipients.

The pharmaceutical compositions may be in any form, including, among others, tablets, pellets, capsules, aqueous or oily solutions, suspensions, emulsions, or dry powdered forms suitable for reconstitution with water or other suitable liquid medium before use, for immediate or retarded release.

The appropriate excipients and/or carriers, and their amounts, can readily be determined by those skilled in the art according to the type of formulation being prepared.

As demonstrated in the examples, the compounds of the invention are dual inhibitors of PDEs and HDACs, and therefore, may be used in the treatment and/or prevention of diseases mediated by the dual inhibition of PDE and HDAC.

In a particular embodiment, the invention refers to compounds of formula (I) as previously described, wherein $B_1$ is a radical of formula (A"), (B") or (D"), which are dual inhibitors of PDE5 and at least one HDAC selected from the group consisting of HDAC1, HDAC2, HDAC3 and HDAC6.

In another particular embodiment, the invention refers to compounds of formula (I) as previously described, wherein $B_1$ is a radical of formula (C") which are dual inhibitors of PDE9 and at least one HDAC selected from the group consisting of HDAC1, HDAC2, HDAC3 and HDAC6.

Thus, the invention relates to a compound of formula (I) or a compound of formula (II) or a pharmaceutical composition comprising the compound of formula (I) or formula (II) as defined above, for use as a medicament.

Moreover, the invention relates to a compound of formula (I) or a compound of formula (II) or a pharmaceutical composition comprising the compound of formula (I) or formula (II) as defined above, for use in the treatment and/or prevention of diseases mediated by the dual inhibition of PDE and HDAC. Thus, this aspect relates to the use of a compound of formula (I) or a compound of formula (II) as defined above, for the preparation of a medicament for the treatment and/or prevention of diseases mediated by the dual inhibition of PDE and HDAC; and may also be formulated as a method for the treatment and/or prevention of diseases mediated by the dual inhibition of PDE and HDAC, which comprises administering a therapeutically effective amount of the previously defined compound of formula (I) or a compound of formula (II) and one or more pharmaceutical acceptable excipients or carriers, in a subject in need thereof, including a human.

Examples of diseases mediated by the dual inhibition of PDE and HDAC include neurological disorders coursing with a cognition deficit or impairment, and neurodegenerative diseases. Thus, the compounds of the present invention may be useful in the treatment and/or prevention of neurological disorders coursing with a cognition deficit or impairment, or neurodegenerative diseases.

Therefore, the invention also relates to a compound of formula (I) or a compound of formula (II) or a pharmaceutical composition comprising the compound of formula (I) or formula (II) as defined above, for use in the treatment and/or prevention of neurological disorders coursing with a cognition deficit or impairment, or neurodegenerative diseases. Thus, this aspect relates to the use of a compound of formula (I) or a compound of formula (II) as defined above, for the preparation of a medicament for the treatment and/or prevention of neurological disorders coursing with a cognition deficit or impairment, or neurodegenerative diseases; and may also be formulated as a method for the treatment and/or prevention of neurological disorders coursing with a cognition deficit or impairment, or neurodegenerative diseases comprising administering a therapeutically effective amount of the previously defined compound of formula (I) or a compound of formula (II), and one or more pharmaceutical acceptable excipients or carriers, in a subject in need thereof, including a human.

In a particular embodiment, the neurodegenerative diseases are neurodegenerative diseases coursing with a cognition deficit or impairment. More particularly, the neurodegenerative disease or neurological disorder coursing with a cognition deficit or impairment is selected from Alzheimer's disease, Parkinson's disease, Huntington's disease, vascular dementia (uncomplicated, with delirium, with delusions or with depressed mood), mild cognitive impairment and age-associated cognition impairment. More preferably, the disease is Alzheimer's disease.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention.

EXAMPLES

General Procedure for Preparative HPLC Purification Method:

The HPLC measurement was performed using Gilson 281 from 233 pump (binary), an autosampler, and a UV detector. The fractions was detected by LC-MS. The MS detector was configured with an electrospray ionization source. The source temperature was maintained at 300-350° C.

HPLC Methods (Purification Methods):

Method 1: Reversed phase HPLC was carried out on luna (100×30 mm; 5 μm). Solvent A: water with 0.075% TFA; Solvent B: acetonitrile. Gradient: At 25° C., 28% of B to 58% of B within 10.5 min; then 58% B over 4 min, PDA Method 2: Reversed phase HPLC was carried out on luna C8 (100×30 mm; 5 μm). Solvent A: 10 mM $NH_4HCO_3$ in water; Solvent B: acetonitrile. Gradient: At 25° C., 45% of B to 65% of B within 12 min, 65% B over 2 min; then 65% of B to 95% of B in 0.2 min, 95% B over 2 min; then 45% of B in 0.2 min, 45% of B over 1.4 min. Flow rate: 20 mL/min. Monitor wavelength: 220 & 254 nm Method 3: Reverse phase HPLC was carried out on Luna C18 (150×25 mm; 5 μm). Solvent A: water with 0.040% ammonia hydrate; Solvent B: acetonitrile with 0.040% ammonia hydrate; Gradient: At room temperature, 20% of B to 40% of B within 6 min at 20 mL/min; then 40% B at 25 mL/min over 2 min, UV detector.

Method 4: Reversed phase HPLC was carried out on luna (100×30 mm; 5 μm). Solvent A: water with 0.075% TFA; Solvent B: acetonitrile with 0.075% TFA. Gradient: At 25° C., 26% of B to 46% of B within 6 min; then 40% B over 4 min, PDA.

Method 5. Reverse phase HPLC was carried out on Luna C18 (100×30 mm; 4 μm). Solvent A: water with 0.075% trifluoroacetic acid; Solvent B: acetonitrile with 0.075% trifluoroacetic acid. Gradient: At room temperature, 20% of B to 40% of B within 6 min at 25 mL/min; then 40% B at 25 mL/min over 2 min, UV detector.

Method 6. Reverse phase HPLC was carried out on Luna C18 (100×30 mm; 4 μm). Solvent A: water with 0.075% trifluoroacetic acid; Solvent B: acetonitrile with 0.075% trifluoroacetic acid. Gradient: At room temperature, 20% of B to 45% of B within 6 min at 25 mL/min; then 40% B at 25 mL/min over 3 min, UV detector.

Method 7: Reversed phase HPLC was carried out on Waters Xbridge (150*25 5u). Solvent A: 6.7 mM $NH_4HCO_3$ in water; Solvent B: acetonitrile. Gradient: At 25° C., 35% of B to 60% of B within 8 min, 60% B over 2 min; then 60% of B to 100% of B in 0.2 min, 100% B over 1.5 min; then 35% of B in 0.2 min, 35% of B over 2 min. Flow rate: 25 mL/min. Monitor wavelength: 220 & 254 nm Method 8: Reversed phase HPLC was carried out on Waters Xbridge (150*25 5u). Solvent A: 6.7 mM $NH_4HCO_3$ in water; Solvent B: acetonitrile. Gradient: At 25° C., 25% of B to 55% of B within 8 min, 55% B over 2 min; then 55% of B to 100% of B in 0.2 min, 100% B over 1.5 min; then 25% of B in 0.2 min, 25% of B over 2 min. Flow rate: 25 mL/min. Monitor wavelength: 220 & 254 nm Supercritical Fluid Chromatography (SFC) Separation Methods:

SFC separation was performed using Thar SFC Pre-80 and UV detector (220 nm)

Method 1:

Column: Chiralcel AD-H 5 μm, 3.0 cm id×25 cm L

Mobile phase: A for SFC CO2 and B for EtOH

Gradient: B: 40

Flow rate: 70 g/min

Back Pressure: 100 bar

Column temperature: 38° C.

The following abbreviations have been used in the examples: AcOH: acetic acid; Boc: tert-butoxycarbonyl; calc.: calculated; conc.: concentrated; DMAP: 4-Dimethylaminopyridine; DCM: dichloromethane; DIAD: Diisopropyl azodicarboxylate; DIC: N,N'-diisopropylcarbodiimide; DMAP: 4-(Dimethylamino)pyridine; DMF: dimethylformamide; DMSO: dimethylsulfoxide; EA/EtOAc: ethyl acetate; EDC.HCl: 1-ethyl-3-(3-dimethylamino-propyl)carbodiimide hydrochloride; eq: equivalent; ESI-MS: electrospray ionization mass spectrometry; $Et_3N$: triethylamine; HOBt: Hydroxybenzo-triazole; HPLC: High-performance liquid chromatography; LDA: Lithium diisopropylamide; MW: microwaves; NMM: N-methyl morpholine; PE: petrol ether; PFP: pentafluorophenol; PG: protective group; r.t.: room temperature; TEA: triethylamine; TFA: trifluoroacetic acid; THF: tetrahydrofuran; THP: tetrahydropyran; TLC: thin layer chromatography; TMSCl: trimethylsilyl chloride.

Preparation of Reagents

Preparation of Reagent KR-1: 1-tert-Butoxycarbonyl-4-(5-bromopyrimidin-2-yl)piperazine To a solution of commercially available 5-bromo-2-chloropyrimidin (9.75 g, 50 mmol) in $CH_3CN$ (100 mL) was added compound 1-Boc-piperazine (9.25 g, 50 mmol) and $K_2CO_3$ (13.8 g, 100 mmol). The reaction mixture was stirred at 80° C. overnight. Then, the reaction mixture was concentrated under vacuo and extracted with EA and washed with water, dried by $Na_2SO_4$ and concentrated under vacuo to give the KR-1 (15 g 87.7% yield). ESI-MS (M+1): 343, 345 calc. for $C_{13}H_{19}BrN_4O_2$: 342.1.

Preparation of Reagent KR-2: Ethyl 2-(4-(tert-butoxycarbonyl)piperazin-1-yl)pyrimidine-5-carboxylate To a solution of KR-1 (6.00 g, 17.49 mmol) in ethanol (100 mL) was added $Et_3N$ (1.77 g, 2.43 ml) and $Pd(dppf)_2Cl_2$ (5 g), then the reaction mixture was stirred at 100° C. at 1.5 MPa under CO atmosphere for overnight. The reaction mixture was filtrated and the filtrate was concentrated under vacuo to give KR-2 (5 g, 85.2% yield). ESI-MS (M+1): 337 calc. for $C_{16}H_{24}N_4O_4$: 336.2.

Preparation of Reagent KR-3: 5-bromo-2-[4-(N-tert-butoxycarbonyl-amino)piperidin-1-yl]pyrimidine KR-3 was obtained starting from 5-bromo-2-chloropyrimidin in an analogous manner to KR-1, but using tert-butylpiperidin-4-ylcarbamate instead of 1-Boc-piperazine. 84.3% yield. ESI-MS (M+1): 357, 359 calc. for $C_{14}H_{21}BrN_4O_2$: 356.1.

Preparation of Reagent KR-4: Ethyl 2-[4-(N-tert-butoxycarbonyl-amino)piperidin-1-yl]pyrimidine-5-carboxylate KR-4 was obtained starting from KR-3 in an analogous manner to KR-2. 61.22% yield. ESI-MS (M+1): 350.2 calc. for $C_{17}H_{26}N_4O_4$: 350.2.

Preparation of Reagent KR-5: ethyl 5-methylthiophene-2-carboxylate

To a solution of commercially available 5-methylthiophene-2-carboxylic acid (9.2 g, 0.065 mol) in DMF (80 mL) was added $K_2CO_3$ (17.9 g, 0.13 mol), then compound $CH_3CH_2I$ (15.2 g, 0.98 mol) was added slowly. The reaction mixture was stirred at room temperature overnight. After TLC (PE/EtOAc=2:1) showed the starting material was consumed completely, the mixture was quenched with water and extracted with EtOAc, the organic layer was washed with brine, dried over anhydrous $Na_2SO_4$, concentrated to give the crude reagent KR-5 (9.5 g, 86.3%) as a pale yellow oil which was used for the next step without further purification. ESI-MS (M+1): 171.0 calc. for $C_8H_{10}O_2S$: 170.0.

Preparation of Reagent KR-6: tert-butyl 3-[(4-ethoxycarbonylphenyl)methyl]-azetidine-1-carboxylate Commercially available tert-butyl 3-methyleneazetidine-1-carboxylate (500 mg, 3 mmol) was treated with a 0.5 M solution of 9-BBN in THF (10 mL), and the mixture was heated at reflux for 4 h. The resulting mixture was transferred into a stirred mixture of ethyl 4-iodobenzoate (1.7 g, 6 mmol), $Pd_2(dba)_3$ (270 mg, 0.3 mmol), X-Phos (450 mg, 0.9 mmol), and $Na_2CO_3$ (1 g, 9 mmol) in 1,4-dioxane (40 mL) and $H_2O$ (4 mL). The resulting mixture was stirred at reflux overnight. Then filtered, the mixture was extracted with EtOAc, the organic layer was washed with brine, dried over anhydrous $Na_2SO_4$, concentrated to give the crude compound which was purified by column chromatography (eluting with PE/EtOAc=50:1 to 5:1) to give pure reagent KR-6 (200 mg, 20% yield) as a pale yellow oil. ESI-MS (M+1): 320 calc. for $C_{18}H_{25}NO_4$: 319.1.

Preparation of Reagent R-09a: Ethyl 2-(piperazin-1-yl)pyrimidine-5-carboxylate

To a solution of KR-2 (2.50 g, 7.44 mmol) was added 4 mol/L DCM/HCl (30 mL). The reaction mixture was stirred at r.t. overnight, and then concentrated to give R-09a (320 mg, 96.7% yield). ESI-MS (M+1): 237 calc. for $C_{11}H_{16}N_4O_2$: 236.1.

Preparation of Reagent R-09b: Ethyl 2-(4-aminopiperidin-1-yl)pyrimidine-5-carboxylate R-09b was obtained starting from KR-4 in an analogous manner to R-09a. 93.5% yield. ESI-MS (M+1): 251 calc. for $C_{12}H_{18}N_4O_2$: 250.1.

Preparation of Reagent R-09e: ethyl 4-(azetidin-3-ylmethyl)benzoate

A solution of reagent KR-6 (200 mg, 0.63 mmol) in HCl/EtOAc (10 mL) was stirred at r.t. for 1 h, then concentrated to give the crude reagent R-09e (150 mg, quant.) as a white solid. ESI-MS (M+1): 220; calc. for $C_{13}H_{17}NO_2$: 219.1.

Preparation of Reagent R-11a: ethyl 3-methylenecyclobutanecarboxylate

To a solution of commercially available 3-methylenecyclobutanecarbonitrile (10.7 g, 115 mmol) in EtOH (70 mL) was added KOH (25.2 g, 450 mmol), then the mixture was stirred at reflux overnight. The resulting mixture was stirred at reflux overnight until TLC showed the starting material was consumed completely, the solvent was evaporated and water was added. 1 N HCl was added to bring pH to ~3 and extracted with EtOAc, the organic layer was washed with brine, dried over anhydrous $Na_2SO_4$, concentrated to give the crude product (12.3 g, ~95%). The crude product (12.3 g, 110 mmol) was dissolved in DMF (120 mL). Then EtI (21.5 g, 138 mmol) and $K_2CO_3$ (31.7 g, 230 mmol) were added to this solution. The mixture was stirred at r.t. for 8 h. Then water was added and extracted with EtOAc, the organic layer was washed with brine, dried over anhydrous $Na_2SO_4$, concentrated to give a crude which was purified by column to give the reagent R-11a (13.6 g, 88% yield) as a pale yellow oil. GC-MS (M): 140 calc. for $C_8H_{12}O_2$: 140.08.

Preparation of Reagent R-12b: ethyl 5-(bromomethyl)thiophene-2-carboxylate

To a solution of reagent KR-5 (1.9 g, 0.011 mol) in $CCl_4$ (30 mL) was added benzoyl peroxide (BPO) (212 mg, 0.001 mmol) and N-Bromosuccinimide (NBS) (2.85 g, 0.016 mmol), then the reaction mixture was stirred at reflux for 2 h until TLC (PE/EtOAc=5:1) showed the starting material was consumed completely, the mixture was extracted with DCM, the organic layer was washed with aqueous $NaHCO_3$, brine, dried over anhydrous $Na_2SO_4$, concentrated to give the crude compound which was purified by silica gel chromatography (PE/EtOAc=5:1) to give pure reagent R-12b (1.3 g, 48.1%) as a yellow oil. ESI-MS (M+1): 249.1 calc. for $C_8H_9BrO_2S$: 247.9.

Preparation of Reagent R-13a: ethyl 4-(trifluoromethylsulfonyloxy)-cyclohex-3-ene-1-carboxylate To a solution of commercially available ethyl 4-oxocyclohexanecarboxylate (3.0 g, 17.65 mmol) in anhydrous THF (30 mL) was added Lithium bis(trimethylsilyl)amide (LHMDS) (18.53 mL, 1.0 M in THF, 18.53 mmol) at −78° C., then the mixture was stirred at the same temperature for 1 h, compound $PhN(SO_2CF_3)_2$ (6.62 g, 18.53 mmol) in THF (20 mL) was added under $N_2$ protection. After addition, the mixture was stirred at room temperature overnight until TLC showed the starting material was consumed completely, the mixture was quenched with aqueous $KHSO_4$, extracted with methyl t-butyl ether (MTBE), the organic layer was washed with 1.0 M aqueous NaOH, aqueous $NH_4Cl$, brine, dried over anhydrous $Na_2SO_4$, concentrated to give the crude reagent R-13a (5.0 g, 93%) as a yellow oil. ESI-MS (M+1): 303 calc. for $C_{10}H_{13}F_3O_5S$: 302.0.

Preparation of Reagent R-14a: Ethyl 1-benzyl-4-methylpyrrolidine-3-carboxylate (trans racemic)

To a solution of the commercially available (E)-methyl but-2-enoate (32 g, 0.28 mol) was added toluene (500 mL), N-(methoxymethyl)(phenyl)-N-((trimethylsilyl)methyl) methanamine (74 g, 0.31 mol) and $CF_3COOH$ (30 g, 0.28 mol). The reaction mixture was heated at 50° C. for 18 h. The reaction mixture was concentrated, quenched with saturated sodium bicarbonate, extracted with DCM, dried over anhydrous $Na_2SO_4$, filtered and concentrated to give crude R-14a (40 g, 57.97% yield) as a pale yellow oil. ESI-MS (M+1): 248 calc. for $C_{15}H_{21}NO_2$: 247.1.

Preparation of Reagent R-19a: bromo-(2-ethoxy-2-oxo-ethyl)zinc

Zn powder (5.2 g, 80 mmol) was put into a 250 mL of three-neck flask under N2 protection, and then TMSCI (0.5 mL) being dissolved in dry THF (20 mL) was injected into the flask. The suspension mixture was stirred at room temperature for 20 min, then commercially available ethyl 2-bromoacetate (6.5 mL) dissolved in dry THF (50 mL) was dropped into the flask for about 30 min at room temperature. After the addition of was complete, the reaction mixture was stirred at 40° C. for another 30 min which was used for the next step directly.

Synthetic Route 1a
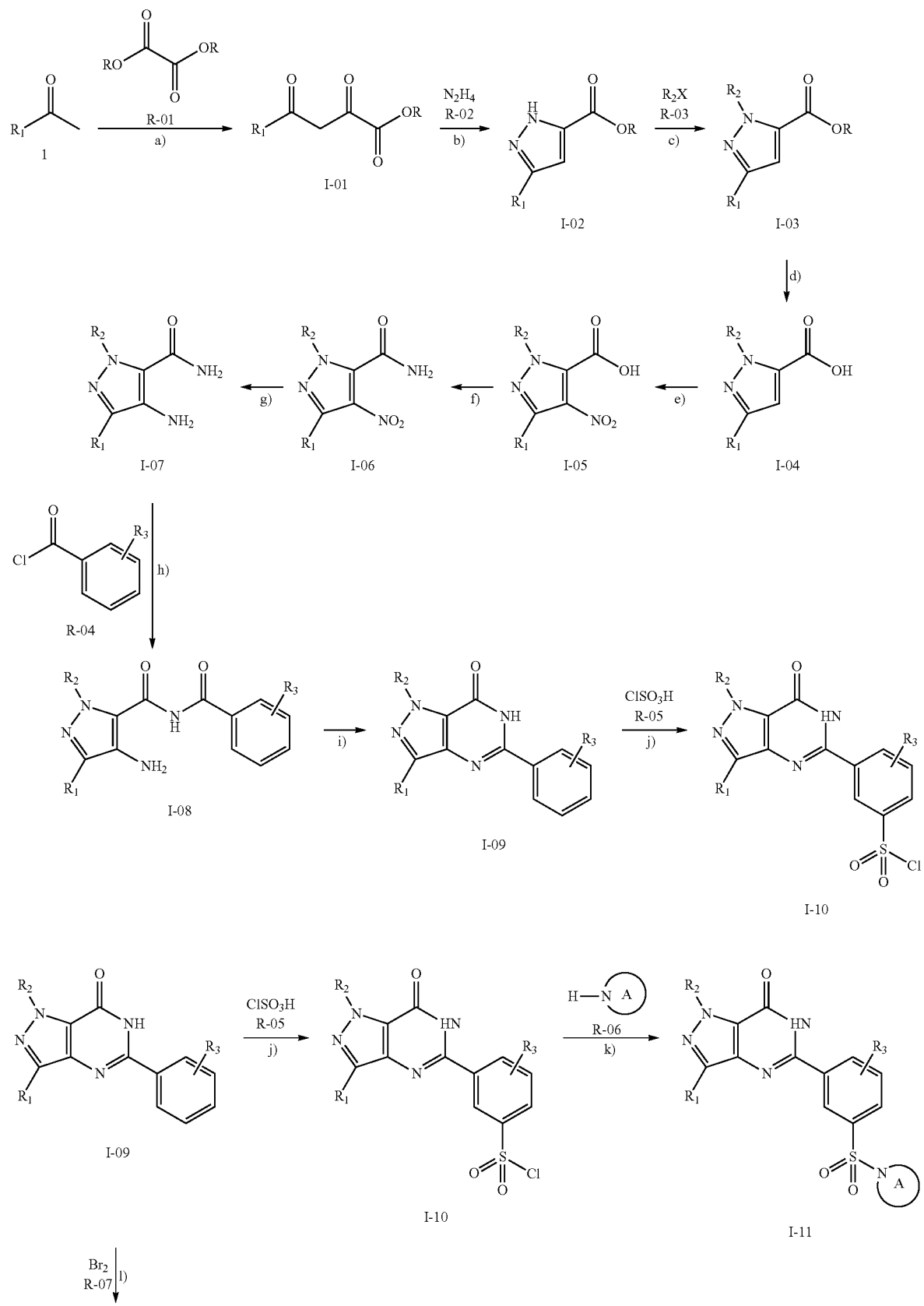

-continued

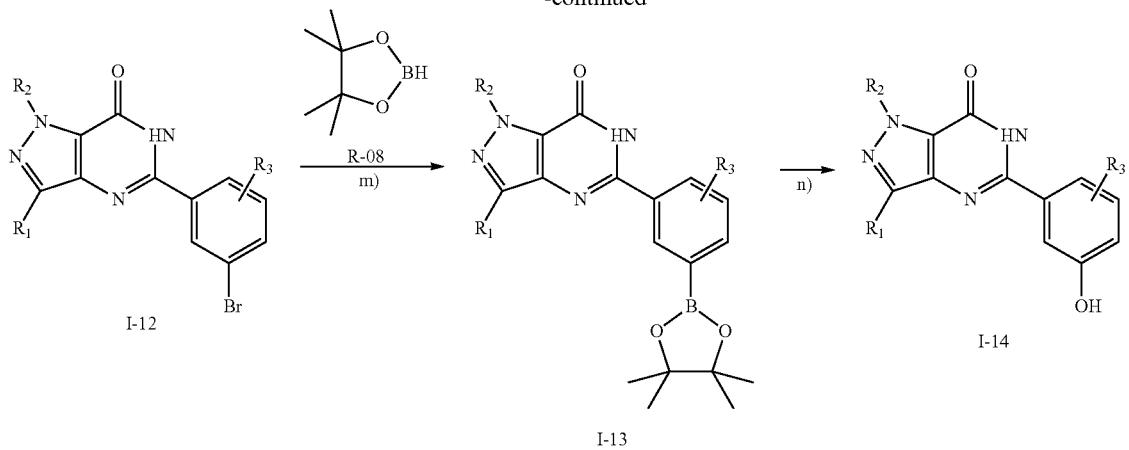

Conditions: a) Na (1 eq), 1 hour at r.t. in ethanol; then, R-01 (2 eq) overnight at r.t.; b) R-02 (2 eq) in 2-methoxyethanol/CH$_3$COOH overnight at 100° C.; c) Cs$_2$CO$_3$ (2 eq), R-03 (1.25 eq) in DMF, r.t.; d) HCl (6 M) overnight at 100° C.; e) H$_2$SO$_4$(conc)/HNO$_3$ (1:2) added to H$_2$SO$_4$ (conc.) solution; then, overnight at 50° C.; f) refluxed overnight in SOCl$_2$; then, in THF, added into NH$_3$•H$_2$O at 0° C. for 2 hours; g) Pd/C in methanol at 30° C. under 50 Psi at H$_2$ atmosphere overnight; h) R-04 (1 eq), Et$_3$N (2 eq) in DCM, r.t. for 12 hours; i) NaOH (2 eq) in ethanol/H$_2$O/H$_2$O$_2$ (3:1:0.1) overnight at 100° C.; j) ClSO$_3$H, r.t. for 2 hours; k) R-06 (2 eq) in ethanol, MW at 100° C. for 1 hour; l) Br$_2$ (1.2 eq) in AcOH overnight at r.t.; m) AcOK (2 eq), R-08 (1.2 eq) and (dppf)$_2$Cl$_2$Pd (0.1 eq), in dioxane, overnight at 90° C.; n) NaOH/H$_2$O (4M) and H$_2$O$_2$ (1.3 eq) in water overnight at r.t.

In the scheme above R is (C$_1$-C$_6$)alkyl, X is a leaving group, such as halogen, A is an optionally substituted 3- to 7-membered heterocyclic monocyclic ring.

Preparation of Intermediate I-01a: Ethyl 2,4-dioxoheptanoate

To a solution of methyl propyl ketone (1, 43.06 g, 0.5 mol) in ethanol (200 mL) was added Na (41.5 g, 0.5 mol), stirred at r.t. for 1 hours, then diethyl oxalate (R-01a, 73.03 g, 68 mL) was added into the reaction mixture and stirred at r.t. overnight. The reaction mixture was quenched by NH$_4$Cl solution and concentrated under vacuo to give the crude product, then extracted with EA and washed with water, concentrated under vacuo to give I-01a (60 g, 64.5% yield). ESI-MS (M+1): 187 calc. for C$_9$H$_{14}$O$_4$: 186.1.

Preparation of Intermediate I-02a: Ethyl 3-propyl-1H-pyrazole-5-carboxylate

To a solution of I-01a (42 g, 0.225 mol) in 2-Methoxyethanol:CH$_3$COOH (335 mL: 335 mL) was added NH$_2$NH$_2$.H$_2$O (22.52 g, 0.45 mmol). The reaction mixture was heated to 100° C. overnight. The reaction mixture was concentrated under vacuo and extracted with EA, washed with water and the organic layer was concentrated under vacuo to give I-02a (35 g, 85% yield). ESI-MS (M+1): 183 calc. for C$_9$H$_{14}$N$_2$O$_2$: 182.1.

Preparation of Intermediate I-03a: Ethyl 1-methyl-3-propyl-1H-pyrazole-5-carboxylate To a solution of I-02a (40 g, 0.22 mol) in DMF (500 mL) was added Cs$_2$CO$_3$ (0.44 mol, 2 eq), then compound CH$_3$I (0.28 mol, 1.25 eq) was added. The reaction mixture was stirred at r.t. overnight. The reaction mixture was concentrated under vacuo and extracted with DCM, washed with water. The organic layer was concentrated under vacuo to give I-03a (30 g, 70% yield). ESI-MS (M+1): 197 calc. for C$_{10}$H$_{16}$N$_2$O$_2$: 196.1.

Preparation of Intermediate I-04a: 1-Methyl-3-propyl-1H-pyrazole-5-carboxylic acid The solution of I-03a (11 g, 56.12 mmol) in HCl (121 mL, 6 M) was heated to 100° C. overnight. The reaction mixture was concentrated under vacuo and extracted with EA, washed with water and the organic layer was concentrated under vacuo to give I-04a (9.4 g, 98% yield). ESI-MS (M+1): 169 calc. for C$_8$H$_{12}$N$_2$O$_2$: 168.1.

Preparation of Intermediate I-05a: 1-Methyl-4-nitro-3-propyl-1H-pyrazole-5-carboxylic acid To a solution of I-04a (9.5 g, 56.54 mmol) was dissolved in conc. H$_2$SO$_4$ (40 mL). Then conc. H$_2$SO$_4$:HNO$_3$ (3.6 mL:8 mL) was added into the reaction mixture slowly, and stirred at 50° C. overnight. The reaction mixture was poured into ice-water and filtered, the filtrate cake was collected and concentrated under vacuo to give I-05a (8 g, 71.11% yield). ESI-MS (M+1): 214 calc. for C$_8$H$_{11}$N$_3$O$_4$: 213.1

Preparation of Intermediate I-06a: 1-Methyl-4-nitro-3-propyl-1H-pyrazole-5-carboxamide To a solution of 1-05a (8 g, 40.20 mmol) was dissolved in SOCl$_2$ (20 mL), then refluxed overnight. The reaction mixture was concentrated under vacuo to give 1-methyl-4-nitro-3-propyl-1H-pyrazole-5-carbonyl chloride. Then, this compound was dissolved in THF (100 mL), and then was added into NH$_3$H$_2$O (100 mL) at ice-water bath. After additional 2 hours, the reaction mixture was concentrated under vacuo to give I-06a (8 g). ESI-MS (M+1): 213 calc. for C$_8$H$_{12}$N$_4$O$_3$: 212.1.

Preparation of Intermediate I-07a: 4-Amino-1-methyl-3-propyl-1H-pyrazole-5-carboxamide To a solution of I-06a (10 g, 47.17 mmol) was dissolved in methanol (100 mL), then Pd/C (5 g) was added into the reaction mixture, and stirred at 30° C. under 50 Psi (345 kPa) at H$_2$ atmosphere overnight. The reaction mixture was filtrated and the filtrate was concentrated under vacuo to give I-07a (8.5 g, 98.83% yield). ESI-MS (M+1): 183 calc. for C$_8$H$_{14}$N$_4$O: 182.1.

Preparation of Intermediate I-08a: 5-(2-Ethoxyphenylcarbonylaminocarbonyl)-1-methyl-3-propyl-1H-pyrazol-4-amine To a solution of I-07a (6 g, 32.97 mmol) in DCM (100 mL) was added Et$_3$N (6.6 g, 65.34 mmol), 2-ethoxybenzoyl chloride (R-04a, 6.1 g, 32.97 mmol). The reaction mixture was stirred at r.t. overnight. The reaction mixture was washed quenched by adding water and extracted with DCM. The organic phase was collected, dried over Na$_2$SO$_4$ and concentrated under vacuo to give I-08a (10.85 g, 98% yield). ESI-MS (M+1): 331 calc. for C$_{17}$H$_{22}$N$_4$O$_3$: 330.2.

Preparation of Intermediate I-09a: 6,7-Dihydro-5-(2-ethoxyphenyl)-1-methyl-7-oxo-3-propyl-1H-pyrazolo[4,3-d]pyrimidine To a solution of I-08a (8 g, 24.24 mmol) was dissolved in ethanol (273 mL), water (78 mL), NaOH (2.11 g, 52.75 mmol) and H$_2$O$_2$ (8.75 mL). The reaction mixture was stirred at 100° C. overnight. Then, the reaction mixture was concentrated under vacuo, washed with water and extracted with DCM. The organic phase was collected, dried over Na$_2$SO$_4$ and concentrated to give I-09a (4 g, 53.3% yield). ESI-MS (M+1): 313 calc. for C$_{17}$H$_{20}$N$_4$O$_2$: 312.2.

Preparation of Intermediate I-10a: 4-Ethoxy-3-(6,7-dihydro-1-methyl-7-oxo-3-propyl-1H-pyrazolo[4,3-d]pyrimidin-5-yl)benzene-1-sulfonyl chloride I-09a (2.5 g, 8.0 mmol) was added into ClSO$_3$H (R-05, 10 mL) at ice-water and stirred at r.t. for 2 hours. The reaction mixture was quenched by adding water, and then filtrated. The filtrate cake was collected and dried under vacuo to give I-10a (2.0 g) ESI-MS (M+1): 411 calc. for C$_{17}$H$_{19}$ClN$_4$O$_4$S: 410.1.

Preparation of Intermediate I-11a: N-([3-(6,7-dihydro-1-methyl-7-oxo-3-propyl-1H-pyrazolo[4,3-d]pyrimidin-5-yl)-4-ethoxy]benzene-1-sulfonyl)piperazine To a solution of I-10a (0.41 g, 1 mmol) in ethanol (273 mL) was added piperazine (R-06a, 0.256 g, 2 mmol) and the mixture was stirred at 100° C. under microwave (MW) for 1 hour. The reaction mixture was concentrated under vacuo to give I-11a (0.4 g, 86.8% yield). ESI-MS (M+1): 461 calc. for C$_{21}$H$_{28}$N$_6$O$_4$S: 460.2.

Preparation of Intermediate I-12a: 5-(5-Bromo-2-ethoxyphenyl)-1-methyl-3-propyl-1H-pyrazolo[4,3-d]pyrimidin-7(6H)-one To a solution of intermediate I-09a (2 g, 6.41 mmol) in AcOH (30 mL) was added Br$_2$ (1.25 g, 7.69 mmol) slowly, the reaction mixture was stirred at room temperature overnight, then Na$_2$SO$_3$ (0.0189 g, 3 mmol) and water was added into the reaction mixture, stirred at r.t. for 2 hours. Then the reaction mixture was concentrated under vacuo and extracted by EA and washed with water and dried by Na$_2$SO$_4$, then concentrated under vacuo to give I-12a (2 g, 79.7%). ESI-MS (M+1): 391 calc. for C$_{17}$H$_{19}$BrN$_4$O$_2$: 390.2.

Preparation of Intermediate I-13a: 5-(2-Ethoxy-5-(4,4,5,5-tetramethyl-1,3,2-dioxaborolan-2-yl)phenyl)-1-methyl-3-propyl-1H-pyrazolo[4,3-d]pyrimidin-7(6H)-one To a solution of compound I-12a (3.9 g, 10.0 mmol) in 1,4-dioxane (200 mL) was added potassium acetate (AcOK) (1.96 g, 20 mmol), 4,4,4',4',5,5,5',5'-octamethyl-2,2'-bi(1,3,2-dioxaborolane) (3.05 g, 12 mmol) and (dppf)$_2$Cl$_2$Pd (816 mg, 1 mmol). The reaction mixture was stirred at 90° C. overnight, and then filtered and the filtrate was concentrated to give I-13a (320 mg, 96.7%). ESI-MS (M+1): 439 calc. for C$_{23}$H$_{31}$BN$_4$O$_4$: 438.3.

Preparation of Intermediate I-14a: [3-(6,7-Dihydro-1-methyl-7-oxo-3-propyl-1H-pyrazolo[4,3-d]pyrimidin-5-yl)]-4-ethoxyphenol To a solution of compound I-13a (4.39 g, 10 mmol) in water (50 mL) was added NaOH/H$_2$O (4 M, 13 mmol) and hydrogen peroxide (494 mg, 13 mmol). The reaction mixture was stirred at room temperature overnight. Na$_2$SO$_3$ solution was added and stirred for 2 hours. Then extracted by EA and dried by Na$_2$SO$_4$ and the organic phase was concentrated to give the intermediate I-14a (2.0 mg, 61%). ESI-MS (M+1): 329 calc. for C$_{17}$H$_{20}$N$_4$O$_3$: 328.4.

Synthetic Route 1b

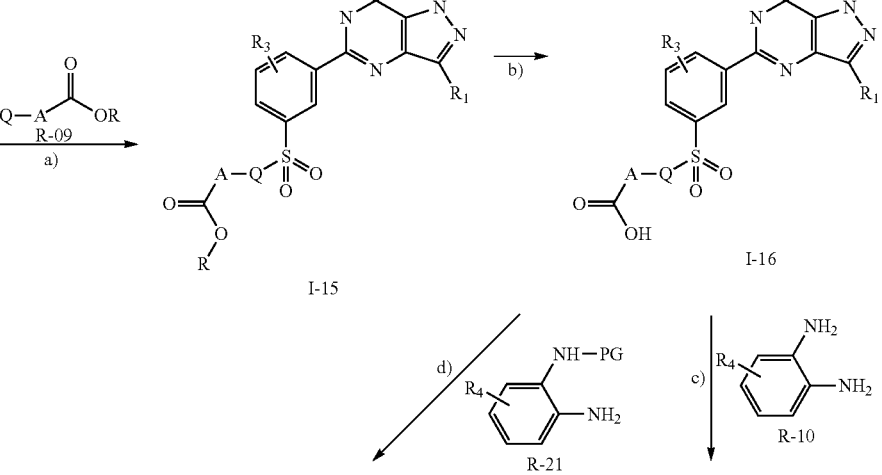

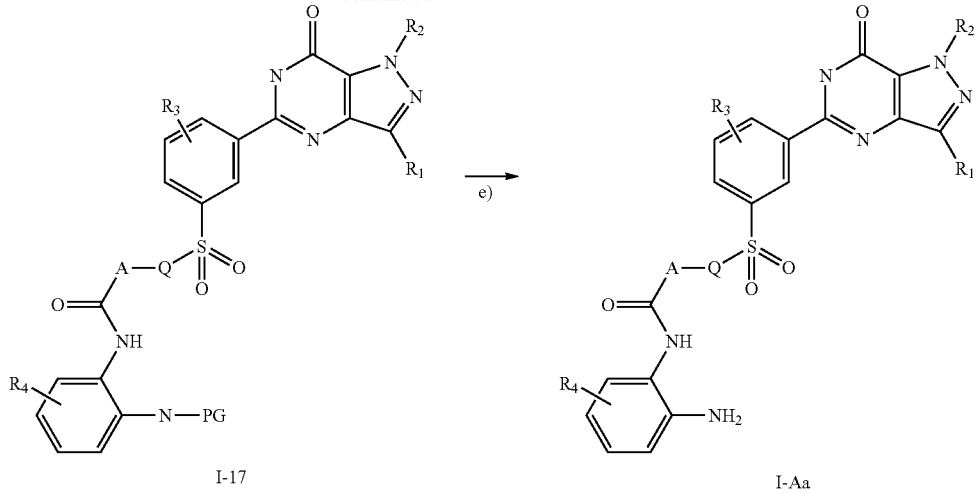

Conditions: a) Et₃N and R-09 in ethanol, MW at 100° C. for 2 hours; b) LiOH•H₂O (5 eq) in THF/methanol/H₂O, overnight at r.t.;
c) EDC•HCl (1.2 eq), HOBt (1.2 eq), NMM (5 eq) and R-10 (1 eq) in DMF, overnight at r.t.; d) SOCl₂ (3.3 eq) at 80° C. for 2 hours;
then, TEA (2 eq) and R-21 (1 eq) in CH₂Cl₂ at r.t.; e) HCl/EtOAc (4 N), 16 hours at r.t.

In the scheme above R is $(C_1-C_6)$alkyl, Q is NH or

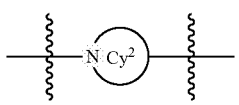

wherein $Cy^2$ is an heterocyclic ring, and A is a hydrocarbon chain, which optionally contains nitrogen, sulphur and/or oxygen atoms, and optionally contains one or more aromatic, heteroaromatic, carbocyclic and/or heterocyclic rings.

Preparation of Intermediate I-15a: Ethyl 2-(4-[3-(6,7-dihydro-1-methyl-7-oxo-3-propyl-1H-pyrazolo[4,3-d]pyrimidin-5-yl)-4-ethoxyphenylsulfonyl]piperazin-1-yl)pyrimidine-5-carboxylate To a solution of I-10a (0.41 g, 1 mmol) in ethanol (273 mL) was added ethyl 2-(piperazin-1-yl)pyrimidine-5-carboxylate (R-09a, 0.236 g, 2 mmol), Et₃N (303 mg, 3 mmol). The mixture was stirred at 100° C. under MW for 2 hours. The reaction mixture was concentrated under vacuo to give I-15a (0.4 g, 65.5% yield). ESI-MS (M+1): 611 calc. for $C_{28}H_{34}N_8O_6S$: 610.2.

Preparation of Intermediate I-16a: 2-(4-[3-(6,7-Dihydro-1-methyl-7-oxo-3-propyl-1H-pyrazolo[4,3-d]pyrimidin-5-yl)-4-ethoxyphenylsulfonyl]piperazin-1-yl)pyrimidine-5-carboxylic acid To a solution of I-15a (500 mg, 0.82 mmol) in THF/methanol/H₂O (10/1/5 mL) was added LiOH.H₂O (168 mg, 4.1 mmol). The resulting mixture was stirred at r.t. for overnight. After TLC showed that most of the starting materials were consumed completely, the mixture was diluted with water and adjusted pH to 2-3. The mixture was extract with EA and washed with brine, dried over anhydrous Na₂SO₄ and concentrated to give crude I-16a (300 mg, 63.8% yield). ESI-MS (M+1): 583 calc. for $C_{26}H_{30}N_8O_6S$: 582.2.

Preparation of Compound 1-01: N-(2-aminophenyl)-2-[4-[4-ethoxy-3-(1-methyl-7-oxo-3-propyl-6H-pyrazolo[4,3-d]pyrimidin-5-yl)phenyl]sulfonylpiperazin-1-yl]pyrimidine-5-carboxamide To a solution of I-16a (0.583 g, 1 mmol) in DMF (20 mL) was added EDC.HCl (230 mg, 1.2 mmol), HOBt (160 mg, 1.2 mmol), benzene-1,2-diamine (commercially available R-10a, 108 mg, 1 mmol), NMM (505 mg, 5 mmol). The mixture was stirred at room temperature overnight. The mixture was diluted with EtOAc and washed with brine, dried over anhydrous Na2SO4 and concentrated to give the crude product which was purified by column chromatography to give the compound 1-01 (400 mg, 45%). ESI-MS (M+1): 673 calc. for $C_{32}H_{36}N_{10}O_5S$ 672.76; Rt is 2.53 (HPLC Method: 1)

Following the same synthetic route for compound 1-01 and using the same reagents unless otherwise indicated in the table below, the following compounds were obtained:

| Example | R$_t$ (min) | [M + 1]⁺ | HPLC Method | Starting Materials |
|---|---|---|---|---|
| 1-02 | 2.44 | 687.1 | 1 | Ethyl 2-(4-aminopiperidin-1-yl)pyrimidine-5-carboxylate (R-09b)/benzene-1,2-diamine (R10a) |
| 1-03 | 2.40 | 616.1 | 1 | Ethyl 4-(aminomethyl)benzoate (R-09c)/benzene-1,2-diamine (R10a) |

Synthetic Route 1c
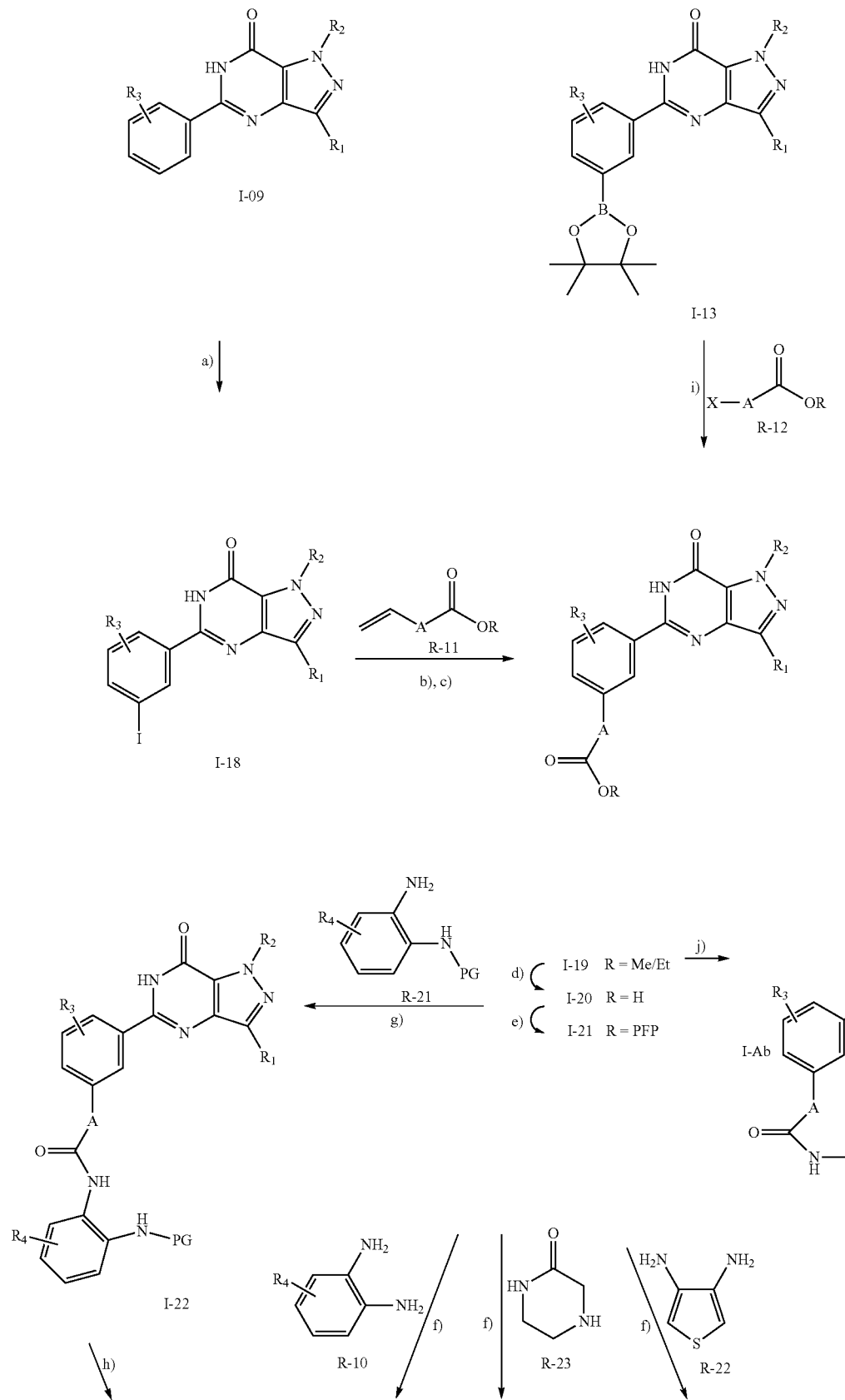

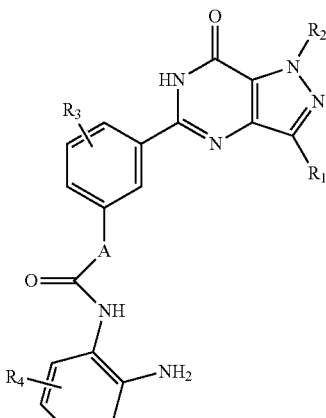

I-Ab1

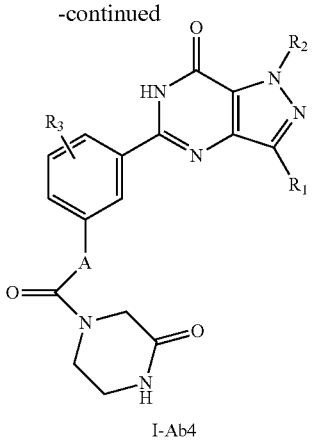

I-Ab4

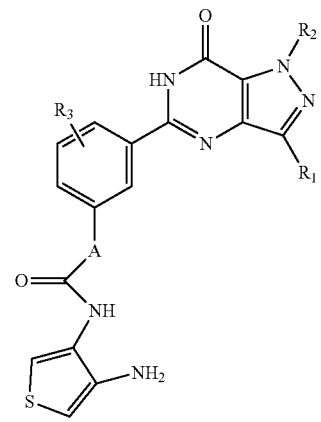

I-Ab3

Conditions: a) NIS (1.2 eq), TFA, overnight at r.t.; b) R-11, 9-BBN (0.5M solution) in THF, reflux for 4 h.; c) I-18, Pd$_2$(dba)$_3$ (0.05 eq), X-Phos (0.12 eq), Na$_2$CO$_3$ (2.5 eq), 1,4-dioxane and H$_2$O, reflux overnight; d) LiOH•H$_2$) (5 eq) in THF/methanol/H$_2$O, overnight at r.t; e) PFP (1 eq), DIC (1.6 eq) in CH$_2$Cl$_2$, overnight at r.t.; f) R-10, R-22 or R-23 (1.1 eq), (DMAP (1.1 eq)) and DIEA (2.1 eq) in DMF at 60° C.-80° C. overnight; g) SOCl$_2$ (10 eq) at 80° C. for 2 hours; then, TEA (2 eq) and R-21 (1 eq) in CH$_2$Cl$_2$ at r.t.; h) HCl/EtOAc (4N), 16 hours at r.t.; i) K$_2$CO$_3$ (3 eq) in water, Pd(PPh$_3$)$_4$ (0.1 eq) and R-12 (1.1 eq) in 1,4-dioxane, overnight at 80° C.; j) SOCl$_2$ at 80° C. for 3 hours, then methylurea (4.0 eq), DIEA (2.0 eq), CH$_3$CN, 80° C., overnight.

In the scheme above R is (C$_1$-C$_6$)alkyl, X is an halogen and A is a hydrocarbon chain, which optionally contains nitrogen, sulphur and/or oxygen atoms, and optionally contains one or more aromatic, heteroaromatic, carbocyclic and/or heterocyclic rings.

Preparation of Intermediate I-18a: 5-(2-ethoxy-5-iodo-phenyl)-1-methyl-3-propyl-6H-pyrazolo[4,3-d]pyrimidin-7-one To a solution of intermediate I-09a (10 g, 32 mmol) in TFA (50 mL) was added N-Iodosuccinimide (NIS) (8.6 g, 38.4 mmol) at 0° C. The mixture solution was stirred at r.t. overnight. The mixture was quenched with aqueous water and extracted with EtOAc, the organic layer was washed with brine, dried over anhydrous Na$_2$SO$_4$, concentrated to give the crude product which was purified by the column to give the intermediate I-18a (11 g, 79%) as a white solid. ESI-MS (M+1): 439.1; calc. for C$_{17}$H$_{19}$IN$_4$O$_2$: 438.0.

Preparation of Intermediate I-19a: ethyl 3-[[4-ethoxy-3-(1-methyl-7-oxo-3-propyl-6H-pyrazolo[4,3-d]pyrimidin-5-yl)phenyl]methyl]cyclobutanecarboxylate Reagent R-11a (700 mg, 5 mmol) was treated with a 0.5 M solution of 9-BBN in THF (12 mL), and the mixture was heated at reflux for 3 h. The resulting mixture was transferred into a stirred mixture of Intermediate I-18a (1.66 g, 3.8 mmol), Pd$_2$(dba)$_3$ (138 mg, 0.15 mmol), X-Phos (143 mg, 0.3 mmol), and Na$_2$CO$_3$ (850 mg, 8 mmol) in 1,4-dioxane (35 mL) and H$_2$O (6 mL). The resulting mixture was stirred at reflux overnight until TLC showed the starting material was consumed completely, then filtered, the mixture was extracted with EtOAc, the organic layer was washed with brine, dried over anhydrous Na$_2$SO$_4$, concentrated to give the crude compound which was purified by column chromatography (eluting with PE/EtOAc=50:1 to 5:1) to give pure compound intermediate I-19a (1.38 g, 80.3% yield) as a pale yellow solid. ESI-MS (M+1): 453.2 calc. for C$_{25}$H$_{32}$N$_4$O$_4$: 452.2.

Preparation of Intermediate I-20a: 3-[[4-ethoxy-3-(1-methyl-7-oxo-3-propyl-6H-pyrazolo[4,3-d]pyrimidin-5-yl)phenyl]methyl]cyclobutanecarboxylic acid To a solution of intermediate I-19a (1.38 g, 3.05 mmol) in THF/MeOH/H2O (3/3/2, 32 mL) was added LiOH.H$_2$O (1.34 g, 10 eq). The resulting mixture was stirred at r.t. for 8 h, after TLC showed the starting materials were consumed completely, then the mixture was diluted with water and adjusted pH to 3-4 with 1N HCl and the mixture was extracted with EtOAc, washed with brine, dried over anhydrous Na$_2$SO$_4$, concentrated and purified by prep-TLC to afford the desired intermediate I-20a (1.30 g, ~100%). ESI-MS (M+1): 425.2; calc. for C$_{23}$H$_{28}$N$_4$O$_4$: 424.2.

Preparation of Intermediate I-21a: (2,3,4,5,6-pentafluorophenyl) 3-[[4-ethoxy-3-(1-methyl-7-oxo-3-propyl-6H-pyrazolo[4,3-d]pyrimidin-5-yl)phenyl]methyl]cyclobutanecarboxylate To a solution of intermediate I-20a (850 mg, 2.0 mmol) and DIC (404 mg, 3.2 mmol) in CH$_2$Cl$_2$ (40 mL) was added the commercially available pentafluorophenol (386 mg, 2.1 mmol) at 0° C. under N$_2$. The mixture was stirred at r.t. overnight. After TLC showed the staring materials were consumed completely, and the mixture was extracted with EtOAc, washed with brine, dried over anhydrous Na$_2$SO$_4$, concentrated to give the crude product which was purified by column to give pure intermediate I-21a (720 mg, 61%) as a yellow solid. ESI-MS (M+1): 591.2; calc. for C$_{29}$H$_{27}$F$_5$N$_4$O$_4$.

Preparation of Compound 1-04: (racemic)N-(2-aminophenyl)-3-[[4-ethoxy-3-(1-methyl-7-oxo-3-propyl-6H-pyrazolo[4,3-d]pyrimidin-5-yl)phenyl]methyl]cyclobutanecarboxamide To a solution of intermediate I-21a (720 mg, 1.22 mmol) in DMF (40 mL) was added DIEA (348 mg, 2.7 mmol) and benzene-1,2-diamine (commercially available R-10a, 158 mg, 1.46 mmol). The mixture was stirred at 80° C. overnight until LC-MS showed the starting material was consumed completely, then quenched with water and extracted with EtOAc, the organic layer was washed with brine, dried over anhydrous $Na_2SO_4$, concentrated to give the crude product which was purified by prep-HPLC (General procedure, Method 2) to obtained pure compound 1-04 (330 mg, 52.7% yield), as a racemic mixture. ESI-MS (M+1): 515.3 calc. for $C_{29}H_{34}N_6O_3$: 514.2; Rt is 3.01

Preparation of Compounds 1-09 & 1-10: cis & trans N-(2-aminophenyl)-3-[[4-ethoxy-3-(1-methyl-7-oxo-3-propyl-6H-pyrazolo[4,3-d]pyrimidin-5-yl) phenyl]methyl]cyclobutanecarboxamide The cis and trans corresponding isomers were separated from the racemic mixture 1-04 (720 mg) by SFC (SFC method 1) to obtain cis isomers 1-09 (23 mg, 3.2%) ESI-MS (M+1): 515.2 calc. for $C_{29}H_{34}N_6O_3$: 514.2 (Rt is 3.36) and trans isomers 1-10 (25.1 mg, 3.5%) ESI-MS (M+1): 515.2 calc. for $C_{29}H_{34}N_6O_3$: 514.2 (Rt is 4.83).

Following the same synthetic route for compound 1-04 and using the same reagents unless otherwise indicated in the table below, the following compounds were obtained:

| Example | $R_t$ (min) | $[M + 1]^+$ | HPLC Method | Starting Materials and reagents |
|---|---|---|---|---|
| 1-16 | 2.75 | 507.3 | 2 | I-21a and piperazin-2-one (R-23) |
| 1-17 | 3.03 | 521.3 | 2 | I-21a and thiophene-3,4-diamine (R-22) |

Preparation of Intermediate I-19b: methyl 4-[[4-ethoxy-3-(1-methyl-7-oxo-3-propyl-6H-pyrazolo[4,3-d]pyrimidin-5-yl)phenyl]methyl]benzoate To a solution of intermediate I-13a (300 mg, 0.685 mmol) in 1,4-dioxane (20 mL) was added R-12a: methyl 4-(bromomethyl)benzoate (commercially available reagent, 142 mg, 0.623 mmol), $K_2CO_3$ (284 mg, 2.06 mmol in 1 mL water), $Pd(PPh_3)_4$ (722 mg, 0.0623 mmol), then the mixture was stirred at 80° C. overnight under $N_2$ protection. After LC-MS showed the starting material was consumed completely, the mixture was extracted with EtOAc, the organic layer was washed with brine, dried over anhydrous $Na_2SO_4$, concentrated to give the crude compound which was purified by Prep-TLC (PE/EtOAc=1:1) to give pure intermediate I-19b (148 mg, 51.93% yield) as a yellow solid. ESI-MS (M+1): 461 calc. for $C_{26}H_{28}N_4O_4$: 460.2.

Preparation of Intermediate I-20b: 4-[[4-ethoxy-3-(1-methyl-7-oxo-3-propyl-6H-pyrazolo[4,3-d]pyrimidin-5-yl)phenyl]methyl]benzoic acid To a solution of intermediate I-19b (148 mg, 0.32 mmol) in MeOH/THF/$H_2O$ (3/9/3, 15 mL) was added $LiOH.H_2O$ (135 mg, 3.2 mmol), the reaction mixture was stirred at rt overnight until LC-MS showed the starting material was consumed completely. Then concentrated, the mixture was diluted with $H_2O$ and adjusted pH to 1-2 with 1N HCl, then concentrated to give the crude intermediate I-20b (140 mg, 97.22%) as a yellow solid. ESI-MS (M+1): 447 calc. for $C_{25}H_{26}N_4O_4$: 446.1.

Preparation of 1-18: 4-[[4-ethoxy-3-(1-methyl-7-oxo-3-propyl-6H-pyrazolo[4,3-d]pyrimidin-5-yl) phenyl]methyl]-N-(methylcarbamoyl)benzamide A solution of intermediate I-20b (100 mg, 0.22 mmol) in $SOCl_2$ (10 mL) was stirred at 80° C. for 3 hours. Then, the mixture was concentrated under vacuum to give the crude intermediate 4-[[4-ethoxy-3-(1-methyl-7-oxo-3-propyl-6H-pyrazolo[4,3-d]pyrimidin-5-yl)phenyl]methyl]benzoyl chloride. To a solution of this intermediate in $CH_3CN$ (10 mL) was added methylurea (71.7 mg, 0.97 mmol), and DIEA (75 mg, 0.58 mmol). And te mixture was stirred at 80° C. overnight. Then, the reaction was quenched with water and extracted with EtOAc. The organic layer was washed with brine, dried over anhydrous $Na_2SO_4$ and concentrated to give the crude product which was purified by prep-HPLC (General procedure, Method 2) to obtain pure compound 1-18 (11.5 mg, 12.1% yield) as a yellow solid. ESI-MS (M+1): 503.3 calc. for $C_{27}H_{30}N_6O_4$; Rt is 2.93.

Preparation of Intermediate I-21b: (2,3,4,5,6-pentafluorophenyl) 4-[[4-ethoxy-3-(1-methyl-7-oxo-3-propyl-6H-pyrazolo[4,3-d]pyrimidin-5-yl)phenyl] methyl]benzoate To a solution of intermediate I-20b (220 mg, 0.38 mmol) and pentafluorophenol (77 mg, 0.42 mmol) in $CH_2Cl_2$ (20 mL) was added DIC (76 mg, 0.61 mmol) at 0° C. under $N_2$. The mixture was stirred at r.t. for 6 h. After TLC showed the staring materials were consumed completely, and the mixture was extracted with EtOAc, washed with brine, dried over anhydrous $Na_2SO_4$, concentrated to give the crude intermediate I-21b (200 mg, 75%) which was purified by prep-TLC as a yellow solid. ESI-MS (M+1): 613.2 calc. for $C_{31}H_{25}F_5N_4O_4$: 612.2

Preparation of Compound 1-11: N-(2-aminophenyl)-4-[[4-ethoxy-3-(1-methyl-7-oxo-3-propyl-6H-pyrazolo[4,3-d]pyrimidin-5-yl)phenyl]methyl]benzamide To a solution of intermediate I-21b (200 mg, 0.32 mmol) in DMF (5 mL) was added benzene-1,2-diamine (commercially available R-10a, 69.3 mg, 0.64 mmol), DIEA (52 mg, 0.40 mmol) and DMAP (44 mg, 0.36 mmol) at r.t, then the mixture was stirred at 60° C. overnight. The mixture was quenched with aqueous water and extracted with EtOAc, the organic layer was washed with brine, dried over anhydrous $Na_2SO_4$, concentrated to give the crude product which was purified by prep-TLC to give the compound 1-11 (36.7 mg, 22%) as a pale yellow solid. ESI-MS (M+1): 537.3; calc. for $C_{31}H_{32}N_6O_3$: 536.2. Rt is 3.20.

Preparation of Intermediate I-22a: tert-butyl N-[2-[[4-[[4-ethoxy-3-(1-methyl-7-oxo-3-propyl-6H-pyrazolo[4,3-d]pyrimidin-5-yl)phenyl]methyl]benzoyl] amino]-4-(2-thienyl)phenyl]carbamate The mixture of I-20b (150.00 mg, 335.95 umol, 1.00 eq) in $SOCl_2$ (399.68 mg, 3.36 mmol, 10.00 Eq) was stirred at 80° C. for 2 h. LCMS (TLC) showed the reaction was completed. The mixture was concentrated in reduced pressure at 45° C. The residue was dissolved in DCM (5 mL) and dropwise to a solution of tert-Butyl (2-amino-4-(thiophen-2-yl)phenyl)carbamate (R21a, 97.55 mg, 335.95 umol, 1.00 eq) and TEA (67.99 mg, 671.90 umol, 2.00 Eq) in DCM (5 mL) at 25° C. LCMS (TLC) showed the reaction was completed. The mixture was concentrated and purified by TLC to afford the intermediate I-22a (200.00 mg, crude).

Preparation of Compound 1-13: N-[2-amino-5-(2-thienyl)phenyl]-4-[[4-ethoxy-3-(1-methyl-7-oxo-3-propyl-6H-pyrazolo[4,3-d]pyrimidin-5-yl)phenyl] methyl]benzamide The mixture of I-22a (200.00 mg, 278.22 umol, 1.00 Eq) in HCl/EtOAc (4 N, 5 mL) was stirred at 25° C. for 16 hours.

LCMS showed the reaction was completed. The mixture was concentrated in reduced pressure at 40° C. and purified by prep-HPLC (method 2) to obtained pure compound 1-13 (12.00 mg, 19.39 umol, 6.97% yield) as white solid. ESI-MS (M+1):619.3 calc. for $C_{35}H_{34}N_6O_3S$: 618.2. Rt is 2.82

Following the same synthetic route for compound 1-11 or 1-13 and using the same reagents unless otherwise indicated in the table below, the following compounds were obtained:

| Example | $R_t$ (min) | $[M + 1]^+$ | HPLC Method | Starting Materials |
|---|---|---|---|---|
| 1-08 | 3.41 | 543.2 | 3 | I-13a and ethyl 5-(bromomethyl)thiophene-2-carboxylate (R12b)/benzene-1,2-diamine (R10a) |
| 1-14 | 2.36 | 555.3 | 2 | I-13a and methyl 4-(bromomethyl)benzoate (R-12a)/tert-Butyl N-(2-amino-4-fluorophenyl)carbamate (R-21b) |
| 1-19 | 2.46 | 529.3 | 2 | I-13a and methyl 4-(bromomethyl)benzoate (R12a)/piperazin-2-one (R-23) |
| 1-20 | 3.16 | 543.3 | 2 | I-13a and methyl 4-(bromomethyl)benzoate (R12a)/methyl 4-(bromomethyl)benzoate (R-22) |

Synthetic Route 1d

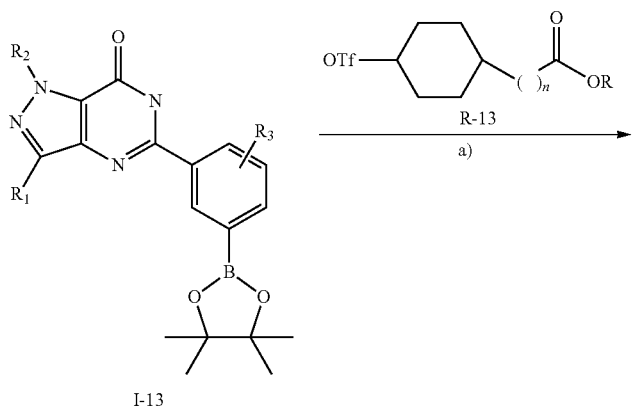

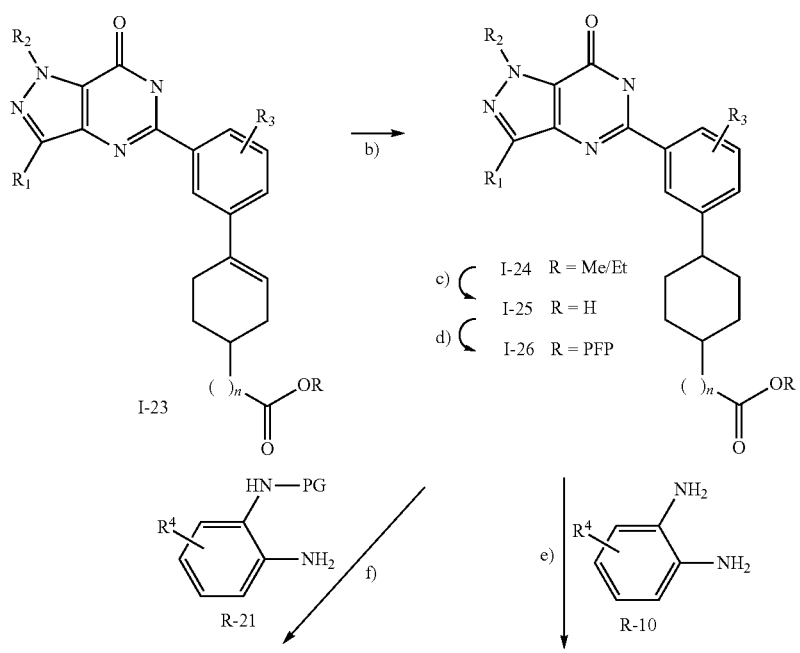

-continued

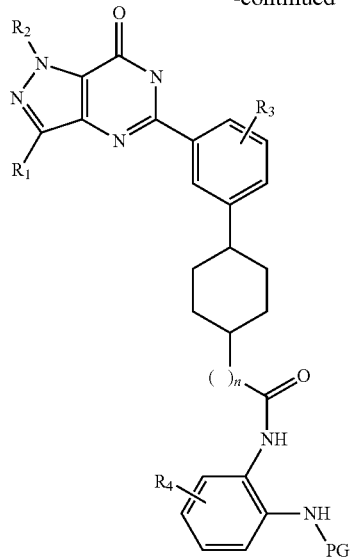

I-27

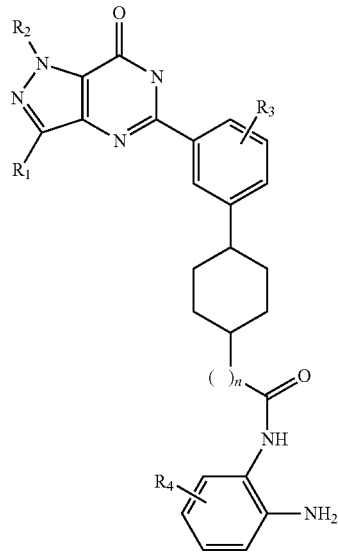

I-Ac

Conditions: a) R-13 (1 eq), Pd(PPh₃)₄ (0.1 eq) K₂CO₃ (3 eq) in water, in 1,4-dioxane, overnight at 80° C.;
b) Pd/C in MeOH at H₂ atmosphere, at r.t. for 1 hour; c) LiOH·H₂O (5 eq) in THF/methanol/H₂O, overnight at r.t.; d) PFP (1 eq), DIC (1.6 eq) in CH₂Cl₂, overnight at r.t.; e) R-10 (1.1 eq) and DIEA (2.1 eq) in DMF at 60° C.-80° C. overnight; f) SOCl₂ (3.3 eq) at 80° C. for 2 hours; then, TEA (2 eq) and R-21 (1 eq) in CH₂Cl₂ at r.t.; g) HCl/EtOAc (4N), 16 hours at r.t.

In the scheme above R is ($C_1$-$C_6$)alkyl and n is 0 or 1.

Preparation of Intermediate I-23a: ethyl 4-[4-ethoxy-3-(1-methyl-7-oxo-3-propyl-6H-pyrazolo[4,3-d]pyrimidin-5-yl)phenyl]cyclohex-3-ene-1-carboxylate To a solution of intermediate I-13a (300 mg, 0.685 mmol) in 1,4-dioxane (20 mL) was added R-13a: ethyl 4-(trifluoromethylsulfonyloxy)cyclohex-3-ene-1-carboxylate (207 mg, 0.685 mmol), K₂CO₃ (284 mg, 2.06 mmol in 1 mL water), Pd(PPh₃)₄ (80 mg, 0.0685 mmol), then the mixture was stirred at 80° C. overnight under N₂ protection. After LC-MS showed the starting material was consumed completely, the mixture was extracted with EtOAc, the organic layer was washed with brine, dried over anhydrous Na₂SO₄, concentrated to give the crude compound which was purified by Prep-TLC (PE/EtOAc=1:1) to give pure intermediate I-23a (300 mg, 94% yield) as a white solid. ESI-MS (M+1): 465 calc. for $C_{26}H_{32}N_4O_4$: 464.2.

Preparation of Intermediate I-24a: ethyl 4-[4-ethoxy-3-(1-methyl-7-oxo-3-propyl-6H-pyrazolo[4,3-d]pyrimidin-5-yl)phenyl]cyclohexanecarboxylate To a solution of intermediate I-23a (170 mg, 0.366 mmol) in MeOH (20 mL) was added Pd/C (50 mg) at H2 atmosphere, then the mixture was stirred at room temperature for 1 h until LC-MS showed the starting material was consumed completely, then filtered, the filtrate was concentrated to give the crude intermediate I-24a (154 mg, 90%) as a white solid which was used for the next step directly. ESI-MS (M+1): 467 calc. for $C_{26}H_{34}N_4O_4$: 466.2.

Preparation of Intermediate I-25a: 4-[4-ethoxy-3-(1-methyl-7-oxo-3-propyl-6H-pyrazolo[4,3-d]pyrimidin-5-yl)phenyl]cyclohexanecarboxylic acid To a solution of crude intermediate I-24a (154 mg, 0.330 mmol) in MeOH/THF/H₂O (3/9/3, 15 mL) was added LiOH·H₂O (139 mg, 3.30 mmol), the reaction mixture was stirred at room temperature overnight until LC-MS showed the starting material was consumed completely. Then concentrated, the mixture was diluted with H₂O and adjusted pH to 1-2 with 1N HCl, extracted with EtOAc, the organic layer was washed with brine, dried over anhydrous Na₂SO₄, concentrated to give the crude intermediate I-25a (110 mg, 75%) as a yellow solid. ESI-MS (M+1): 439 calc. for $C_{24}H_{30}N_4O_4$: 438.2.

Preparation of Intermediate I-26a: (2,3,4,5,6-pentafluorophenyl) 4-[4-ethoxy-3-(1-methyl-7-oxo-3-propyl-6H-pyrazolo[4,3-d]pyrimidin-5-yl)phenyl]cyclohexanecarboxylate To a solution of intermediate I-25a (520 mg, 1.19 mmol) and DIC (227 mg, 1.80 mmol) in CH₂Cl₂ (50 mL) was added pentafluorophenol (263 mg, 1.43 mmol) at 0° C. under N₂. The mixture was stirred at r.t. overnight. After TLC showed the staring materials were consumed completely, and the mixture was extracted with EtOAc, washed with brine, dried over anhydrous Na₂SO₄, concentrated to give the crude product which was purified by column to give pure intermediate I-26a (540 mg, 75%). ESI-MS (M+1): 605.2; calc. for $C_{30}H_{29}F_5N_4O_4$: 604.2

Preparation of Compounds 1-05, 1-06 & 1-07: racemic, cis & trans N-(2-aminophenyl)-4-[4-ethoxy-3-(1-methyl-7-oxo-3-propyl-6H-pyrazolo[4,3-d]pyrimidin-5-yl)phenyl]cyclohexanecarboxamide To a solution of intermediate I-26a (540 mg, 0.89 mmol) in DMF (40 mL) was added DIEA (310 mg, 2.4 mmol) and benzene-1,2-diamine (commercially available R10a, 113 mg, 1.05 mmol). The mixture was stirred at 80° C. overnight until LC-MS showed the starting material was consumed completely, then quenched with water and extracted with EtOAc, the organic layer was washed with brine, dried over anhydrous $Na_2SO_4$, concentrated to give the crude product which was purified by prep-HPLC (General procedure, Method 2) to obtained pure racemic compound 1-05 (21.2 mg) where ESI-MS (M+1): 529.2. calc. for $C_{30}H_{36}N_6O_3$: 528.3 (Rt is 3.30), cis isomer 1-06 (12.3 mg) where ESI-MS (M+1): 529.3. calc. for $C_{30}H_{36}N_6O_3$: 528.3 (Rt is 3.15) and trans isomer 1-07 (16.8 mg) where ESI-MS (M+1): 529.3. calc. for $C_{30}H_{36}N_6O_3$: 528.3 (Rt is 3.21).

Synthetic Route 1e

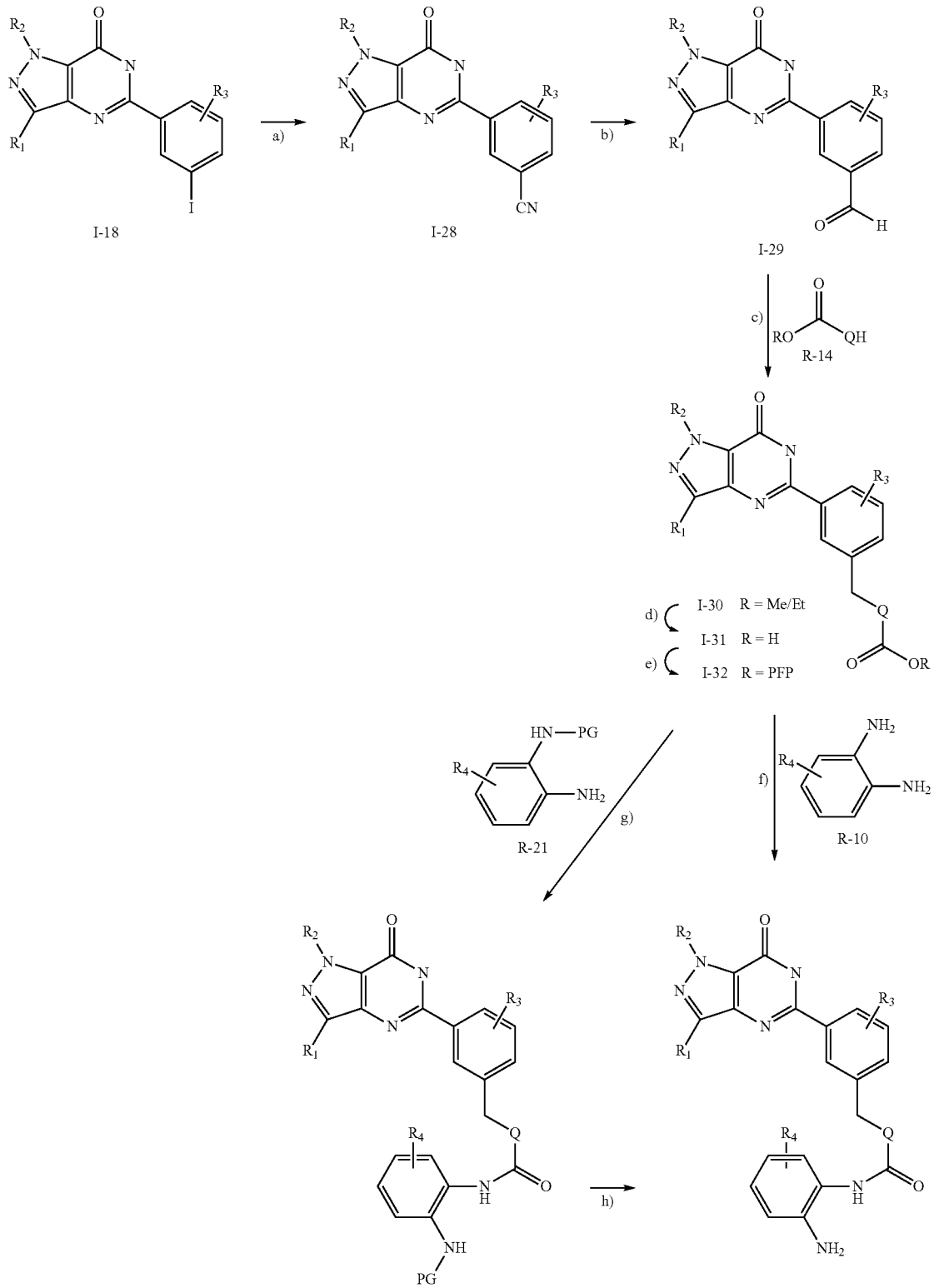

-continued

Conditions: a) Zn(CN)₂ (2 eq), Pd(PPh₃)₄ (0.1 eq) in DMF overnight at 80° C.; b) DIBAL-H (1.1 eq) in DCM, overnight at r.t.; c) R-14 (2.0 eq), AcOH (cat) and Na(AcO)₃BH (3.0 eq)in DCM overnight at r.t; d) LiOH·H₂O (10 eq) in THF/methanol/H₂O, overnight at r.t.; e) PFP (1.2 eq), DIC (1.6 eq) in CH₂Cl₂, overnight at r.t.; f) R-10 (2.0 eq), DMAP (1.2 eq) and DIEA (1.2 eq) in DMF at 60° C. overnight; g) SOCl₂ (3.3 eq) at 80° C. for 2 hours; then, TEA (2 eq) and R-21 (1 eq) in CH₂Cl₂ at r.t.; h) HCl/EtOAc (4N), 16 hours at r.t.

In the scheme above R is (C₁-C₆)alkyl and Q is NH or

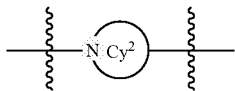

wherein Cy² is an heterocyclic ring.

Preparation of Intermediate I-28a: 4-ethoxy-3-(1-methyl-7-oxo-3-propyl-6H-pyrazolo[4,3-d]pyrimidin-5-yl)benzonitrile To a solution of intermediate I-18a (4.0 g, 9.13 mmol) in DMF (30 mL) was added Zn(CN)₂ (2.21 g, 18.26 mmol), Pd(PPh₃)₄ (1.06 g, 0.913 mmol), then the mixture was stirred at 80° C. overnight under N₂ protection. After LC-MS showed the starting material was consumed completely, the mixture was extracted with EtOAc, the organic layer was washed with brine, dried over anhydrous Na₂SO₄, concentrated to give the crude compound which was purified by column chromatography to give pure of intermediate I-28a (2.50 g, 81% yield) as a white solid. ESI-MS (M+1): 338 calc. for C₁₈H₁₉N₅O₂: 337.1.

Preparation of Intermediate I-29a: 4-ethoxy-3-(1-methyl-7-oxo-3-propyl-6H-pyrazolo[4,3-d]pyrimidin-5-yl)benzaldehyde To a solution of intermediate I-28a (2.50 g, 7.42 mmol) in anhydrous DCM (30 mL) was added diisobutylaluminium hydride (DIBAL-H) (8.2 mL, 1.0 M in toluene, 8.16 mmol) slowly at 0° C., then the mixture was stirred at room temperature overnight under N2 protection until HPLC showed the starting material was consumed completely, the mixture was poured into 2N HCl, extracted with DCM, the organic layer was washed with brine, dried over anhydrous Na₂SO₄, concentrated to give the crude compound which was purified by column chromatography to give pure intermediate I-29a (1.69 g, 67% yield) as a white solid. ESI-MS (M+1): 341 calc. for C₁₈H₂₀N₄O₃: 340.1.

Preparation of Intermediate I-30a: ethyl 1-[[4-ethoxy-3-(1-methyl-7-oxo-3-propyl-6H-pyrazolo[4,3-d]pyrimidin-5-yl)phenyl]methyl]azetidine-3-carboxylate To a solution of intermediate I-29a (1 g, 2.9 mmol) in anhydrous DCM (50 mL) was added ethyl azetidine-3-carboxylate (commercially available R14a, 755 mg, 5.9 mmol), AcOH (cat) and sodium triacetoxyborohydride (Na(AcO)₃BH) (1 g, 8.6 mmol), then the mixture was stirred at room temperature overnight until LC-MS showed the starting material was consumed completely, the mixture was extracted with DCM three times, the organic layer was washed with aqueous NaHCO₃, brine, dried over anhydrous Na₂SO₄, concentrated to give the crude compound which was purified by Prep-TLC (PE/EtOAc=1:1) to give pure intermediate I-30a (0.8 g, 67%) as a white solid. ESI-MS (M+1): 454 calc. for C₂₃H₂₉N₅O₄:453.2

Preparation of Intermediate I-31a: 1-[[4-ethoxy-3-(1-methyl-7-oxo-3-propyl-6H-pyrazolo[4,3-d]pyrimidin-5-yl)phenyl]methyl]azetidine-3-carboxylic acid To a solution of compound I-30a (800 mg, 1.8 mmol) in MeOH/THF/H2O (3/9/3, 15 mL) was added LiOH.H₂O (763 mg, 18 mmol), the reaction mixture was stirred at room temperature overnight until LC-MS showed the starting material was consumed completely. Then concentrated, the mixture was diluted with H₂O and adjusted pH to 1 2 with 1N HCl, extracted with EtOAc, the organic layer was washed with brine, dried over anhydrous Na₂SO₄, concentrated to give the crude intermediate I-31a (785 mg, 99%) as a white solid. ESI-MS (M+1): 426 calc. for C₂₂H₂₇N₅O₄: 425.2

Preparation of Intermediate I-32a: (2,3,4,5,6-pentafluorophenyl) 1-[[4-ethoxy-3-(1-methyl-7-oxo-3-propel-6H-pyrazolo[4,3-d]pyrimidin-5-yl)phenyl]methyl]azetidine-3-carboxylate To a solution of intermediate I-31a (350 mg, 0.82 mmol) and 2,3,4,5,6 pentafluorophenol (128 mg, 0.99 mmol) in CH₂Cl₂ (20 mL) was added DIC (180 mg, 1.31 mmol) at 0° C. under N₂. The mixture was stirred at r.t. for 6 h. After TLC showed the staring materials were consumed completely, and the mixture was extracted with EtOAc, washed with brine, dried over anhydrous Na₂SO₄, concentrated to give the crude intermediate I-32a (180 mg, 38%) which was purified by prep-TLC as a yellow solid. ESI-MS (M+1): 592 calc. for C₂₈H₂₆F₅N₅O₄: 591.2

Preparation of Compound 1-12: N-(2-aminophenyl)-1-[[4-ethoxy-3-(1-methyl-7-oxo-3-propyl-6H-pyrazolo[4,3-d]pyrimidin-5-yl)phenyl]methyl]azetidine-3-carboxamide To a solution of compound I-32a (180 mg, 0.30 mmol) in DMF (5 mL) was added benzene-1,2-diamine (commercially available R-10a, 65 mg, 0.60 mmol), DMAP (44 mg, 0.36 mmol) and DIEA (52 mg, 0.40 mmol) at r.t, then the mixture was stirred at 60° C. overnight. The mixture was quenched with aqueous water and extracted with EtOAc, the organic layer was washed with brine, dried over anhydrous Na₂SO₄, concentrated to give the crude product which was purified by prep-TLC to give the compound 1-12 (31 mg, 30%) as a pale yellow solid. ESI-MS (M+1): 516.2; calc. for C₂₈H₃₃N₇O₃: 515. Rt is 2.26.

Synthetic Route 1f

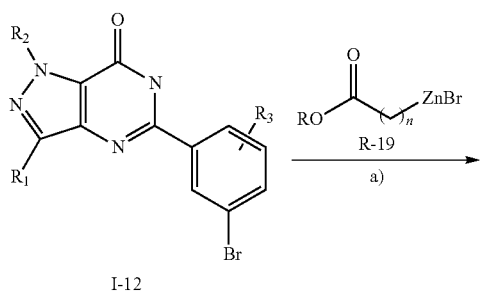

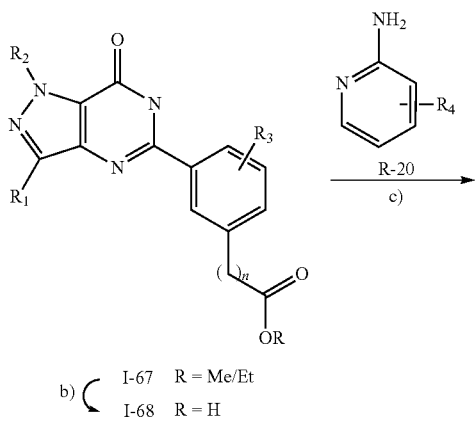

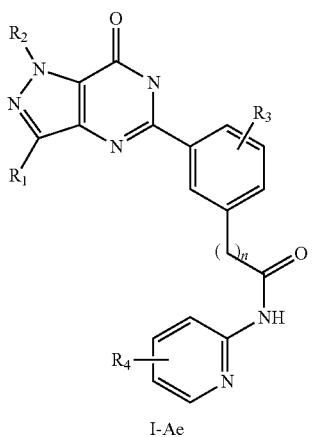

Conditions: a) R-19 (excess), Pd2(dba)3 (0.1 eq) and Xphos (0.2 eq) in THF overnight at 80° C.; b) LiOH•H2O (10 eq) in THF/methanol/H2O, overnight at r.t.; c) R-20 (1.1 eq), BOP (1.5 eq) and DIEA (3 eq) in DMF at 80° C. overnight In the scheme above n is 1, 2, 3 or 4.

Preparation of Intermediate I-67a: ethyl 2-[4-ethoxy-3-(1-methyl-7-oxo-3-propyl-6H-pyrazolo[4,3-d]pyrimidin-5-yl)phenyl]acetate To a solution of intermediate I-12a (500 mg, 1.282 mmol), Pd2(dba)3 (118 mg, 0.128 mmol), X-Phos (147 mg, 0.256 mmol) in anhydrous THF (30 mL) was added R-19a (20 mL, excess) under N2 protection, then the mixture was stirred at 80° C. overnight under $N_2$ protection until LC-MS showed the starting material was consumed completely, then the mixture was extracted with EtOAc and washed with brine, dried over anhydrous $Na_2SO_4$, concentrated to give the crude product which was purified by Prep-TLC (PE/EtOAc=1:1) to give pure intermediate I-67a (270 mg, 52.94%) as a white solid. ESI-MS (M+1): 399.3 calc. for $C_{21}H_{26}N_4O_4$: 398.2

Preparation of Intermediate I-68a: 2-[4-ethoxy-3-(1-methyl-7-oxo-3-propyl-6H-pyrazolo[4,3-d]pyrimidin-5-yl)phenyl]acetic acid To a solution of intermediate I-67a (270 mg, 0.678 mmol) in MeOH/THF/H2O (3/9/3, 15 mL) was added LiOH.H2O (285 mg, 6.78 mmol), the reaction mixture was stirred at room temperature overnight until LC-MS showed the starting material was consumed completely. Then concentrated, the mixture was diluted with $H_2O$ and adjusted pH to 1 2 with 1N HCl, extracted with EtOAc, the organic layer was washed with brine, dried over anhydrous Na2SO4, concentrated to give the crude intermediate I-68a (230 mg, 91.63%) as a white solid. ESI-MS (M+1): 371.2 calc. for $C_{19}H_{22}N_4O_4$: 370.2

Preparation of Compound 1-15: 2-[4-ethoxy-3-(1-methyl-7-oxo-3-propyl-6H-pyrazolo[4,3-d]pyrimidin-5-yl)phenyl]-N-(2-pyridyl)acetamide To a solution of intermediate I-68a (115 mg, 0.311 mmol) in DMF (10 mL) was added the commercially available pyridin-2-amine (R-20a, 32 mg, 0.342 mmol), BOP (206 mg, 0.467 mmol), DIEA (120 mg, 0.933 mmol). The mixture was stirred at 80° C. overnight until LC-MS showed the starting material was consumed completely, then quenched with water and extracted with EtOAc, the organic layer was washed with brine, dried over anhydrous $Na_2SO_4$, concentrated to give the crude product which was purified by Prep-HPLC (General procedure, Method 5) to give the pure compound 1-15 (10.5 mg, 7.55%) as a red solid. ESI-MS (M+1): 447.2 calc. for $C_{24}H_{26}N_6O_3$: 446.2. Rt is 2.43.

Synthetic Route 2a

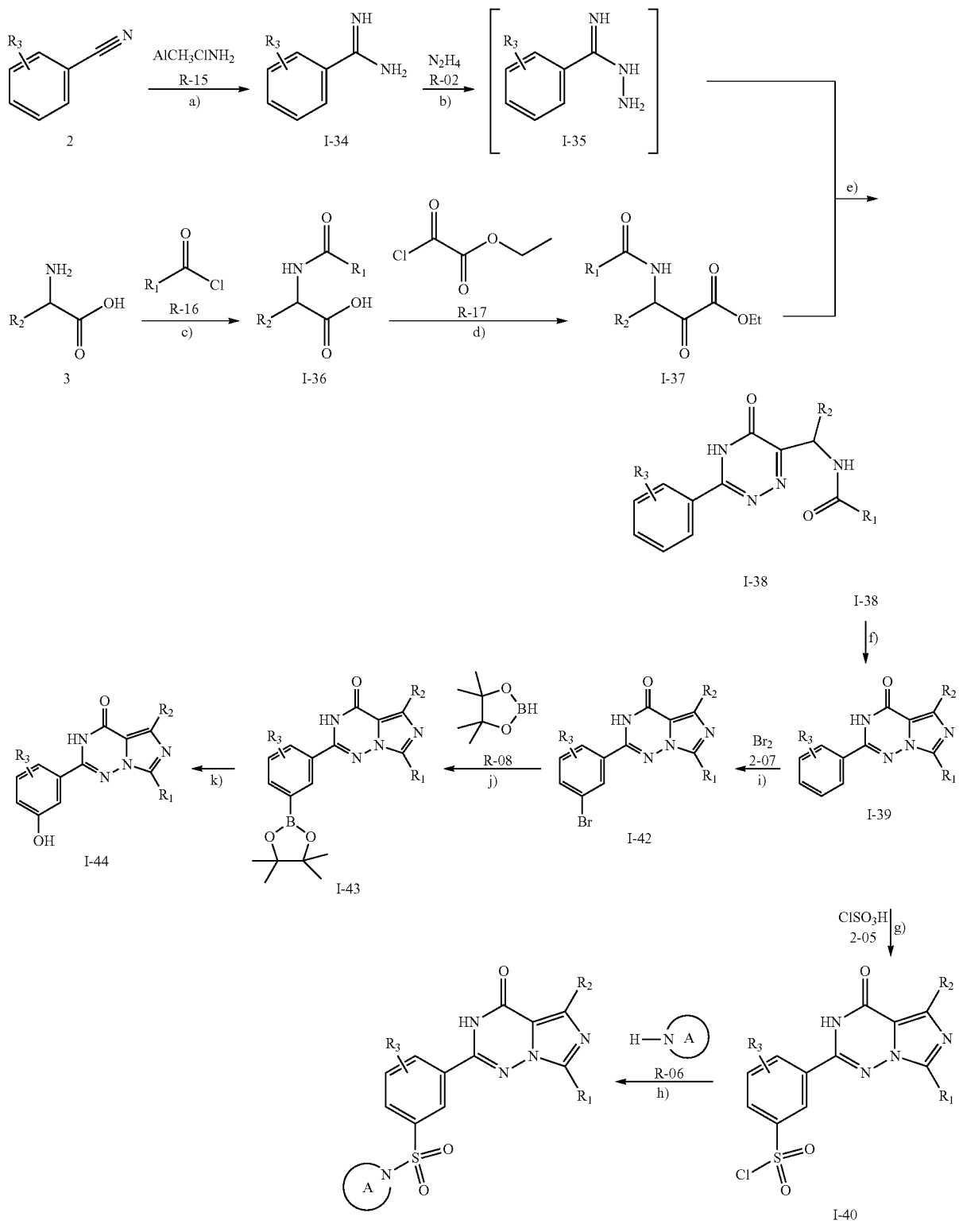

Conditions: a) R-15 obtained in-situ (NH₄Cl and Al(CH₃)₃ (2M) in toluene at 0° C., then rt 1 hour); then, 2 added and refluxed for 6 hours; b) N₂H₄•H₂O in ethanol at r.t.; c) R-16 (1.1 eq) added to 3 in NaOH 4 N (3 eq) solution at 0° C., then r.t. overnight; d) DMAP (cat.) and pyridine, in THF, at 55° C.; then, R-17 is added and refluxed for 4 hours; e) refluxed in ethanol for 3 hours; f) POCl₃ and 1,2-dichloroethane, 110° C. for 2 hours; g) ClSO₃H, r.t. for 2 hours; h) R-06 (2 eq) in ethanol, MW at 100° C. for 1 hour; i) Br₂ (1.2 eq) in AcOH overnight at r.t.; j) AcOK (2 eq), R-08 (1.2 eq) and (dppf)₂Cl₂Pd (0.1 eq), in dioxane, overnight at 90° C.; k) NaOH/H₂O (4M) and H₂O₂ (1.3 eq) in water overnight at r.t.

In the scheme above R is $(C_1-C_6)$alkyl, X is halogen, A is an optionally substituted 3- to 7-membered heterocyclic monocyclic ring.

Preparation of Intermediate I-34a: 2-Ethoxybenzamidine

To a solution of 2-ethoxybenzonitrile (2, 10 g, 68 mmol) in toluene (150 mL) was added $AlCH_3ClNH_2$ (1 eq). The methylchloroaluminum amide was freshly prepared, in-situ; $NH_4Cl$ (0.535 g, 10 mmol) was dissolved in dry toluene (10 mL) at 0° C. and trimethylaluminum (2 M in toluene, 5.0 mL, 10 mmol) was added and the reaction was warmed to r.t. and stirred for 1 hour to give the $AlCH_3ClNH_2$, which was used directly. The mixture was stirred at 80° C. for 6 hours. The reaction mixture was concentrated under vacuo to give crude I-34a (8.42 g, 75.4% yield). ESI-MS (M+1): 165 calc. for $C_9H_{12}N_2O$: 164.2.

Preparation of Intermediate I-36a: 2-Acetamidopentanoic acid

Butyryl chloride (R-16a, 9.6 g, 90 mmol) was added dropwise to a solution of D,L-alanine (3, 6.68 g, 75 mmol) in aqueous sodium hydroxide (7.2 g, 180 mmol) at about 5° C. to 10° C. The mixture was stirred overnight at r.t. The reaction mixture was extracted with DCM which was recovered to obtain crude I-36a as an oily residue (7.65 g, 64% yield). ESI-MS (M+1): 160 calc. for $C_7H_{13}NO_3$: 159.2.

Preparation of Intermediate I-37a: Ethyl 3-acetamido-2-oxohexanoate

Ethoxalyl chloride (R-17, 8.6 g, 63.0 mmol, 2 eq) was added dropwise with stirring to a solution of I-36a (5 g, 31.4 mmol), pyridine (5.15 g, 66 mmol, 2.1 eq), and DMAP (0.125 g, 1 mmol) in THF (200 mL). The reaction mixture was refluxed for 4 hours, cooled, diluted with water (100 mL) and extracted with EA. Ethyl acetate was recovered to obtain oily material. This crude was dissolved in ethanol (100 mL) and sodium bicarbonate (1.58 g, 18.8 mmol) was added. The contents were refluxed for 4 hours, cooled and sodium bicarbonate was removed by filtration. The mixture was concentrated to give the crude product which was purified by column chromatography with hexane:EA (3:1) to obtain I-37a (2.1 g, 31% yield). ESI-MS (M+1): 216 calc. for $C_{10}H_{17}NO_4$: 215.2.

Preparation of Intermediate I-38a: N-(1-(3-(2-ethoxyphenyl)-4,5-dihydro-5-oxo-1,2,4-triazin-6-yl)ethyl)butanamide To a solution of I-34a (1.11 g, 6.8 mmol) in ethanol (15 mL) was added a solution of hydrazine hydrate (0.345 g, 6.8 mmol) in ethanol (5 mL) over about 10 to 15 minutes. The reaction mixture was stirred at r.t. for 10 minutes. $MgSO_4$ (1 g) was added and the reaction mixture, where intermediate I-35 was generated and reacted without isolation, was heated to reflux. Then, a solution of I-37a (1.48 g, 6.8 mmol) in ethanol (10 mL) was added in about 15 minutes. The reaction mixture was refluxed for 3 hours. The mixture was concentrated to give the crude product which was purified by column chromatography to obtain the compound I-38a (638 mg, 28.4% yield). ESI-MS (M+1): 331 calc. for $C_{17}H_{22}N_4O_3$: 330.4.

Preparation of Intermediate I-39a: 2-(2-Ethoxyphenyl)-5-methyl-7-propyl-3H-imidazo[5,1-f][1,2,4]triazin-4-one To a solution of I-38a (456 mg, 1.38 mmol) in 1,2-dichloroethane (10 mL) was added $POCl_3$ (1.67 g, 11 mmol, 8 eq). The reaction was refluxed for 2 hours. The reaction mixture was cooled at r.t., diluted in DCM (20 mL) and neutralized by adding aqueous sodium hydroxide solution. The reaction mixture was extracted and concentrated under vacuo to give the crude product compound I-39a (169 mg, 39.2% yield). ESI-MS (M+1): 313 calc. for $C_{17}H_{20}N_4O_2$: 312.4.

Preparation of Intermediate I-40a: 4-Ethoxy-3-(5-methyl-4-oxo-7-propyl-3H-imidazo[5,1-f][1,2,4]triazin-2-yl)benzenesulfonyl chloride I-40a was obtained starting from I-39a in an analogous manner to I-10a. 80% yield. ESI-MS (M+1): 411 calc. for $C_{17}H_{19}ClN_4O_4S$: 410.08.

Preparation of Intermediate I-41a: 2-(2-Ethoxy-5-piperazin-1-ylsulfonylphenyl)-5-methyl-7-propyl-3H-imidazo[5,1-f][1,2,4]triazin-4-one I-41a was obtained starting from I-40a in an analogous manner to I-11a. 82.6% yield. ESI-MS (M+1): 461 calc. for $C_{21}H_{28}N_6O_4S$: 460.2.

Synthetic Route 2b

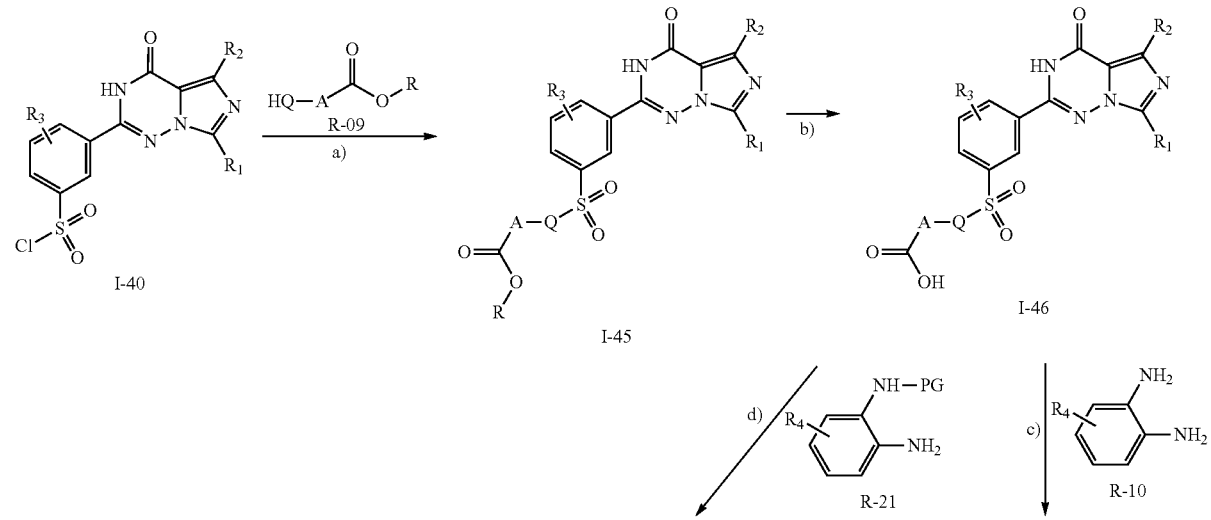

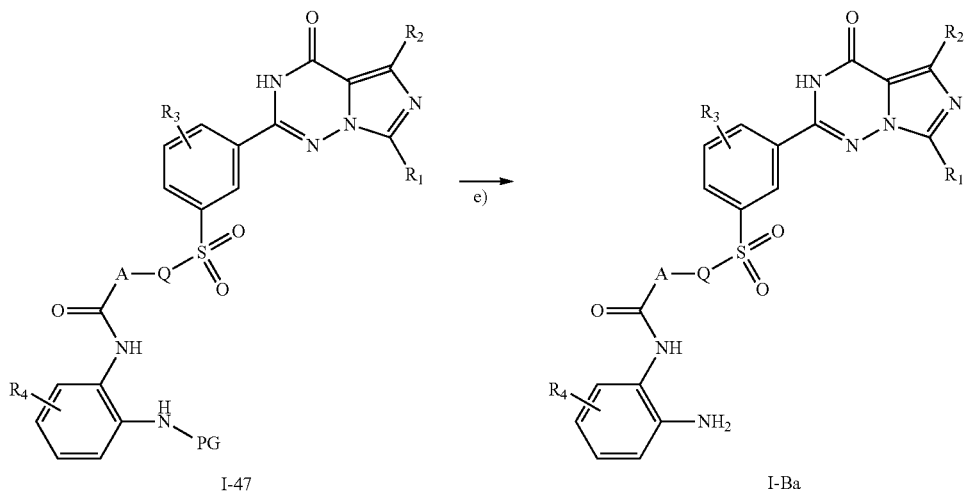

Conditions: a) Et₃N and R-09 in ethanol, MW at 100° C. for 2 hours; b) LiOH•H₂O (5 eq) in THF/methanol/H₂O, overnight at r.t.; c) EDC•HCl (1.2 eq), HOBt (1.2 eq), NMM (5 eq) and R-10 (1 eq) in DMF, overnight at r.t.; d) SOCl2 (3.3 eq) at 80° C. for 2 hours; then, TEA (2 eq) and R21 (1 eq) in CH2Cl2 at r.t.; e) HCl/EtOAc (4N), 16 hours at r.t.

In the scheme above R is $(C_1-C_6)$alkyl, Q is NH or

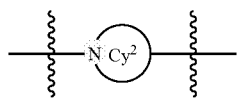

wherein $Cy^2$ is an heterocyclic ring, and A is a hydrocarbon chain, which optionally contains nitrogen, sulphur and/or oxygen atoms, and optionally contains one or more aromatic, heteroaromatic, carbocyclic and/or heterocyclic rings.

Preparation of Intermediate I-45a: ethyl 2-[4-[4-ethoxy-3-(5-methyl-4-oxo-7-propyl-3H-imidazo[5,1-f][1,2,4]triazin-2-yl)phenyl]sulfonylpiperazin-1-yl]pyrimidine-5-carboxylate I-45a was obtained starting from I-40a in an analogous manner to 1-15a, also using ethyl 2-(piperazin-1-yl)pyrimidine-5-carboxylate (R-09a). 66.6% yield. ESI-MS (M+1): 611 calc. for $C_{28}H_{34}N_8O_6S$: 610.3.

Preparation of Intermediate I-46a: 2-[4-[4-ethoxy-3-(5-methyl-4-oxo-7-propyl-3H-imidazo[5,1-f][1,2,4]triazin-2-yl)phenyl]sulfonylpiperazin-1-yl]pyrimidine-5-carboxylic acid I-46a was obtained starting from I-45a in an analogous manner to 1-16a. 78.7% yield. ESI-MS (M+1): 583 calc. for $C_{26}H_{30}N_8O_6S$: 582.20

Preparation of Compound 2-02: N-(2-aminophenyl)-2-[4-[4-ethoxy-3-(5-methyl-4-oxo-7-propyl-3H-imidazo[5,1-f][1,2,4]triazin-2-yl)phenyl]sulfonylpiperazin-1-yl]pyrimidine-5-carboxamide Compound 2-02 was obtained starting from I-46a in an analogous manner to compound 1-01. 63% yield. ESI-MS (M+1): ESI-MS (M+1): 673 calc. for $C_{32}H_{36}N_{10}O_5S$, 672.36; and, Rt is 2.24

Following the same synthetic route for compound 2-02 and using the same reagents unless otherwise indicated in the table below, the following compounds were obtained:

| Example | $R_t$ (min) | $[M + 1]^+$ | HPLC Method | Starting Materials |
|---|---|---|---|---|
| 2-01 | 2.14 | 616.1 | 4 | Methyl 4-(aminomethyl)benzoate (R-09d)/benzene-1,2-diamine (R10a) |
| 2-03 | 2.19 | 687.2 | 4 | Ethyl 2-(4-aminopiperidin-1-yl)pyrimidine-5-carboxylate (R-09b)/benzene-1,2-diamine (R10a) |

Synthetic Route 2c

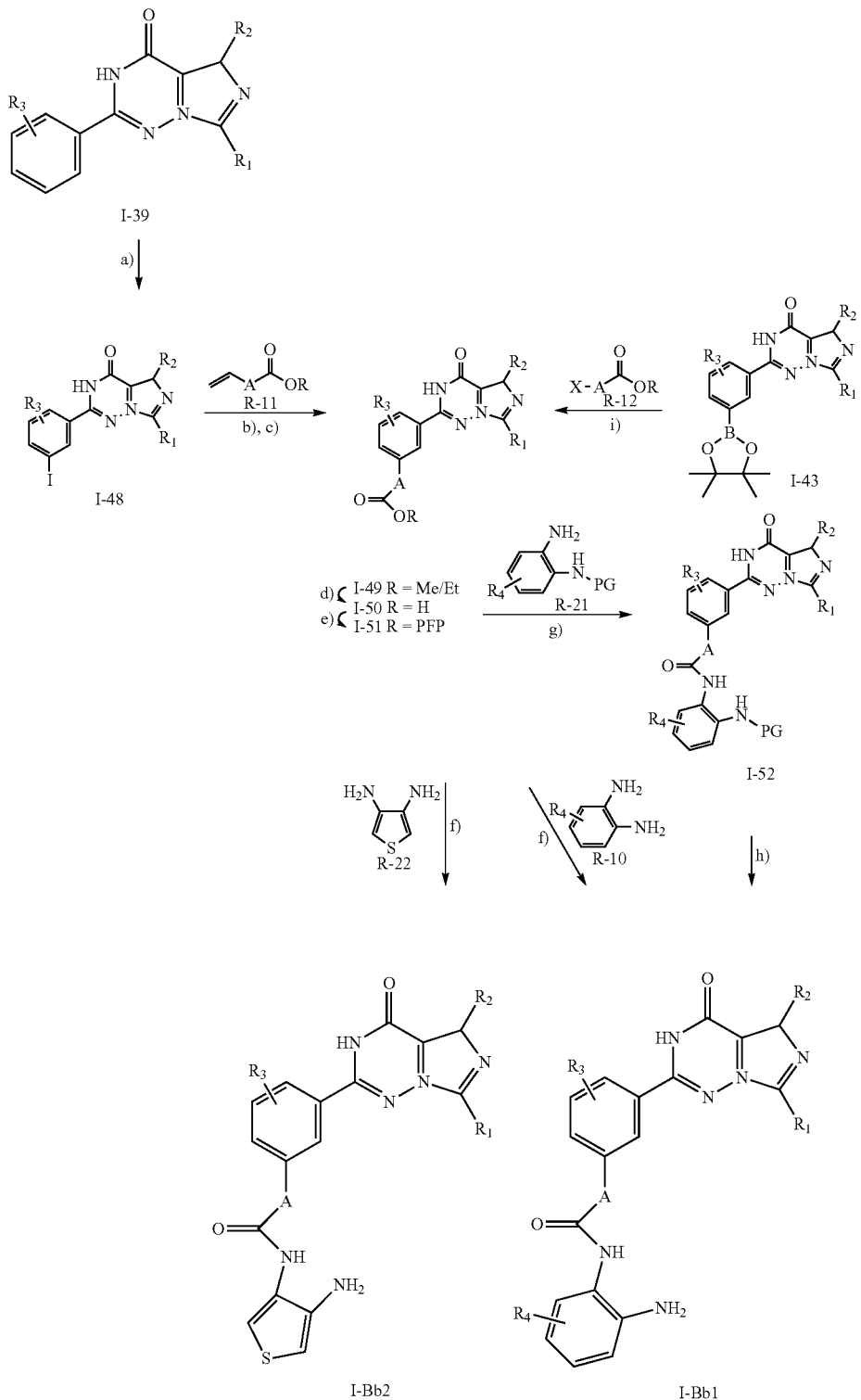

Conditions: a) NIS (1.2 eq), TFA, overnight at r.t.; b) R-11, 9-BBN (0.5M solution) in THF, reflux for 4 h; c) I-18, Pd₂(dba)₃ (0.1 eq), X-Phos (0.1 eq), Na₂CO₃ (3.0 eq), 1, 4-dioxane and H₂O, reflux overnight; d) LiOH•H₂O (10 eq) in THF/methanol/H₂O, overnight at r.t.; e) PFP (1.2 eq), DIC (1.6 eq) in Ch₂Cl₂, overnight at r.t.; f) R-10 or R-22 (1.1 eq), (DMAP (1.1 eq)) and DIEA (2.1 eq) in DMF at 60° C.-80° C. overnight; g) SOCl₂ (3.3 eq) at 80° C. for 2 hours; then, TEA (2 eq) and R21 (1 eq) in CH₂Cl₂ at r.t.; h) HCl/EtOAc (4N), 16 hours at r.t.; i) Na₂CO₃ (2 eq) in water, Pd(PPh₃)4 (0.1 eq) and R-12 (1.1 eq) in 1,4-dioxane, overnight at 80° C.

In the scheme above R is $(C_1-C_6)$alkyl and A is a hydrocarbon chain, which optionally contains nitrogen, sulphur and/or oxygen atoms, and optionally contains one or more aromatic, heteroaromatic, carbocyclic and/or heterocyclic rings.

Preparation of Intermediate I-48a: 2-(2-ethoxy-5-iodo-phenyl)-5-methyl-7-propyl-3H-imidazo[5,1-f][1,2,4]triazin-4-one To a solution of intermediate I-39a (5 g, 16 mmol) in TFA (50 mL) was added NIS (4.3 g, 19.2 mmol) at 0° C. The mixture solution was stirred at r.t. overnight. The mixture was quenched with aqueous water and extracted with EtOAc, the organic layer was washed with brine, dried over anhydrous $Na_2SO_4$, concentrated to give the crude product which was purified by the column to give intermediate I-48a (5 g, 79%) as a white solid. ESI-MS (M+1): 439.1; calc. for $C_{17}H_{19}IN_4O_2$: 438.0.

Preparation of Intermediate I-49a: ethyl 3-[[4-ethoxy-3-(5-methyl-4-oxo-7-propyl-3H-imidazo[5,1-f][1,2,4]triazin-2-yl)phenyl]methyl]cyclobutanecarboxylate Reagent ethyl 3-methylenecyclobutanecarboxylate R-11a (200 mg, 1.43 mmol) was treated with a 0.5 M solution of 9-BBN in THF (10 mL), and the mixture was heated at reflux for 4 h. The resulting mixture was transferred into a stirred mixture of intermediate I-48a (0.6 g, 1.37 mmol), $Pd_2(dba)_3$ (120 mg, 0.14 mmol), X-Phos (66 mg, 0.14 mmol), and $Na_2CO_3$ (454 mg, 4.2 mmol) in 1,4-dioxane (20 mL) and $H_2O$ (4 mL). The resulting mixture was stirred at reflux overnight. Then filtered, the mixture was extracted with EtOAc, the organic layer was washed with brine, dried over anhydrous $Na_2SO_4$, concentrated to give the crude compound which was purified by column chromatography (eluting with PE/EtOAc=50:1 to 5:1) to give pure intermediate I-49a (200 mg, 33% yield) as a pale yellow oil. ESI-MS (M+1): 453.2 calc. for $C_{25}H_{32}N_4O_4$: 452.2.

Preparation of Intermediate I-50a: 3-[[4-ethoxy-3-(5-methyl-4-oxo-7-propyl-3H-imidazo[5,1-f][1,2,4]triazin-2-yl)phenyl]methyl]cyclobutanecarboxylic acid To a solution of intermediate I-49a (200 mg, 0.44 mmol) in $THF/MeOH/H_2O$ (3/3/2, 16 mL) was added $LiOH \cdot H_2O$ (168 mg, 10 eq). The resulting mixture was stirred at r.t. for 8 h, after TLC showed the starting materials were consumed completely, then the mixture was diluted with water and adjusted pH to 6-7 with 1N HCl and the mixture was extracted with EtOAc, washed with brine, dried over anhydrous $Na_2SO_4$, concentrated to afford the desired intermediate I-50a (160 mg, 82%). ESI-MS (M+1): 425.2; calc. for $C_{23}H_{28}N_4O_4$.

Preparation of Intermediate I-51a: (2,3,4,5,6-pentafluorophenyl) 3-[[4-ethoxy-3-(5-methyl-4-oxo-7-propyl-3H-imidazo[5,1-f][1,2,4]triazin-2-yl)phenyl]methyl]cyclobutanecarboxylate To a solution of compound I-50a (1.40 g, 3.3 mmol) and DIC (630 mg, 5.0 mmol) in $CH_2Cl_2$ (50 mL) was added 2,3,4,5,6 pentafluorophenol (500 mg, 3.9 mmol) at 0° C. under $N_2$. The mixture was stirred at r.t. overnight. After TLC showed the staring materials were consumed completely, and the mixture was extracted with EtOAc, washed with brine, dried over anhydrous $Na_2SO_4$, concentrated to give the crude product which was purified by column to give pure intermediate I-51a (1.22 g, 64%) as a yellow solid. ESI-MS (M+1): 591.3; calc. for $C_{29}H_{27}F_5N_4O_4$: 590.2

Preparation of Compound 2-04: (racemic)N-(2-aminophenyl)-3-[[4-ethoxy-3-(5-methyl-4-oxo-7-propyl-3H-imidazo[5,1-f][1,2,4]triazin-2-yl)phenyl]methyl]cyclobutanecarboxamide To a solution of intermediate I-51a (1.22 g, 2.1 mmol) in DMF (40 mL) was added DIEA (440 mg, 3.4 mmol) and benzene-1,2-diamine (commercially available R-10a, 282 mg, 2.6 mmol). The mixture was stirred at 80° C. overnight until LC-MS showed the starting material was consumed completely, then quenched with water and extracted with EtOAc, the organic layer was washed with brine, dried over anhydrous Na2SO4, concentrated to give the crude product which was purified by prep-HPLC (Method 2) to obtained pure compound 2-04 (450 mg, 42%), a yellow solid, as a racemic mixture. ESI-MS (M+1): 515.3 calc. for $C_{29}H_{34}N_6O_3$: 514.2; Rt is 2.42.

Preparation of Compounds 2-05 & 2-06: cis & trans N-(2-aminophenyl)-3-[[4-ethoxy-3-(5-methyl-4-oxo-7-propyl-3H-imidazo[5,1-f][1,2,4]triazin-2-yl)phenyl]methyl]cyclobutanecarboxamide The cis and trans corresponding isomers were separated from the racemic mixture 2-04 (450 mg) by SFC (SFC method 1) to obtain cis isomers 2-05 (19.7 mg, 4.4%) ESI-MS (M+1): 515.3 calc. for $C_{29}H_{34}N_6O_3$: 514.2 (Rt is 2.25) and trans isomers 2-06 (12.4 mg, 2.8%) ESI-MS (M+1): 515.3 calc. for $C_{29}H_{34}N_6O_3$: 514.2 (Rt is 2.28).

Preparation of Intermediate I-49b: methyl 4-[[4-ethoxy-3-(5-methyl-4-oxo-7-propyl-3H-imidazo[5,1-f][1,2,4]triazin-2-yl)phenyl]methyl]benzoate To a solution of intermediate I-43a (500 mg, 1.14 mmol) in 1,4-dioxane/$H_2O$ (10:1, 33 mL) was added R-12a: methyl 4-(bromomethyl)benzoate (commercially available reagent, 287 mg, 1.25 mmol), $Na_2CO_3$ (242 mg, 2.28 mmol) and $Pd(PPh_3)_4$ (132 mg, 0.114 mmol) and the mixture was stirred at 85° C. for 1 h by MW. After LC-MS showed the starting material was consumed completely, the mixture was extracted with EtOAc, the organic layer was washed with brine, dried over anhydrous $Na_2SO_4$ and concentrated to give the crude compound which was purified by pre-TLC (PE/EtOAc=1:1) to give pure intermediate I-49b (300 mg, 57.14% yield) as a yellow solid. ESI-MS (M+1): 461.2 calc. for $C_{26}H_{28}N_4O_4$: 460.2.

Preparation of Intermediate I-50b: 4-[[4-ethoxy-3-(5-methyl-4-oxo-7-propyl-3H-imidazo[5,1-f][1,2,4]triazin-2-yl)phenyl]methyl]benzoic acid To a solution of intermediate I-49b (300 mg, 0.65 mmol) in $THF/MeOH/H_2O$ (3:3:2, 20 mL) was added $LiOH \cdot H_2O$ (274 mg, 6.5 mmol) and the resulting mixture was stirred at 25° C. for 12 hours. Then, the mixture was diluted with water and adjusted pH to 6-7 with 1N HCl. The mixture was extracted with EtOAc, washed with brine, dried over anhydrous $Na_2SO_4$ and concentrated to afford the desired intermediate I-50b (180 mg, yield 60.2%). ESI-MS (M+1): 447.2; calc. for $C_{25}H_{26}N_4O_4$: 446.1.

Preparation of Intermediate I-51b: (2,3,4,5,6-pentafluorophenyl) 4-[[4-ethoxy-3-(5-methyl-4-oxo-7-propyl-3H-imidazo[5,1-f][1,2,4]triazin-2-yl)phenyl]methyl]benzoate To a solution of intermediate I-50b (180 mg, 0.4 mmol) and DIC (153 mg, 1.21 mmol) in $CH_2Cl_2$ (10 mL) was added pentafluorophenol (111 mg, 0.6 mmol) at 0° C. under $N_2$. The mixture was stirred at 25° C. for 12 hours. After TLC (PE:EtOAc=1:1) showed the staring materials were consumed completely, and the mixture was concentrated to give the crude product which was purified by prep-TLC (PE:EtOAc=2:1) to obtain pure intermediate I-51 b (180.00 mg, 73% yield) as a pale yellow solid. ESI-MS (M+1): 613.2 calc. for $C_{31}H_{25}F_5N_4O_4$: 612.2.

Preparation of Compound 2-07: N-(4-amino-3-thienyl)-4-[[4-ethoxy-3-(5-methyl-4-oxo-7-propyl-3H-imidazo[5,1-f][1,2,4]triazin-2-yl)phenyl]methyl]benzamide To a solution of intermediate I-51 b (180 mg, 0.29 mmol) in DMF (10 mL) was added thiophene-3,4-diamine (R-22, 61 mg, 0.44 mmol), DMAP (1.5 mg, 0.029 mmol) and DIEA (75 mg, 0.58 mmol) at 25° C., then the mixture was stirred at 60° C. for 12 hours. Then, the mixture was concentrated to give the crude product which was purified by pre-HPLC (General procedure, Method 2) to obtain pure compound 2-07 (6 mg, 3.8% yield) as a yellow solid. ESI-MS (M+1): 543.3 calc. for $C_{29}H_{30}N_6O_3S$. Rt is 2.307
Synthetic Route 3a In the scheme above R is $(C_1-C_6)$alkyl. Any racemic mixture and pure enantiomer is considered.

Preparation of Intermediate I-53a:
5-amino-1-cyclopentyl-pyrazole-4-carbonitrile To a mixture of commercially available cyclopentylhydrazine hydrochloride (R-33a) (1.82 g, 18.18 mmol) and commercially available compound 4: (ethoxymethylene) malononitrile (1.34 g, 10.97 mmol) in EtOH (20 mL), was added $Et_3N$ (3.03 g, 29.93 mmol) in one portion at r.t. under $N_2$. The mixture was stirred at r.t. for 10 min. Then heated to 50° C. and stirred for 2 h. The mixture was cooled to r.t. and concentrated in reduced pressure. The residue was poured into water and the aqueous phase was extracted with EA (50 mL). The combined organic phase was washed with saturated brine (20 mL), dried with anhydrous $Na_2SO_4$, filtered and concentrated in vacuum. The residue was purified by silica gel chromatography to afford intermediate I-53a (1.22 g, 69% yield) as yellow solid. ESI-MS (M+1): 177.1 calc. for $C_9H_{12}N_4$: 176.1.

Preparation of Intermediate I-54a:
5-amino-1-cyclopentyl-pyrazole-4-carboxamide

To a mixture of intermediate I-53a (2.20 g, 12.48 mmol) in $CH_3CH_2OH$ (20 mL), was added H2O2 (4.24 g, 124.80 mmol) in one portion at r.t. under N2. Then $NH_3.H_2O$ (4.37 g, 124.80 mmol) was added dropwise. The mixture was stirred at r.t. for 2 h. HPLC (TLC) showed the reaction was completed. The residue was added $Na_2SO_3$ aq. (150 mL) and

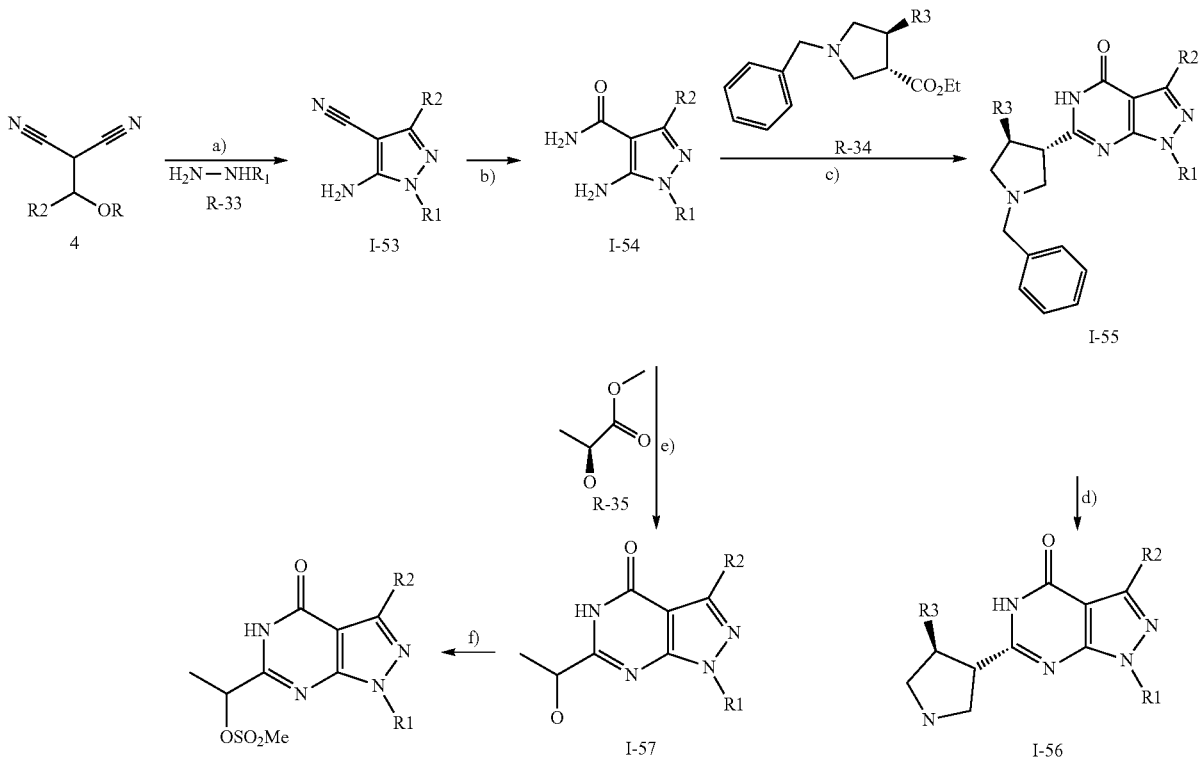

Conditions: a) R-33 (1.6 eq), Et3N (2 eq) in ethanol, 50° C., 2 hours; b) 30% $H_2O_2$ solution $NH_4OH$ (sat.) in ethanol, r.t. 2 hours; c) R-34, NaH, 120° C., MW, 1 hour; d) Pd/C in methanol at r.t. under 40 Psi at $H_2$ atmosphere during 5 hours; e) R-35 (enantiomerically pure, S; 3 eq) in ethanol and EtONa (2.7M), at 80° C overnight; f) Et3N (1.5 eq) and $CH_3SO_2Cl$ (1.1 eq) in DCM, at 0° C for 1 hour.

stirred for 2 h. The aqueous phase was extracted with EA (50 mL). The combined organic phase was washed with saturated brine (20 mL), dried with anhydrous $Na_2SO_4$, filtered and concentrated in vacuum. The residue was purified by silica gel chromatography to afford intermediate I-54a (1.54 g, 63% yield) as yellow solid. ESI-MS (M+1): 195.1 calc. For $C_9H_{14}N_4O$: 194.1.

Preparation of Intermediate I-55a: 6-(1-benzyl-4-methyl-pyrrolidin-3-yl)-1-cyclopentyl-5H-pyrazolo[3,4-d]pyrimidin-4-one (trans racemic To a solution of intermediate I-54a (1.3 g, 5.26 mmol) in EtOH (10 mL) was added ethyl 1-benzyl-4-methylpyrrolidine-3-carboxylate, trans racemic, R-34a (510 mg, 2.63 mmol) and NaH (631 mg, 26.3 mmol), then the reaction mixture was stirred at 120° C. for 1 h by MW. The mixture was quenched with water and extracted with EtOAc, the organic layer was washed with brine, dried over anhydrous $Na_2SO_4$, concentrated to give a reaction crude which was purified by column chromatography to give pure intermediate I-55a (685 mg, 69.0% yield) as a yellow solid. ESI-MS (M+1): 378.2 calc. for $C_{22}H_{27}N_5O$: 377.2.

Preparation of Intermediate I-56a: 1-cyclopentyl-6-(4-methylpyrrolidin-3-yl)-5H-pyrazolo[3,4-d]pyrimidin-4-one (trans racemic)

To a solution of intermediate I-55a (2 g, 5.3 mmol) in MeOH (10 mL) was added Pd/C (1 g), then the reaction mixture was stirred at r.t. 5 h at $H_2$ (40 psi) atmospheres. The mixture was filtrated and concentrated under vacuo, and extracted with EtOAc, the organic layer was washed with brine, dried over anhydrous $Na_2SO_4$, The mixture was concentrated to give intermediate I-56a (687 mg, 45.11% yield) as a yellow solid. ESI-MS (M+1): 288.2 calc. for $C_{15}H_{21}N_5O$: 287.2.

Preparation of Intermediate I-57a: 1-cyclopentyl-6-(1-hydroxyethyl)-5H-pyrazolo[3,4-d]pyrimidin-4-one To a solution of intermediate I-54a (3.0 g, 15.6 mmol) in anhydrous EtOH (100 mL) was added the commercially available (S)-methyl 2-hydroxypropanoate, (R-35, 5.36 g, 51.48 mmol) and EtONa (21.3 mL, 2.7 M, fresh), the reaction mixture was stirred at 80° C. for 12 h. Then the reaction mixture was concentrated under vacuo and purified by column (PE:EtOAc=10:1 to 1:1) to give the intermediate I-57a (3.5 g, yield: 68.47%, 30:70 enantiomers shown in SFC). ESI-MS (M+1): 249.2 calc. for $C_{12}H_{16}N_4O_2$:248.2

Preparation of Intermediate I-58a: 1-(1-cyclopentyl-4-oxo-5H-pyrazolo[3,4-d]pyrimidin-6-yl)ethyl methanesulfonate To a solution of intermediate I-57a (3.5 g, 14.1 mmol) in DCM (50 mL) was added $Et_3N$ (2.14 g, 21.15 mmol) and methanesulfonyl chloride (1.78 g, 15.51 mmol) slowly at 0° C. The reaction mixture was stirred for 1 h at 0° C. Then the reaction mixture was extracted by DCM and washed by water, dried by $Na_2SO_4$ and concentrated under vacuo and purified by column (PE:EtOAc=10:1 to 1:1) to give intermediate I-58a (2 g, 43.46%). ESI-MS (M+1): 327.2 calc. for $C_{13}H_{18}N_4O_4S$: 326.1.

Synthetic Route 3b

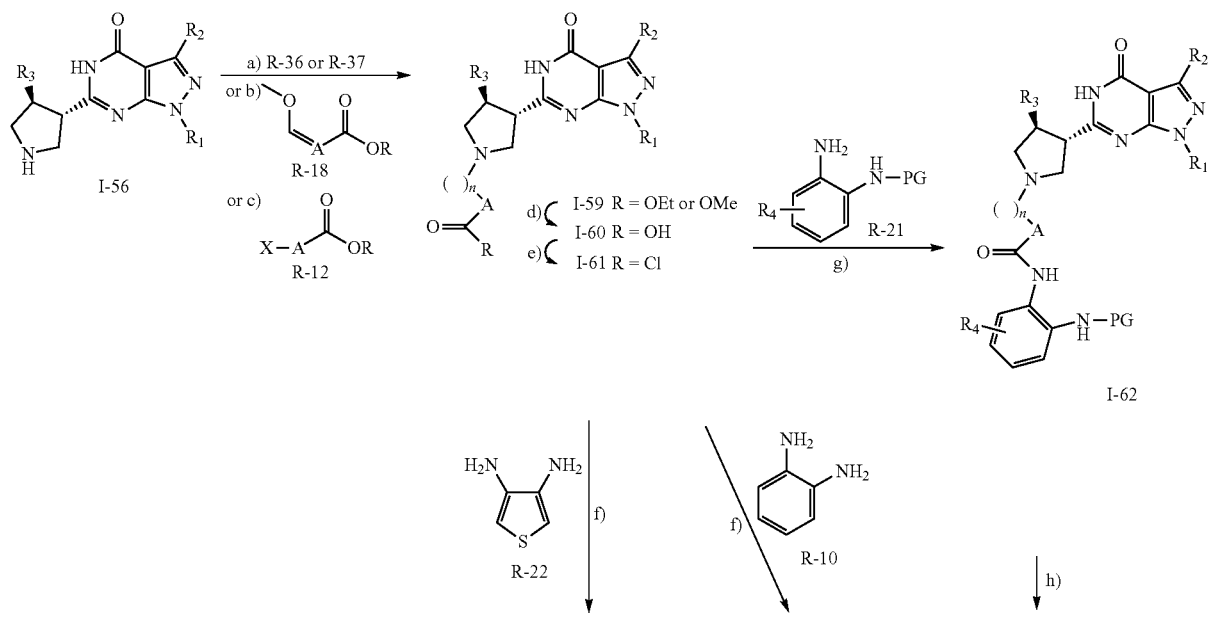

-continued

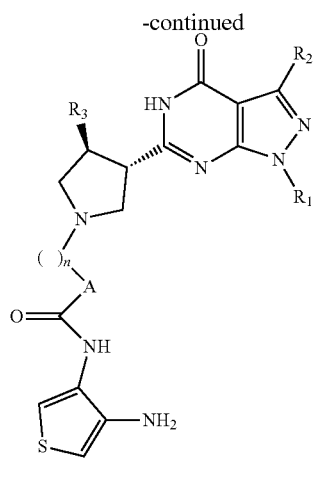

I-Ca2

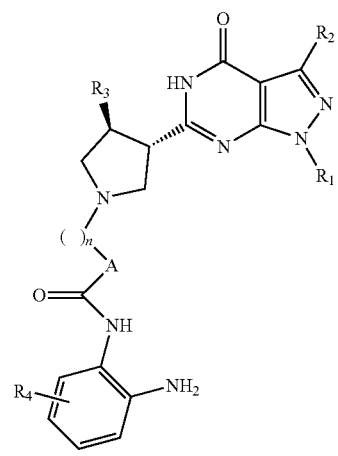

I-Ca1

Conditions: a) keton R-36 (1 eq) or aldehyde R-37 (1.2 eq), AcOH (cat), Na(AcO)₃BH (2 eq), DCM, overnight at r.t.; b) R-18 (1.5 eq), CH₃COOH (2 eq) in DCM at 0° C. for 3 h, Na(AcO)₃BH (2 eq), at r.t. for 15 h; c) K₂CO₃ (3 eq) and R-11 (1.5 eq) in CH₃CN, at 80° C. for 2-48 hours; d) LiOH·H₂O (10 eq) in THF/methanol/H₂O, overnight at r.t.; e) I-60 in SOCl₂ at r.t. for 1 hour; f) R-10 (1.1 eq), TEA (2.0 eq) in DCM at r.t. overnight; g) TEA (2 eq) and R21 (1.1 eq) in CH₂Cl₂ at r.t. for 12 hours; h) HCl/EtOAc (4N), 1 hour at r.t.

In the scheme above R is $(C_1-C_6)$alkyl, X is a leaving group, such halogen, and A is a hydrocarbon chain, which optionally contains nitrogen, sulphur and/or oxygen atoms, and optionally contains one or more aromatic, heteroaromatic, carbocyclic and/or heterocyclic rings. Any racemic mixture and pure enantiomer is considered.

Preparation of Intermediate I-59a: methyl 4-[[3-(1-cyclopentyl-4-oxo-5H-pyrazolo[3,4-d]pyrimidin-6-yl)-4-methylpyrrolidin-1-yl]methyl]benzoate (trans racemic)

To a solution of intermediate I-56a (300 mg, 1.04 mmol) in DCM (10 mL) was added the commercially available methyl 4-formylbenzoate (R-37a, 205.7 mg, 1.25 mmol), and the mixture was added CH₃COOH (0.1 mL). Then the mixture was stirred at r.t. for 1 h. Then the mixture was added NaBH(OAc)₃ (442.6 mg, 2.09 mmol), and stirred at r.t. overnight. After TLC (DCM/MeOH 10:1) showed the starting material was consumed, the mixture was filtrated and concentrated to give the crude product which was purified by prep-TLC to obtained pure intermediate I-59a (255 mg, 56.21% yield) as a yellow solid. ESI-MS (M+1): 436.2 calc. for $C_{24}H_{29}N_5O_3$: 435.2

Preparation of Intermediate I-60a: 4-[[3-(1-cyclopentyl-4-oxo-5H-pyrazolo[3,4-d]pyrimidin-6-yl)-4-methyl-pyrrolidin-1-yl]methyl]benzoic acid (trans racemic)

To a solution of intermediate I-59a (255 mg, 0.59 mmol) in THF/MeOH/H₂O (3/3/2, 10 mL) was added LiOH.H₂O (25 mg, 59 mmol). The resulting mixture was stirred at r.t. for 4 h, after TLC (DCM/MeOH 10:1) showed the staring materials were consumed completely, then the mixture was diluted with water and adjusted pH to 2-3 with 1 N HCl and the mixture was extracted with EtOAc, washed with brine, dried over anhydrous Na₂SO₄, concentrated to give the crude intermediate I-60a (231 mg, 93.6% yield) as a pale yellow solid which was used in the next step without purification. ESI-MS (M+1): 422.2 calc. for $C_{23}H_{27}N_5O_3$: 421.2.

Preparation of Intermediate I-61a: 4-[[3-(1-cyclopentyl-4-oxo-5H-pyrazolo[3,4-d]pyrimidin-6-yl)-4-methyl-pyrrolidin-1-yl]methyl]benzoyl chloride (trans racemic)

To a solution of intermediate I-60a (100 mg, 0.24 mmol) in CH₂Cl₂ (10 mL) was added (COCl)₂ (150 mg, 1.2 mmol) and DMF (0.1 mL) at −5° C. under N2. The mixture was stirred at r.t. for 1 h. The mixture was concentrated under vacuo to give the crude intermediate I-61a (100 mg, crude) used directly in next step. ESI-MS (M+1): 440.3 calc. for $C_{23}H_{26}ClN_5O_2$: 439.2.

Preparation of Compound 3-01: N-(2-aminophenyl)-4-[[(3S,4S)-3-(1-cyclopentyl-4-oxo-5H-pyrazolo[3,4-d]pyrimidin-6-yl)-4-methyl-pyrrolidin-1-yl]methyl] benzamide (trans racemic)

The crude intermediate I-61a (100 mg, 0.22 mmol) in CH₂Cl₂ (2 mL) was added to a solution of compound Et₃N (46 mg, 0.44 mmol) and benzene-1,2-diamine (commercially available R-10a, 30 mg, 0.28 mmol) dissolved in CH₂Cl₂ (10 mL) at 0° C. under N₂. The resulting mixture was stirred at r.t. overnight until TLC showed the starting material was consumed completely, the mixture was concentrated to give the crude compound which was purified by prep-HPLC (General procedure, Method 2) to obtained pure compound 3-01 (6 mg, 5.3% yield) as a yellow solid. ESI-MS (M+1):512.3 calc. for $C_{29}H_{33}N_7O_2$: 511.3. Rt is 2.70.

Following the same synthetic route for compound 3-01 and using the same reagents or intermediates unless otherwise indicated in the table below, the following compounds were obtained:

| Example | $R_t$ (min) | $[M + 1]^+$ | HPLC Method | Starting Materials and reagents |
|---|---|---|---|---|
| 3-05 (trans racemic) | 1.91 | 518.3 | 2 | I-61a/thiophene-3,4-diamine (R-22) |

Preparation of Intermediate I-62a: tert-butyl N-[2-[[4-[[3-(1-cyclopentyl-4-oxo-5H-pyrazolo[3,4-d]pyrimidin-6-yl)-4-methyl-pyrrolidin-1-yl]methyl]benzoyl]amino]-4-(2-thienyl)phenyl]carbamate (trans racemic)

The crude intermediate I-61a (50 mg, 0.12 mmol) in CH$_2$Cl$_2$ (2 mL) was added to a solution of compound Et$_3$N (24 mg, 0.24 mmol) and tert-Butyl (2-amino-4-(thiophen-2-yl)phenyl)carbamate (R21a, 41 mg, 0.14 mmol) dissolved in CH$_2$Cl$_2$ (10 mL) at 0° C. under N2. The resulting mixture was stirred at 25° C. for 12 hr until TLC (PE:EtOAc=1:1) showed the starting material was consumed completely, the mixture was concentrated to give the crude compound which was purified by prep-TLC (DCM:MeOH=10:1) to obtained pure intermediate I-62a (55 mg, 72% yield) as a yellow solid. ESI-MS (M+1): 694.3 calc. for C$_{38}$H$_{43}$N$_7$O$_4$S: 693.3

Preparation of Compound 3-02: N-[2-amino-5-(2-thienyl)phenyl]-4-[[3-(1-cyclopentyl-4-oxo-5H-pyrazolo[3,4-d]pyrimidin-6-yl)-4-methyl-pyrrolidin-1-yl]methyl]benzamide (trans racemic)

A solution of intermediate I-62a (20 mg, 0.03 mmol) in HCl/EtOAc (4 M, 10 mL) was stirred at 25° C. for 1 h then concentrated to give the crude compound which was purified by prep-HPLC (General procedure, Method 2) to obtained pure compound 3-02 (5.5 mg, 30.9% yield) as a yellow solid. ESI-MS (M+1):594.3 calc. for C33H35N$_7$O$_2$S: 593.2. Rt is 3.30.

Following the same synthetic route for compound 3-02 and using the same reagents or intermediates unless otherwise indicated in the table below, the following compounds were obtained:

| Example | R$_t$ (min) | [M + 1]$^+$ | HPLC Method | Starting Materials |
|---|---|---|---|---|
| 3-03 (trans racemic) | 2.87 | 530.2 | 2 | Methyl 4-formylbenzoate (R-37a)/tert-Butyl N-(2-amino-4-fluorophenyl)carbamate (R-21b |

Synthetic Route 3c

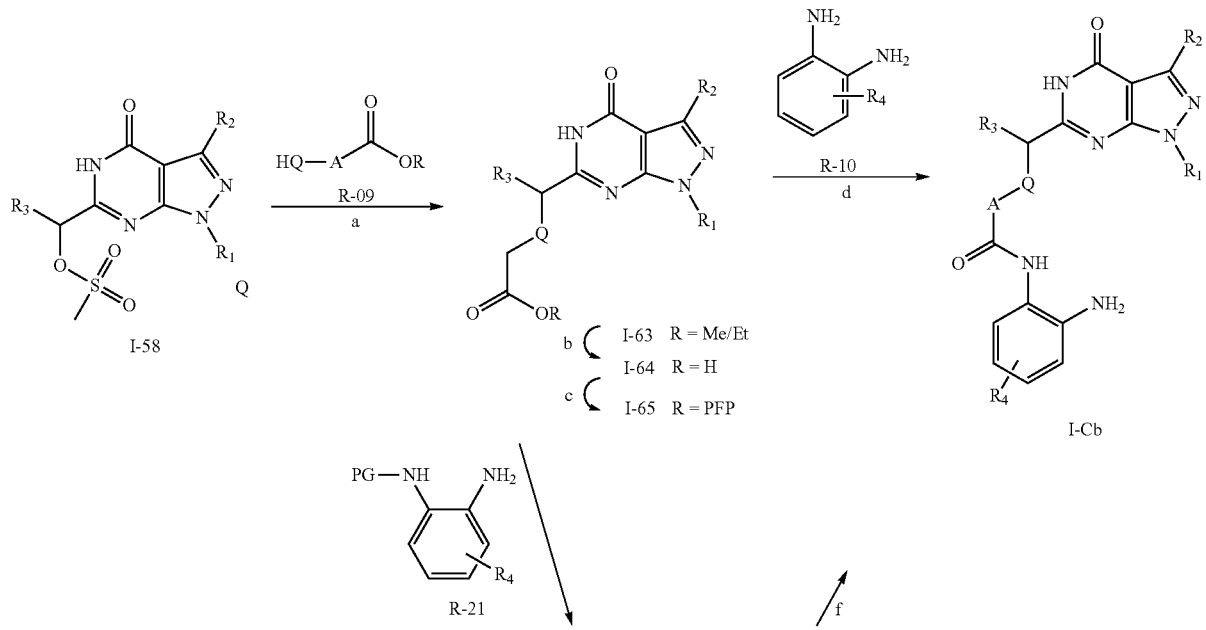

-continued

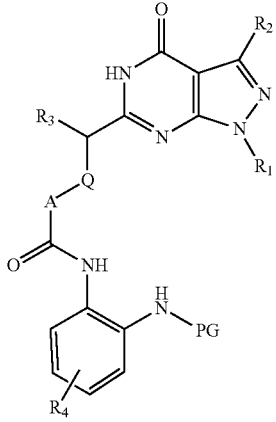

I-66

Conditions: a) Et₃N and R-09 in CH₃CN/toluene, at 110° C. for 2 hours; b) LiOH·H₂O (10 eq) in THF/methanol/H₂O, 4 hours at r.t.; c) PFP (1 eq), DIC (1.6 eq) in CH₂Cl₂, overnight at r.t.; d) R-10 (1.1 eq), TEA (2.0 eq) in DCM at r.t. overnight; e) TEA (2 eq) and R21 (1 eq) in CH2Cl2 at r.t.; f) HCl/EtOAc (4N), 16 hours at r.t.

In the scheme above R is $(C_1-C_6)$alkyl, Q is oxygen, NH or

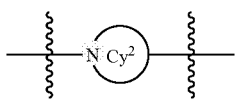

wherein $Cy^2$ is an heterocyclic ring, and A is a hydrocarbon chain, which optionally contains nitrogen, sulphur and/or oxygen atoms, and optionally contains one or more aromatic, heteroaromatic, carbocyclic and/or heterocyclic rings. Any racemic mixture and pure enantiomer is considered.

Preparation of Intermediate I-63a: ethyl 4-[[1-[1-(1-cyclopentyl-4-oxo-5H-pyrazolo[3,4-d]pyrimidin-6-yl)ethyl]azetidin-3-yl]methyl]benzoate To a solution of R-09e (160 mg, 0.73 mmol) in CH₃CN (5 mL) and toluene (5 mL) was added Et₃N (147 mg, 1.46 mmol) and intermediate I-58a (239 mg, 0.73 mmol). The reaction mixture was stirred at 110° C. by microwave for 2 h. After TLC (DCM/MeOH=10:1) showed the starting material was consumed, the mixture was concentrated to give the crude product which was purified by prep-TLC (DCM/MeOH=10:1) to obtained pure intermediate I-63a (110 mg, 33.5% yield) as a pale yellow solid. ESI-MS (M+1): 450.2 calc. for $C_{25}H_{31}N_5O_3$:449.2

Preparation of Intermediate I-64a: 4-[[1-[1-(1-cyclopentyl-4-oxo-5H-pyrazolo[3,4-d]pyrimidin-6-yl)ethyl]azetidin-3-yl]methyl]benzoic acid To a solution of intermediate I-63a (110 mg, 0.24 mmol) in THF/MeOH/H₂O (3/3/2, 20 mL) was added LiOH.H₂O (103 mg, 2.5 mmol). The resulting mixture was stirred at 25° C. for 4 h, after TLC (DCM/MeOH=10:1) showed the staring materials were consumed completely, then the mixture was diluted with water and adjusted pH to 2-3 with 1N HCl and the mixture was concentrated to give the crude intermediate I-64a (90 mg, 87.26% yield) as a pale yellow solid which was used in the next step without purification. ESI-MS (M+1): 422.2 calc. for $C_{23}H_{27}N_5O_3$: 421.2.

Preparation of Intermediate I-65a: (2,3,4,5,6-pentafluorophenyl) 4-[[1-[1-(1-cyclopentyl-4-oxo-5H-pyrazolo[3,4-d]pyrimidin-6-yl)ethyl]azetidin-3-yl] methyl]benzoate To a solution of intermediate I-64a (80 mg, 0.19 mmol) and DIC (34 mg, 0.28 mmol) in CH₂Cl₂ (10 mL) was added the commercially available pentafluorophenol (42 mg, 0.23 mmol) at 0° C. under N₂. The mixture was stirred at r.t overnight. After TLC (DCM/MeOH=10:1) showed the starting materials were consumed completely, and the mixture was concentrated to give the crude product which was purified by prep-TLC (DCM/MeOH=10:1) to obtained pure intermediate I-65a (75.00 mg, 60.53% yield) as a pale yellow solid. ESI-MS (M+1): 588.2 calc. for $C_{29}H_{26}F_5N_5O_3$: 587.2

Preparation of Compound 3-04: N-(2-aminophenyl)-4-[[1-[1-(1-cyclopentyl-4-oxo-5H-pyrazolo[3,4-d]pyrimidin-6-yl)ethyl]azetidin-3-yl]methyl]benzamide To a solution of intermediate I-65a (75 mg, 0.13 mmol) in DMF (10 mL) was added benzene-1,2-diamine (commercially available R-10a, 28 mg, 0.26 mmol), DMAP (1.56 mg, 0.012 mmol) and DIEA (33 mg, 0.26 mmol) at r.t, then the mixture was stirred at 60° C. overnight. The mixture was concentrated to give the crude product which was purified by pre-HPLC (General procedure, Method 2) to obtained pure compound 3-04 (10 mg, 15.1% yield) as a yellow solid. ESI-MS (M+1):512.2 calc. for $C_{29}H_{33}N_7O_2$. Rt is 1.78.

Synthetic Route 4a

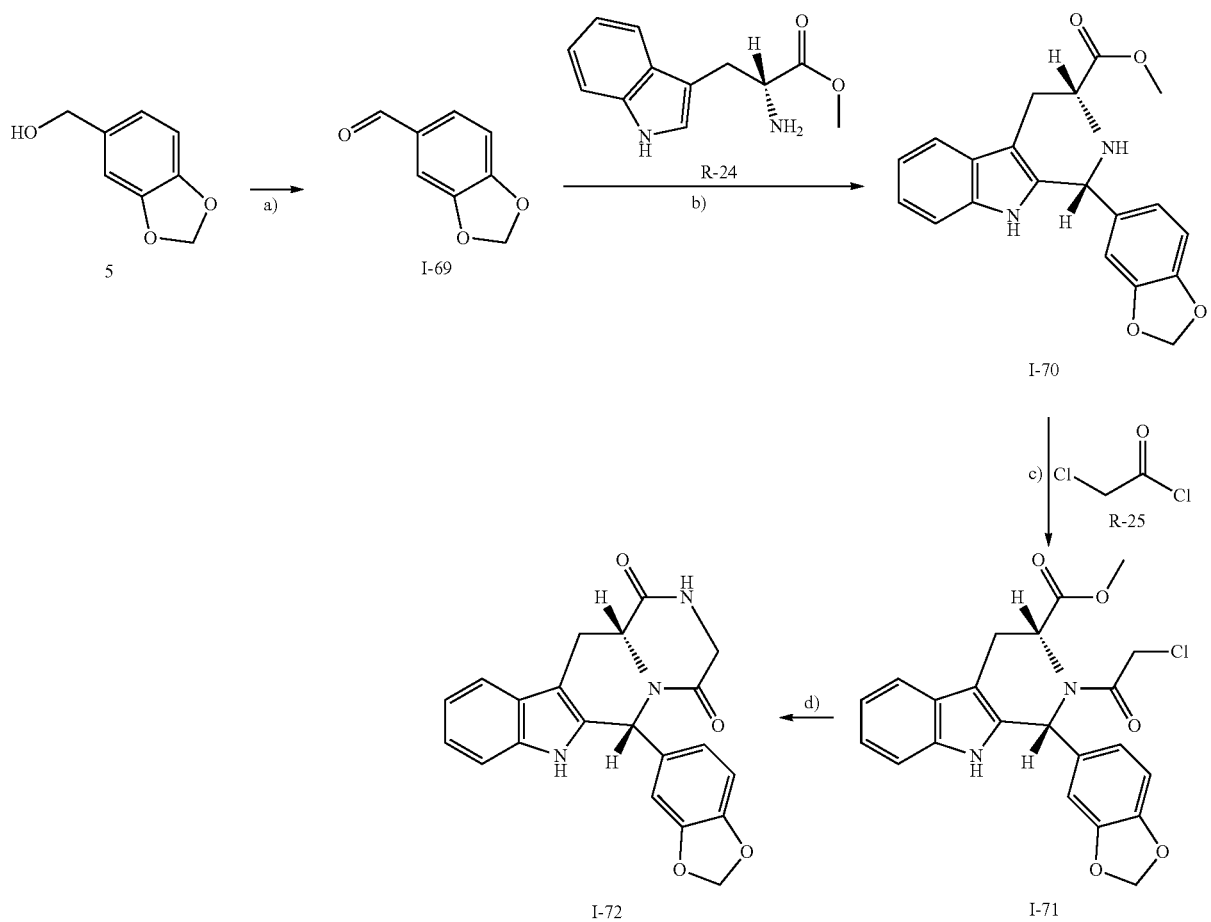

Conditions: a) MnO₂ (10 eq) in DCM, overnight at r.t.; b) R-24 in ⁱPrOH, refluxed overnight; c) Et₃N (2 eq) in THF, R-25 (1 eq) is added at 0° C.; then, 3 hours at r.t.; d) NH₃/methanol (30%) at 40° C. for 3 days.

Any racemic mixture and pure enantiomer is considered.

Preparation of Intermediate I-69a: Benzo[d][1,3]dioxole-5-carbaldehyde

A solution of the commercially available piperonol (5, 100 g, 0.66 mmol) and active MnO₂ (572 g, 6.6 mmol) in DCM (1000 ml) was stirred at r.t overnight. The reaction mixture was filtrated and the filtrate were washed with brine, dried over anhydrous Na₂SO₄ and concentrated to give crude I-69a (80 g, 80% yield) as white solid. ESI-MS (M+1): 151 calc. for $C_8H_6O_3$: 150.1

Preparation of Intermediate I-70a: Methyl 1-(benzo[d][1,3]dioxol-5-yl)-2,3,4,9-tetrahydro-1H-pyrido[3,4-b]indole-3-carboxylate The solution of I-69a (30 g, 0.2 mol) and the reagent (R)-methyl 2-amino-3-(1H-indol-3 yl)propanoate (R-24, 43.6 g, 0.2 mol) in propan-2-ol (500 mL) was refluxed overnight. The reaction mixture was concentrated and the solid was dissolved in aq. NaHCO₃ and DCM. The organic phase was separated and dried over Na₂SO₄, concentrated and the residue was dissolve in 50 mL DCM and hexane (600 mL) was added with stirring. The solid was filtered off and the filtration was concentrated to give crude compound I-70a as racemic mixture (90% cis isomer) (50 g, 70% yield). ESI-MS (M+1): 351 calc. for $C_{20}H_{18}N_2O_4$: 350.

Preparation of Intermediate I-71a: Methyl 1-(benzo[d][1,3]dioxol-5-yl)-2-(2-chloroacetyl)-2,3,4,9-tetrahydro-1H-pyrido[3,4-b]indole-3-carboxylate To a solution of I-70a (50 g, 0.14 mol) and Et₃N (29 g, 0.28 mol) in anhydrous THF (500 mL) was added chloroacetyl chloride (R-25, 17.7 mg, 0.15 mol) at 0° C. The reaction mixture was stirred at r.t. for 3 h. Diluted with 300 mL of DCM and washed by aqueous NaHCO₃, dried and concentrated to give I-71a, racemic mixture (mainly as cis isomer), (20 g, 2.57 mmol, 27% yield) as a yellow solid. ESI-MS (M+1): 427 calc. for $C_{22}H_{19}ClN_2O_5$: 426.1

Preparation of Intermediate I-72a: 6-(1,3-Benzodioxol-5-yl)-2,3,6,7,12,12a-hexahydropyrazino[1',2':1,6]pyrido[3,4-b]indole-1,4-dione The solution of compound I-71a (5 g, 9.5 mmol) in NH₃/methanol (30 mL, 30%) was stirred at 40° C. for 3 days. Concentrated and dissolved in 50 mL of DCM. Washed with water (50 mL×3) and dried. The organic phase was concentrated to give product I-72a, racemic mixture (mainly as cis isomer), (3 g, 84.2% yield) as white solid. ESI-MS (M+1): 376 calc. for $C_{21}H_{17}N_3O_4$: 375.1

Synthetic Route 4b
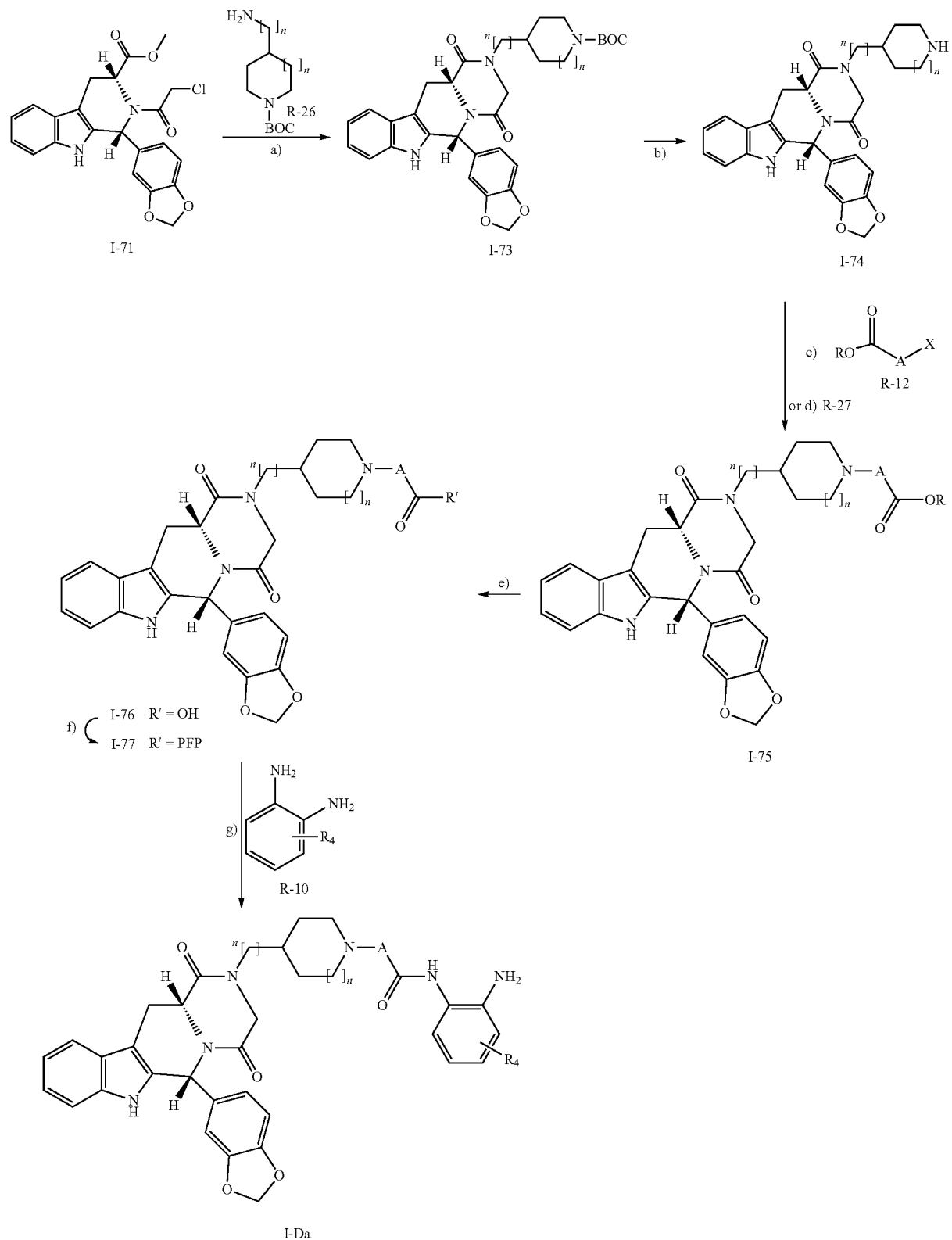
Conditions: a) R-26 (2 eq) in methanol at 80-100° C. overnight; b) HCl/EtOAc (1N) at r.t. for 3 hours; c) $K_2CO_3$ (2.4 eq), R-12 (1.2 eq) in DMF, at 80° C. overnight; d) R-27 (1.2 eq), $CH_3COOH$, $NaBH_3CN$ (2 eq) in DCM at r.t. overnight; e) $LiOH \cdot H_2O$ (2.5 eq) in THF/MeOH/$H_2O$, overnight at r.t.; f) PFP (1 eq), DIC (1.6 eq) in $CH_2Cl_2$, overnight at r.t.; g) R-10 (1.5 eq), (DMAP) and DIEA in DMF at 60° C. overnight.

In the scheme above R is $(C_1-C_6)$alkyl, X is a leaving group, such halogen, and A is a hydrocarbon chain, which optionally contains nitrogen, sulphur and/or oxygen atoms, and optionally contains one or more aromatic, heteroaromatic, carbocyclic and/or heterocyclic rings.

Preparation of Intermediate I-73a: tert-butyl 4-((6-(benzo[d][1,3]dioxol-5-yl)-1,4-dioxo-3,4,6,7,12,12a-hexahydropyrazino[1',2':1,6]pyrido[3,4-b]indol-2(1H)-yl)methyl)piperidine-1-carboxylate To a mixture of intermediate I-61a (4.3 g, 10.07 mmol) in MeOH (200.00 mL) was added tert-butyl 4-(aminomethyl)piperidine-1-carboxylate (R-26a, 4.32 g, 20.15 mmol) in one portion at 25° C. under $N_2$. The mixture was heated to 80~100° C. and stirred for overnight. TLC (DCM:MeOH=20:1) showed the reaction was completed. The mixture was cooled to 25° C., filtered and the filtrate was concentrated to dryness. The residue was purified by silica gel column chromatography (DCM:MeOH=20:1) to afford pure intermediate I-73a, racemic mixture (mainly as cis isomer) (4.0 g, 6.99 mmol, 60.99% yield) as a yellow solid. ESI-MS (M+1): 573 calc. for $C_{32}H_{36}N_4O_6$: 572.2.

Preparation of Intermediate I-74a: 6-(benzo[d][1,3]dioxol-5-yl)-2-(piperidin-4-ylmethyl)-2,3,6,7,12,12a-hexahydropyrazino[1,2':1,6]pyrido[3,4-b]indole-1,4-dione To intermediate I-73a (4.00 g, 5.24 mmol) was added HCl/EtOAc (200.00 mL, 1 N) at 0° C. under $N_2$. The mixture was stirred at 25° C. for 3 hrs. LC-MS showed the reaction was completed. The mixture was concentrated to dryness to afford crude product intermediate I-74a, racemic mixture (mainly as cis isomer) (3.1 g, 4.91 mmol, 93.73% yield) as white solid which was used in the next step without further purification. ESI-MS (M+1): 473 calc. for $C_{27}H_{28}N_4O_4$: 472.2.

Preparation of Intermediate I-75a: ethyl 2-(4-((6-(benzo[d][1,3]dioxol-5-yl)-1,4-dioxo-3,4,6,7,12,12a-hexahydropyrazino[1',2':1,6]pyrido[3,4-b]indol-2(1H)-yl)methyl)piperidin-1-yl)pyrimidine-5-carboxylate To a mixture of intermediate I-74a (900.00 mg, 1.91 mmol) and ethyl 2-chloropyrimidine-5-carboxylate (R-12c, 409.77 mg, 2.20 mmol) in DMF (50.00 mL) was added $K_2CO_3$ (631.31 mg, 4.57 mmol). The mixture was stirred at 80° C. for overnight. TLC (PE:EtOAc=1:1) showed the reaction was completed. The mixture was cooled to 25° C., diluted with water (20 mL) and extracted with EtOAc (3×50 mL). The combined organic phase was washed with saturated brine (2×50 mL), dried with anhydrous $Na_2SO_4$, filtered, concentrated and purified by silica gel column chromatography (PE:EtOAc=1:1) to afford intermediate I-75a, racemic mixture (mainly as cis isomer) (680.00 mg, 1.09 mmol, 59.68% yield) as a white solid. ESI-MS (M+1): 623 calc. for $C_{34}H_{34}N_6O_6$: 622.2.

Preparation of Intermediate I-76a: 2-(4-((6-(benzo[d][1,3]dioxol-5-yl)-1,4-dioxo-3,4,6,7,12,12a-hexahydropyrazino[1',2':1,6]pyrido[3,4-b]indol-2(1H)-yl)methyl)piperidin-1-yl)pyrimidine-5-carboxylic acid To a mixture of intermediate I-75a (680.00 mg, 1.09 mmol) in THF/MeOH/$H_2O$ (10:3:2, 150 mL) was added LiOH·$H_2O$ (114.34 mg, 2.73 mmol) at 25° C. under $N_2$. The mixture was stirred at 25° C. for overnight. LC-MS showed the reaction was completed. Then the mixture was diluted with water and adjusted pH to 4-5 with 2 N HCl. The resulting mixture was concentrated to give the crude intermediate I-76a, racemic mixture (mainly as cis isomer) (450.00 mg, 756.79 umol, 69.43% yield) as a white solid which was used in the next step without further purification. ESI-MS (M+1): 595 calc. for $C_{32}H_{30}N_6O_6$: 594.2.

Preparation of I-77a: 2,3,5,6-tetrafluoro-4-methylphenyl 2-(4-((6-(benzo[d][1,3]dioxol-5-yl)-1,4-dioxo-3,4,6,7,12,12a-hexahydropyrazino[1,2':1,6]pyrido[3,4-b]indol-2(1H)-yl)methyl)piperidin-1-yl)pyrimidine-5-carboxylate To a mixture of intermediate I-76a (450.00 mg, 756.79 umol) and DIC (617.08 mg, 4.89 mmol) in DCM (50.00 mL) was added 2,3,4,5,6-pentafluorophenol (167.15 mg, 708.15 umol,) at 0° C. under $N_2$. The mixture was stirred at 25° C. for overnight. LC-MS showed the reaction was completed. Then the mixture was concentrated and purified by prep-HPLC (General procedure, Method 6) to give pure intermediate I-77a, racemic mixture (mainly as cis isomer) (300.00 mg, 394.39 umol, 52.11% yield) as a white solid. ESI-MS (M+1): 761 calc. for $C_{38}H_{29}N_6O_6F_5$: 760.2.

Preparation of Compound 4-01: N-(2-aminophenyl)-2-(4-((6-(benzo[d][1,3]dioxol-5-yl)-1,4-dioxo-3,4,6,7,12,12a-hexahydropyrazino[1',2':1,6]pyrido[3,4-b]indol-2(1H)-yl)methyl)piperidin-1-yl)pyrimidine-5-carboxamide To a solution of intermediate I-77a (100 mg, 131.46 umol) in DMF (20.00 mL) were added benzene-1,2-diamine (R-10a, 21.32 mg, 197.19 umol), DIEA (3.40 mg, 26.29 umol) and DMAP (1.61 mg, 13.15 umol) at 25° C. under $N_2$. The mixture was stirred at 60° C. for overnight. LC-MS showed the reaction was completed. The mixture was cooled to 25° C. then poured into water (10 mL). The aqueous phase was extracted with ethyl acetate (3×20 mL). The combined organic phase was washed with saturated brine (2×20 mL), dried with anhydrous $Na_2SO_4$, filtered, concentrated and purified by prep-HPLC (General procedure, Method 7) to give pure compound 4-01, racemic mixture (mainly as cis isomer) (12.00 mg, 15.77 umol, 12.00% yield, 90% purity) as a white solid. ESI-MS (M+1): 685.4 calc. for $C_{38}H_{36}N_8O_5$. Rt=3.027 min.

Preparation of Intermediate I-75b: methyl 4-((4-((6-(benzo[d][1,3]dioxol-5-yl)-1,4-dioxo-3,4,6,7,12,12a-hexahydropyrazino[1',2':1,6]pyrido[3,4-b]indol-2(1H)-yl)methyl)piperidin-1-yl)methyl)benzoate To a solution of intermediate I-74a (750.00 mg, 1.59 mmol) in DCM (100 mL) were added methyl 4-formylbenzoate (R-27a) (313.22 mg, 1.91 mmol) and $CH_3COOH$ (1.00 mL) at 25° C. After stirring for 1 h, $NaBH_3CN$ (199.83 mg, 3.18 mmol) was added at 25° C. The reaction mixture was stirred at 25° C. for overnight. TLC (PE:EtOAc=1:3) showed the reaction was completed. The mixture was poured into water (50 mL) and extracted with DCM (2×100 mL). The combined organic phase was washed with saturated brine (2×100 mL), dried with anhydrous $Na_2SO_4$, filtered and purified by prep-TLC (PE:EtOAc=1:3) to give intermediate I-75b, racemic mixture (mainly as cis isomer) (360.00 mg, 580 umol, 36.48% yield) as a white solid. ESI-MS (M+1): 621 calc. for $C_{36}H_{36}N_4O_6$: 620.2.

Preparation of Intermediate I-76b: 4-((4-((6-(benzo[d][1,3]dioxol-5-yl)-1,4-dioxo-3,4,6,7,12,12a-hexahydropyrazino[1',2':1,6]pyrido[3,4-b]indol-2(1H)-yl)methyl)piperidin-1-yl)methyl)benzoic acid To a mixture of intermediate I-75b (360 mg, 563.89 umol) in THF/MeOH/H$_2$O (2:1:1, 60 mL) was added LiOH.H$_2$O (59.15 mg, 1.41 mmol) at 25° C. The mixture was stirred at 25° C. for overnight. TLC (PE:EtOAc=1:1) showed the reaction was completed. The mixture was poured into water (50 mL) and extracted with EtOAc (3×50 mL). The combined organic phase was washed with saturated brine (2×50 mL), dried with anhydrous Na$_2$SO$_4$, filtered and concentrated to dryness under vacuum to afford intermediate I-76b, racemic mixture (mainly as cis isomer) (150 mg, 247.25 umol, 43.85% yield) as a white solid. ESI-MS (M+1): 607 calc. for $C_{35}H_{34}N_4O_6$: 606.2.

Preparation of Intermediate I-77b: perfluorophenyl 4-((4-((6-(benzo[d][1,3]dioxol-5-yl)-1,4-dioxo-3,4,6,7,12,12a-hexahydropyrazino[1',2':1,6]pyrido[3,4-b]indol-2(1H)-yl)methyl)piperidin-1-yl)methyl)benzoate To a mixture of intermediate I-76b (150 mg, 247.25 umol) and DIC (46.80 mg, 370.88 umol) in DCM (20.00 mL) was added 2,3,4,5,6-pentafluorophenol (54.61 mg, 296.70 umol) at 0° C. under N$_2$. The mixture was stirred at 25° C. for overnight. LC-MS showed the reaction was completed. The mixture was concentrated and purified by prep-HPLC (General procedure, Method 6) to afford intermediate I-77b, racemic mixture (mainly as cis isomer) (30 mg, 38.87 umol, 15.72% yield) as a white solid. ESI-MS (M+1): 773 calc. for $C_{41}H_{33}F_5N_4O_6$: 772.2.

Preparation of Compound 4-02: N-(2-aminophenyl)-4-((4-((6-(benzo[d][1,3]dioxol-5-yl)-1,4-dioxo-3,4,6,7,12,12a-hexahydropyrazino[1',2':1,6]pyrido[3,4-b]indol-2(1H)-yl)methyl)piperidin-1-yl)methyl)benzamide To a solution of intermediate I-77b (30 mg, 38.87 umol) in DMF (5.00 mL) were added benzene-1,2-diamine (R-10a, 6.30 mg, 58.24 umol), DMAP (474.32 ug, 3.88 umol) and DIEA (10.04 mg, 77.65 umol) at 25° C. for 10 min, then the mixture was stirred at 60° C. for overnight. LC-MS showed the reaction was completed. The mixture was concentrated in vacuum to give the crude product which was purified by prep-HPLC (General procedure, Method 8) to give pure compound 4-02, racemic mixture (mainly as cis isomer) (4.6 mg, 17.00% yield) as a white solid. ESI-MS (M+1): 697.5 calc. for $C_{41}H_{40}N_6O_5$: 696.2. Rt=2.97.

Biological Tests
In vitro Activity
PDE Enzyme Activity Assay

The biochemical assay to measure PDE5A, PDE9A isoform b, PDE4D7, and PDE4A1 enzyme activities relies on the HTRF cGMP assay kit from CisBio (CisBio, Cat. #62GM2PEB), that determines the amount of cGMP present in the reaction. The enzymes were obtained from BPS Biosciences (GenBank Accession number for PDE5A: NM_001083, Cat. #60050; PDE9A: NM_001001567, Cat. #60090; PDE4D7: NM_001165899, Cat. #60047; and PDE4A1: U97584, Cat. #60040) and they are full-length with N-terminal GST tag. They were expressed in a baculovirus infected Sf9 cell expression system.

For each enzyme, enzyme activity assay was carried out in a 384-well plate in a final volume of 20 μL, as follows:

2.5 μL of vehicle or studied compound 4× concentrated prepared in assay buffer containing 50 mM Tris-HCl, 6 mM MgCl$_2$, pH 7.4 (PDE5A, PDE4D7, PDE4A1) and additionally 0.03% Tween-20 (PDE9A). Final percentage of DMSO was 0.5%.

2.5 μL of PDE5A (7 μg/mL) or 2.5 μL PDE9A (0.2 μg/mL) or 2.5 μL PDE4D7 (1.25 μg/mL) or 2.5 μL PDE4A1 (1.5 μg/mL) diluted in assay buffer. Final concentration was 1.75 μg/mL (PDE5A) or 0.05 μg/mL (PDE9A) or 0.31 μg/mL (PDE4D7) or 0.375 μg/mL (PDE4A1).

5 μL of substrate cGMP 4× concentrated to reach a final concentration of cyclic nucleotide of 100 nM (PDE5A and PDE9A) or 250 nM (PDE4D7 and PDE4A1).

After plate sealing, mixture was incubated for 30 minutes at 37° C.

Reaction was stopped by adding 5 μL of labelled cGMP labelled with the dye D2 (cGMP-D2) and 5 μL of Mab anti-cGMP labelled with cryptate (cGMP-cryptate) as recommended by the assay kit of CisBio.

Plate was sealed and incubated 1 hour at room temperature.

Fluorescence of each well was determined at 665 nm excitation and 620 nm emission using the plate reader EnVision (Perkin-Elmer). Results, Table 1 (below), were calculated from the 665 nm/620 nm ratio. Positive control was obtained in the presence of the vehicle of the compounds. Negative control was obtained in the absence of cGMP and labelled cGMP-D2 cyclic nucleotide.

HDAC Activity Using SHSY-5Y Cell Line

HDAC inhibition leads to the corresponding functional response, increase in AcH3 level. Therefore, the cellular assay to conclude HDAC activity was assessed by Western blot analysis using specific antibodies against acetylated histone 3 at Lys9 (AcH3K9). Cell cultures were treated at 100 nM, 500 nM, 1 μM and/or 5 μM with compounds of the invention or known PDE inhibitors during 24 hours and, Table 1 (below) describes the functional activity: histone 3 acetylation level (AcH3) vs basal (no treatment).

A human neuroblastoma cell line (SHSY-5Y) was used. Cell line was obtained from ATCC (CRL-2266) and cultured in 35 mm plates (Becton Dickinson, NJ).

The cells were grown to 90% confluence at 37° C. in an atmosphere of 5% CO2 and in Dulbecco's modified Eagle's medium supplemented with Glutamax (Gibco, Invitrogen, CA), 100 units/ml penicillin/streptomycin, 1×MEM nonessential amino acids and 10% fetal bovine serum (Gibco, Invitrogen, CA).

Cells were collected and sonicated in a buffer containing a cold lysis buffer with protease inhibitors (0.2 M NaCl, 0.1 M HEPES (4-(2-hydroxyethyl)-1-piperazineethanesulfonic acid), 10% glycerol, 200 mM NaF, 2 mM Na$_4$P$_2$O$_7$, 5 mM EDTA (ethylenediaminetetraacetic acid), 1 mM EGTA (ethylene glycol tetraacetic acid), 2 mM DTT (dithiothreitol), 0.5 mM PMSF (phenylmethylsulfonyl fluoride), 1 mM Na$_3$VO$_4$ and Complete Protease Inhibitor Cocktail, Roche Diagnostics), centrifuged at 14,000×g 4° C. for 20 min and the supernatant was aliquoted and stored at −80° C. Total protein concentrations were determined using the BioRad Bradford protein assay (BioRad Laboratories).

Protein samples were mixed with Laemmli sample buffer, resolved onto Sodium Dodecyl Sulfate (SDS)-polyacrylamide gels and transferred to nitrocellulose membrane. The membranes were blocked with 5% milk, 0.05% Tween-20 in PBS (Phosphate-Buffered Saline) or TBS (Tris-Buffered Saline) followed by overnight incubation with the following primary antibodies: rabbit polyclonal anti-acetylated Histone 3 (acetyl K9) (Cell Signalling Technology), rabbit polyclonal anti-total Histone 3 (Millipore), in the corresponding buffer. All the antibodies were used at 1:1000 dilution except the mouse monoclonal anti-β-actin which was used at 1:50.000. Following two washes in TBS/Tween20 and one wash in TBS alone, immunolabeled protein bands were detected by using HRP-conjugated anti-rabbit or anti-mouse antibody (Santa Cruz Biotechnology; dilution 1:5.000) following an enhanced chemiluminescence system (ECL, GE Healthcare Bioscience, Buckinghamshire, UK), and autoradiographic exposure to HyperfilmtECL (GE Healthcare Bioscience). Quantity One™ software v.4.6.3 (Bio-Rad) was used for quantification.

Table 1 shows the inhibition values for recombinant enzymes ($IC_{50}$) PDE5A1 and PDE9A; where, $IC_{50} \geq 10$ μM (+) (inactive), 1 μM $\leq IC_{50} < 10$ μM (++), 10 nM $\leq IC_{50} < 1$ μM (+++) and $IC_{50} < 10$ nM (++++). In addition, Table 1 also shows increment in Histone 3 acetylation level (AcH3) vs basal (no treatment); thus, basal x1 means no increment (+), basal x1.4 $\leq$(++)<basal x2, basal x2$\leq$(+++)<basal x3 and basal x3$\leq$(++++). N.E. means No Effect. Known PDE inhibitors (Sildenafil and Tadalafil) as well as a HDAC inhibitor (Vorinostat) were also included as references.

TABLE 1

| Example | PDE5A1 | PDE9A | AcH3[a] | AcH3[b] | AcH3[c] | AcH3[d] |
|---|---|---|---|---|---|---|
| Tadalafil | ++++ | + | N.E. | | | |
| Sildenafil | ++++ | ++ | N.E. | | | |
| Vorinostat | + | + | ++++ | | | |
| 1-01 | +++ | | +++ | | | |
| 1-02 | +++ | | +++ | | | |
| 1-03 | +++ | | ++++ | | | |
| 1-04 | +++ | | ++++ | | | |
| 1-05 | +++ | | +++ | | | |
| 1-06 | +++ | | +++ | | | |
| 1-08 | +++ | | ++++ | | | |
| 1-11 | +++ | | +++ | ++ | ++ | |
| 1-13 | ++ | | ++ | | | |
| 1-15 | +++ | | ++ | | | |
| 1-19 | +++ | | ++ | | | |
| 1-20 | ++ | | ++ | | | |
| 2-02 | ++++ | | ++++ | | | |
| 2-03 | ++++ | | ++ | | | |
| 2-04 | ++++ | | ++++ | | | |
| 2-07 | +++ | | ++ | | | |
| 3-01 | | +++ | ++ | | | |
| 4-01 | ++ | | | | | ++ |

[a] Compound concentration was 1 μM
[b] Compound concentration was 500 nM
[c] Compound concentration was 100 nM
[d] Compound concentration was 5 μM As can be seen in the above table, tested compounds of the invention show a dual activity, inhibition of PDEs and histone 3 acetylation, that may play a critical role for AD treatment and is not achieved by reference compounds (e.g. Sildenafil, Tadalafil or Vorinostat).

AD-related Markers (APP Processing and pTau) in Tg2576 Neurons.

The effects of the compounds on amyloid pathology were analysed in primary cultures after 21 days in-vitro (DIV) of neurons derived from the hippocampus and cortex of Tg2576 mouse embryos. Tg2576 mice express the human 695-aa isoform of APP (hAPP) containing the Swedish double mutation, which favours Aβ production. Neurons were treated for two days and collected at day 3, 24 h after the last treatment. First it was analysed the effect of the compounds on hAPP processing by the amyloidogenic pathway by measuring the carboxyl terminal fragment AβPP (C99), which is the precursor of Aβ42. In this case the reported $EC_{50}$, Table 2 (below), means a 50% decrease in C99 levels over basal (vehicle, no treatment).

It was next analyzed the effect of the compounds on levels of phosphorylated tau (p-Tau) in the same samples, another marker of AD, using a phospho-specific antibody (AT8) that recognizes hyperphosphorylated epitopes on Ser202/Thr205. In this case the reported $EC_{50}$, Table 2 (below), means a 50% decrease in pTau levels over basal (vehicle, no treatment).

To analyze APP-derived fragments and p-Tau levels in primary neuronal cultures, cells were collected in a buffer containing SDS (2%), Tris-HCl (10 mM, pH 7.4), protease inhibitors (1 mM phenylmethylsulfonyl fluoride (PMSF) and Complete Protease Inhibitor Cocktail: Roche Diagnostics) and phosphatase inhibitors (0.1 mM $Na_3VO_4$ and 1 mM NaF). The homogenates were sonicated for 2 min and centrifuged at 100,000×g for 1 h. Aliquots of the supernatant were frozen at 80° C. and their protein concentrations determined by the Bradford method using the Bio-Rad protein assay (Bio-Rad, Hercules, Calif., USA).

Aliquots of the protein extracts were mixed with XT sample buffer plus XT reducing agent (Bio-Rad, Hercules, Calif., USA) and boiled for 5 min. Proteins were separated in a Criterion precast Bis-Tris 4-12% gradient precast gel (Bio-Rad, Hercules, Calif., USA) and transferred to a Polyvinylidene fluoride (PVDF) membrane with a removal rating of 0.2 mm (Hybond LFP, Amersham Biosciences, Little Chalfont, UK). The membranes were blocked with 5% milk, 0.05% Tween-20 in PBS or TBS, and incubated overnight with the following primary antibodies in the corresponding buffers: mouse monoclonal anti-phosphotau AT8 (Pierce Biotechnology Inc., Rockford), 6E10 mouse monoclonal antibody (amino acids 1-17 of Aβ peptide; Millipore), mouse monoclonal anti-β-actin. All antibodies were used at dilutions of 1:1,000 except for the mouse monoclonal anti-β-actin (1:50,000). Following two washes in TBS/Tween20 and one wash in TBS alone, immunolabelled protein bands were detected using HRP-conjugated anti-rabbit or anti-mouse antibodies (diluted 1:5,000 Santa Cruz Biotechnology). Binding was visualised by enhanced chemiluminescence (ECL, GE Healthcare Bioscience, Buckinghamshire, UK) and autoradiographic exposure to Hyperfilm ECL (GE Healthcare Bioscience), using Quantity One™ software v.4.6.3 (Bio-Rad) for quantification.

Table 2 shows the functional response on primary cultures, Tg2576 neurons. Known PDE5 inhibitor (Tadalafil) as well as HDAC inhibitor (Vorinostat) were included as references and their functional responses are reported as $EC_{50}$; where, N.E. means No Effect, $EC_{50} \geq 10$ μM (+), 1 μM $\leq EC_{50} < 10$ μM (++), 10 nM $\leq EC_{50} < 1$ μM (+++) and $EC_{50} < 10$ nM (++++). Compounds of the invention are assayed at fixed concentration, (50 nM) and decrease in C99 and pTau levels over basal (saline, no treatment) are also reported; where, basal x1 means no reduction (+), basal x0.2 $\leq$(++)<basal x0.4 (reduction between 20% and 40%), basal x0.4 $\leq$(+++)<basal x0.6 (reduction between 40% and 60%) and basal x0.6 $\leq$(++++) (reduction equal or bigger than 60%). N.E. means No Effect.

TABLE 2

| Example | pTau | C99 |
|---|---|---|
| Tadalafil | +++ | |
| Vorinostat | +++ | |
| 1-11[a] | ++ | ++ |

[a]Compound concentration was (50 nM)

In-vivo Activity
Inhibition of pCREB and AcH3 in Wild Type Mice

To determine the ability of the compounds of the invention to inhibit HDAC and PDE in the brain, compounds were administered to wild type mice by i.p. at a single dose of 40 mg/kg (n=3). Another group of animals received the vehicle (1/1/8, v:v:v, DMSO/Tween 20/saline). One hour later, mice were sacrificed by cervical dislocation and their hippocampus was quickly dissected from the brains. Total tissue homogenates were obtained by homogenizing the hippocampus in a cold lysis buffer with protease inhibitors (0.2 M NaCl, 0.1 M HEPES, 10% glycerol, 200 mM NaF, 2 mM $Na_4P_2O_7$, 5 mM EDTA, 1 mM EGTA, 2 mM DTT, 0.5 mM PMSF, 1 mM $Na_3VO_4$ and Complete Protease Inhibitor Cocktail, Roche Diagnostics). The homogenate was then centrifuged at 14,000×g at 4° C. for 20 min and the supernatant aliquoted and stored at −80° C. Total protein concentrations were determined using the BioRad Bradford protein assay (BioRad Laboratories). Protein samples were analyzed as described in the "in vitro" section. Results are shown in table 3.

AD-related Markers (APP Processing (C99) and pTau) in Tg2576 Mice.

The effects of the compounds were also analysed in Tg2576 mice after chronic treatment (3-5 weeks) using hippocampal homogenates obtained in a buffer containing SDS (2%) and following the same protocol as described in the wild type mice studies and the analysis accomplished according to protocol described in the in vitro Tg2576 neurons.

Table 3 shows increment in biological response vs basal (no treatment); thus, basal x1 means no increment (+), basal x1≤(++)<basal x2, basal x2≤(+++)<basal x3, basal x3≤(++++)<basal x4 and basal x4≤(+++++). N.E. means No Effect. Known PDE5 inhibitor (Tadalafil) as well as a HDAC inhibitor (Vorinostat) were also included as references. [a]data obtained from wild type mice, [b]data obtained from Tg2576 mice.

TABLE 3

| Example | pCREB[a] | AcH3[a] | pTau[b] | C99[b] |
|---|---|---|---|---|
| Tadalafil[c] | +++ | N.E. | +++ | |
| Vorinostat[d] | N.E. | +++ | | |
| 1-11 | +++ | ++ | | |

[c]single dose of 1 mg/Kg; i.p.
[d]single dose of 12.5 mg/Kg; i.p.

As can be seen in the above table, tested compounds of the invention show a functional dual activity in-vivo that may play a critical role for AD treatment and is not achieved by reference compounds (Tadalafil and Vorinostat).

Pharmacokinetics

Plasma and brain samples for measuring compounds concentrations were collected at predetermined times from four wild type mice per point. Three time points were measured: 0.25, 0.5 and 1.0 hour. Compounds concentration was measured using a Xevo-TQ MS triple quadrupole mass spectrometer with an electrospray ionization (ESI) source and an Acquity UPLC (Waters, Manchester, UK).

Dose Preparation and Dose Administration:

Compounds solutions were prepared by dissolving the samples in DMSO and this solution was made up to a final volume by addition of a mixture of Tween 20 and 0.9% NaCl (1/1/8, v:v:v, DMSO/Tween 20/saline). Compounds were injected as a single intraperitoneal injection. Animals were killed by decapitation.

Sample Collection:

Plasma. Blood was collected into tubes containing EDTA and plasma was collected via centrifugation (4° C., 13200 rpm, 5 min) and stored at −80° C. until analysis.

Brain. Brains were collected immediately after mice death. The brains were excised, weighed and frozen at −80° C. until further process for analysis.

Chromatography:

Chromatographic separation was performed by gradient elution at 0.4 mL/min using an Acquity UPLC BEH C18 column (100×2.1 mm, 1.7 μm particle size; Waters). The mobile phase consisted of A: water with 0.1% formic acid, B: methanol with 0.1% formic acid. After 1.5 min at the initial condition of 95% A, solvent B was increased from 5% to 100% over 2 min, maintained at 100% for 1.5 min, then a linear gradient to initial conditions was applied for 0.1 min and maintained for 3.4 minutes to re-equilibrate the column, giving a cycle time of 8.5 min. The autosampler temperature was set at 10° C. and column temperature at 45° C.

Mass Spectrometry:

Compounds were monitored using a triple quadrupole mass spectrometer equipped with an electrospray ionization interface. For detection and quantification, a capillary voltage of 3.5 kV and a cone voltage of 38 V were used. Source and desolvation temperatures were 150° C. and 650° C., respectively. Ultra-high purity nitrogen was used for cone gas (75 L $h^{-1}$) and desolvation gas (1000 L $h^{-1}$). The electrospray ionization operated in the positive mode, and the collision gas used was ultra-pure argon at a flow rate of 0.15 mL $min^{-1}$.

Quantification and Sample Preparation:

Quantification was achieved by external calibration using matrix-matched standards. Concentrations were calculated using a weighted least-squares linear regression (W=1/x). Calibration standards were prepared by adding the appropriate volume of diluted solutions of the compound (made in a mixture of methanol and water, 50:50, v:v) to aliquots of 50 uL of blank plasma or to 75 mg of homogenized blank brain. 2% formic acid in acetonitrile was added to precipitate the proteins. The mixture was then agitated for 10 min and centrifuged at 13200 rpm for 5 min at 4° C. The resulting supernatants were transferred to a Ostro plate (Waters, Manchester, UK), designed to remove phospholipids. The resulting eluents were evaporated at 37° C. under a stream of nitrogen. Residues were dissolved in 75 μL of a mixture of methanol and water (50:50, v:v). A 10-uL aliquot of the resulting solution was injected onto the LC-MS/MS system for analysis. Frozen plasma samples were thawed at room temperature, vortexed thoroughly and subjected to the above described extraction procedure. Brain samples were thawed unassisted at room temperature and homogenized using a Branson 250 ultrasonic sonifier (Branson, Danbury, Conn., USA). When homogenized, 75 mg were weighted and extracted as described previously.

Results

Concentration values obtained from the LC-MS/MS analyses are described in Table 4. Table 4 shows plasma and brain concentration 1 hour after administration as well as brain/plasma ratio for the compounds; dosage was 40 mg/Kg (i.p.).

TABLE 4

| Compound | C (plasma; nM) | C (brain; nmol/Kg) | Brain/Plasma ratio (%) | Crosses BBB? |
|---|---|---|---|---|
| 1-11 | 12132.5 (1762.9)[a] | 1903.4 (565.8)[a] | 15.7 | Yes |

[a]Standard Deviation value

As can be seen in the above table, tested compounds of the invention crosses the blood-brain barrier and reach the brain with effective concentration—as it is confirmed above in Table 3 (functional response).

Memory Function in Aged-Tg2576 Mice

The effect on memory function of compounds of the invention was studied in Tg2576 mice (16-18 month) after a chronic treatment of 3-5 weeks by using two different behavioral tasks: the Fear Conditioning (FC) and the Morris water maze (MWM) test, Table 5 (below)

The behavioural procedure of FC task involved three phases: habituation, training and testing. During habituation phase, mice were habituated to the conditioning box (context) for 5 min with no stimuli presented. 24 hours later (training phase), mice were placed in the training chamber and allowed to explore for 2 min, afterward, a footshock (0.3 mA) unconditioned stimulus was administered (2 s) and 30 s after mice were returned to their home cage. Mice were returned to the conditioning chamber 24 h after training and allowed to explore the context for 2 min, during which freezing behavior was recorded (contextual long term memory). Freezing scores were expressed as percentages. The conditioning procedure was carried out in a StartFear system (Panlab S.L., Barcelona, Spain) that allows recording and analysis of the signal generated by the animal movement through a high sensitivity Weight Transducer system. The analogical signal is transmitted to the FREEZING and STARTLE software modulated through the load cell unit for recording purposes and posterior analysis in terms of activity/immobility.

The MWM test was used to evaluate spatial memory. After treatments, groups of animals underwent spatial reference learning and memory testing in the MWM. The water maze was a circular pool (diameter 1.2 m) filled with water maintained at 20° C. and made opaque by the addition of non-toxic white paint. Mice were trained for three consecutive days (8 trials/day) swimming to a raised platform (visible-platform). No distal visible cues were present during this phase. The same platform location was used for all visible platform sessions and was changed for the invisible-platform training (submerged 1 cm beneath the surface) conducted over 8 consecutive days (4 trials/day) with all visible distal cues present in this phase. In both visible- and hidden-platform versions, mice were placed pseudo-randomly in selected locations, facing toward the wall of the pool to eliminate the potentially confounding contribution of extramaze spatial cues. Each trial was terminated when the mouse reached the platform or after 60 seconds, whichever came first. To test the retention, three probe trials were performed at the beginning of 4th, 7th, and the last day of the test (day 9). In the probe trials the platform was removed from the pool, and the percentage of time spent in the quadrant where the platform was previously set was recorded. All trials were monitored by a camera above the center of the pool connected to a SMART-LD program (Panlab S.L., Barcelona, Spain) for subsequent analysis of escape latencies, swimming speed, path length and percent time spent in each quadrant of the pool during probe trials. All experimental procedures were performed blind to groups.

TABLE 5

| Compound | FC (% freezing) | p value[a] (FC) | MWM (% of time on right quadrant)[b] | p value[a] (MWM) |
|---|---|---|---|---|
| Vehicle | 37.96 (2.10)[c] | | 18.91 (2.52)[c] | |
| 1-11[d] | 59.65 (9.2)[c] | 0.05 | 33.83 (2.24)[c] | <0.01 |

[a]t-Student test, compound of the invention vs vehicle
[b]Retention phase of MWM test, day 4th
[c]Standard error value
[d]20 mg/Kg, i.p.

As can be seen in the above table, tested compound of the invention ameliorates memory retention deficits of aged-Tg2576 mice in both behavioral tasks (FC and MWM) where these animals are severely impaired.

The invention claimed is:

1. A compound of formula (I), or a pharmaceutically acceptable salt thereof, or any stereoisomer or mixtures thereof, either of the compound of formula (I) or of any of its pharmaceutically acceptable salts,

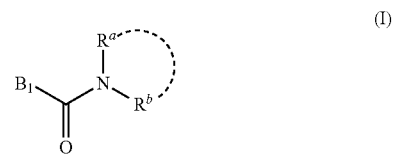

(I)

wherein the moiety —NR$^a$R$^b$, wherein the dashed line means that R$^a$ and R$^b$ optionally form a known ring system, is selected from the group consisting of formula (M$^3$) and formula (M$^4$):

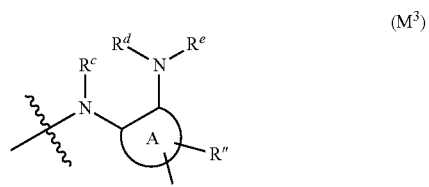

(M$^3$)

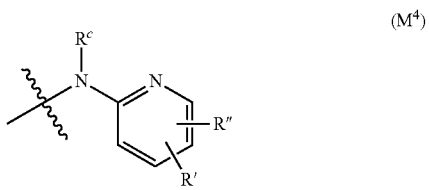

(M$^4$)

B$_1$ is a radical selected from the group consisting of formula (A") and formula (C"):

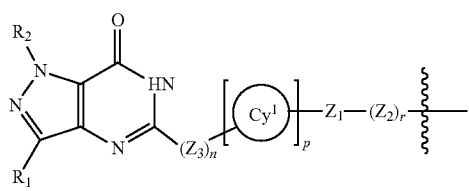
(A″)

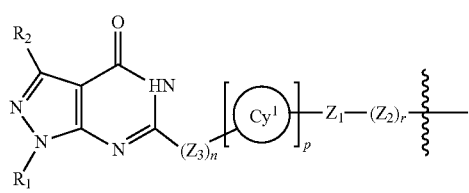
(C″)

with the condition that the moiety (L₁) in the formula (A″), and formula (C″)

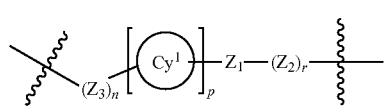
(L₁)

has a chain length comprised from 1 to 20 atoms; and wherein the radical of formula (A″) has the formula:

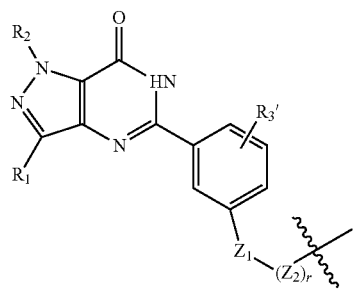

whereby the compound of formula (I) is a compound of formula (IA):

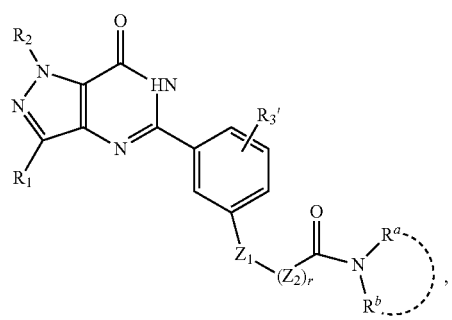
(IA)

and wherein the radical of formula (C″) has the formula:

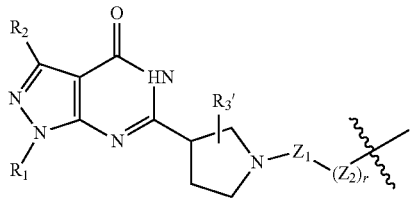

whereby the compound of formula (I) is a compound of formula (IC′″):

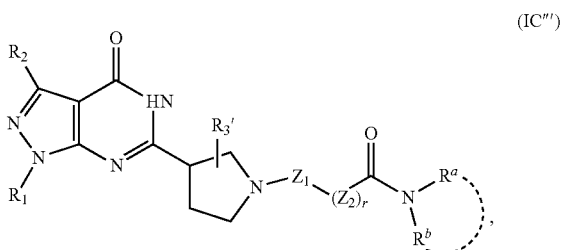
(IC′″)

or alternatively, wherein the radical of formula (C″) has the formula:

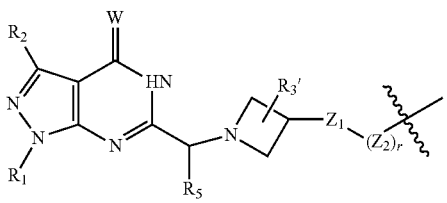

whereby the compound of formula (I) is a compound of formula (IC^IV):

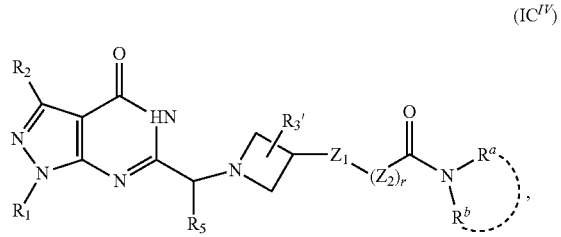
(IC^IV)

wherein
$R^c$ is hydrogen;
$R^d$ and $R^e$ are independently selected from H, —($C_1$-$C_7$) alkyl optionally substituted with one or more halogen atoms, and a known 3- to 8-membered carbocyclic monocyclic ring, saturated or partially unsaturated, which is optionally substituted with one or more halogen atoms,
A is a known ring system selected from phenyl and 5- to 6-membered heteroaromatic ring, wherein the substituents —$NR^c$— and —$NR^dR^e$ are attached to adjacent carbon atoms;
R′ and R″ are independently selected from the group consisting of H, $R^f$, phenyl optionally substituted with one or more substituents R^f, 5- or 6-membered heteroaromatic ring optionally substituted with one or more substituents R^f, and —(C_1-C_7)alkyl optionally substituted with one or more halogen atoms;

each R^f is independently selected from halogen, —NO_2, —CN, —OR^g, —OC(O)R^g, —OC(O)OR^g, —OC(O)NR^gR^g, —NR^gR^g, —NR^gC(O)R^g, —NR^gC(O)OR^g, —NR^gC(O)NR^gR^g, —NR^gS(O)_2R^g, —NR^gSO_2NR^gR^g, —SR^g, —S(O)R^g, —SO_2R^g, —SO_2(OR^g), —SO_2NR^gR^g, —C(O)R^g, —C(O)OR^g, —C(O)NR^gR^g, and —C(O)NR^gOR^g;

each R^g is independently selected from H, —(C_1-C_7)alkyl optionally substituted with one or more halogen atoms, and a known 3- to 7-membered carbocyclic monocyclic ring, saturated or partially unsaturated, which is optionally substituted with one or more halogen atoms;

r is 0 or 1;

$R_1$ and $R_2$ are independently selected from the group consisting of H; saturated or unsaturated (C_1-C_7)alkyl optionally substituted with one or more halogen atoms; and a 3- to 7-membered carbocyclic or heterocyclic monocyclic ring, which is saturated or partially unsaturated or aromatic, and which is optionally substituted with one or more substituents selected from halogen and (C_1-C_3)alkyl;

$Z_1$ is a biradical selected from the group consisting of a formula (E), formula (F″), formula (G′), formula (H′), formula (J′), and formula (K):

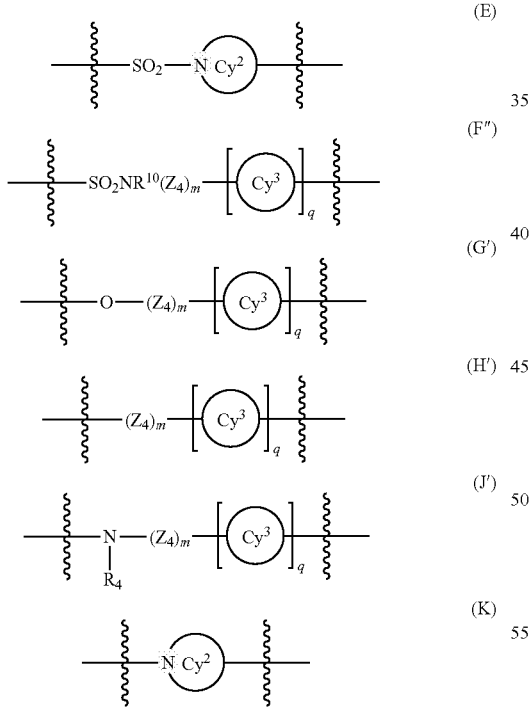

$Z_2$ is selected from the group consisting of —$Z_5$—; —$Z_5$-Cy^4-; —$Z_5$-Cy^4-$Z_5$-; and -Cy^4-;

each $Z_5$ is independently a biradical of a saturated or unsaturated (C_1-C_6)alkyl optionally substituted with one or more halogen atoms;

$Z_4$ is a biradical of a saturated or unsaturated (C_1-C_6)alkyl optionally substituted with one or more substituents selected from halogen, OH, and —O(C_1-C_3)alkyl optionally substituted with one or more halogen atoms; or alternatively $Z_4$ is —CR^{11}R^{12}—, wherein R^{11} and R^{12} taken together with the carbon they are attached to form C═O or a 3- to 7-membered carbocyclic or heterocyclic monocyclic ring, which is saturated or partially unsaturated, and which is optionally substituted with one or more halogen atoms or (C_1-C_3)alkyl optionally substituted with one or more halogen atoms;

q and m are independently 0 or 1;

Cy^2 is a N-attached 3- to 7-membered saturated or partially unsaturated heterocyclic monocyclic ring, which is optionally fused, bridged-fused or spiro-fused to a 3- to 7-membered saturated or partially unsaturated carbocyclic or heterocyclic monocyclic ring, wherein Cy^2 is optionally substituted with one or more $R_3$ groups;

Cy^3 and Cy^4 are independently phenyl or a 3- to 7-membered carbocyclic or heterocyclic monocyclic ring, which is saturated or partially unsaturated or aromatic, and which is optionally substituted with one or more $R_3$ groups;

$R_3'$ is H or $R_3$;

$R_3$ is selected from halogen; saturated or unsaturated (C_1-C_7)alkyl optionally substituted with one or more halogen atoms; saturated or unsaturated —O(C_1-C_7)alkyl optionally substituted with one or more halogen atoms; and a 3- to 7-membered carbocyclic or heterocyclic monocyclic ring, which is saturated or partially unsaturated or aromatic, and which is optionally substituted one or more substituents selected from the group consisting of halogen and (C_1-C_6)alkyl optionally substituted with one or more halogen atoms;

R^4 and R^{10} are independently H or (C_1-C_6)alkyl optionally substituted with one or more halogen atoms; and $R_5$ is selected from the group consisting of: H, halogen, and (C_1-C_4)alkyl optionally substituted with one or more halogen atoms;

wherein in any heterocyclic ring one or more of the ring members are selected from NH, N, O, and S;

wherein in all saturated or partially unsaturated rings one or two members of the rings are optionally C(═O) and/or C(═NH) and/or C[═N(C_1-C_4)alkyl], wherein saturated alkyl refers to a linear or branched hydrocarbon chain which contains only single bonds; and unsaturated alkyl refers to a linear or branched hydrocarbon chain which contains one or two double bonds and/or one or two triple bonds;

wherein in any alkyl group one or two chain members selected from CH_2 or CH are optionally replaced by chain members independently selected from N, NR_4, O, C(═O), C(═O)NR_4, NR_4C(═O), and S; and when in a compound of formula (I) B_1 is a radical of formula (C″) and the moiety —NR^aR^b has the formula (M^4), then the pyridine group in (M^4) is other than 3-methylpyridin-2-ylamino-, 4-methylpyridin-2-ylamino-, 5-methylpyridin-2-ylamino-, 6-methylpyridin-2-ylamino-, 5-chloropyridin-2-ylamino-, or 5-bromopyridin-2-ylamino-; and when in a compound of formula (I) B_1 is a radical of formula (C″) and the moiety —NR^aR^b has the formula (M^4), then $R_1$ is other than phenyl or substituted phenyl.

2. The compound of formula (I) according to claim 1, wherein the moiety —NR^aR^b of the formula (M^3) has the formula (M^{3'})

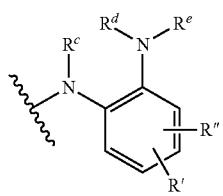
(M³')

3. The compound of formula (I) according to claim 1, wherein B₁ is a radical of formula (A").

4. The compound of formula (I) according to 1, wherein B₁ is a radical of formula (C").

5. The compound of formula (I) according to claim 3, wherein R₁ is selected from the group consisting of saturated or unsaturated (C1-C4)alkyl optionally substituted with one or more halogen atoms; 5- to 6-membered saturated carbocyclic ring optionally substituted with one or more substituents selected from halogen and (C1-C3)alkyl; and 5- to 6-membered saturated heterocyclic ring optionally substituted with one or more substituents selected from halogen and (C1-C3)alkyl.

6. The compound of formula (I) according to claim 3, wherein R₂ is H or saturated or unsaturated (C₁-C₄)alkyl optionally substituted with one or more halogen atoms.

7. The compound of formula (I) according to claim 3, wherein Z₁ is a biradical selected from the group consisting of a formula (E), formula (F'''), and formula (H').

8. The compound of formula (I) according to claim 1, wherein r is 0.

9. A pharmaceutical composition which comprises a therapeutically effective amount of a compound of formula (I) as defined in claim 1, together with one or more pharmaceutically acceptable excipients or carriers.

10. The compound of formula (I) according to claim 4, wherein R₁ is selected from the group consisting of saturated or unsaturated (C₁-C₄)alkyl optionally substituted with one or more halogen atoms; 5- to 6-membered saturated carbocyclic ring optionally substituted with one or more substituents selected from halogen and (C₁-C₃)alkyl; and 5- to 6-membered saturated heterocyclic ring optionally substituted with one or more substituents selected from halogen and (C₁-C₃)alkyl; and R₂ is H or saturated or unsaturated (C₁-C₄)alkyl optionally substituted with one or more halogen atoms.

11. The compound of formula (I) according to claim 4, wherein Z₁ is a biradical selected from the group consisting of a formula (E), formula (F'''), and formula (H').

12. The compound of formula (I) according to claim 1, wherein r is 1 and Z₂ is -Cy⁴-.

13. The compound of formula (I) according to claim 1, wherein the moiety —NR$^a$R$^b$ of the formula (M³) has the formula (M³")

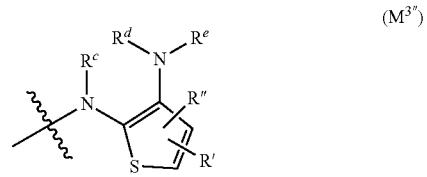
(M³")

14. The compound of formula (I) according to claim 1, which is a compound of formula (IC$^{III}$) or a compound of formula (IC$^{IV}$), wherein R₂ is H or saturated or unsaturated (C₁-C₄)alkyl optionally substituted with one or more halogen atoms.

15. The compound of formula (I) according to claim 1, which is a compound of formula (IA), wherein R₃' is selected from H, halogen, saturated or unsaturated (C₁-C₄) alkyl optionally substituted with one or more halogen atoms; and saturated or unsaturated —O(C₁-C₄)alkyl optionally substituted with one or more halogen atoms.

16. The compound of formula (I) according to claim 1, which is a compound of formula (IC$^{III}$) or a compound of formula (IC$^{IV}$), wherein R₃' is selected from H and saturated or unsaturated (C₁-C₄)alkyl optionally substituted with one or more halogen atoms.

17. The compound of formula (I) according to claim 1, wherein in the moiety of formula (M³), R$^c$, R$^d$, R$^e$ and R' are H, and R" is selected from the group consisting of H, halogen, and 5- or 6-membered heteroaromatic ring.

18. The compound of formula (I) according to claim 1, wherein in the moiety of formula (M³), R$^d$ and R$^e$ are H.

19. The compound of formula (I) according to claim 1, wherein in the moiety of formula (M⁴), R' and R" are H; with the condition that: when B₁ is a radical of formula (C"), then: R₁ is other than phenyl or substituted phenyl.

* * * * *